United States Patent
Petricoin et al.

(10) Patent No.: US 10,690,672 B2
(45) Date of Patent: Jun. 23, 2020

(54) METHODS FOR BREAST CANCER TREATMENT

(71) Applicant: GEORGE MASON UNIVERSITY, Fairfax, VA (US)

(72) Inventors: Emanuel Petricoin, Gainsville, VA (US); Julia Wulfkuhle, Columbia, MD (US)

(73) Assignee: George Mason Research Foundation, Inc., Fairfax, VA (US)

( * ) Notice: Subject to any disclaimer, the term of this patent is extended or adjusted under 35 U.S.C. 154(b) by 23 days.

(21) Appl. No.: 15/533,859

(22) PCT Filed: Dec. 8, 2015

(86) PCT No.: PCT/US2015/064437
§ 371 (c)(1),
(2) Date: Jun. 7, 2017

(87) PCT Pub. No.: WO2016/094373
PCT Pub. Date: Jun. 16, 2016

(65) Prior Publication Data
US 2017/0363630 A1 Dec. 21, 2017

Related U.S. Application Data

(60) Provisional application No. 62/089,120, filed on Dec. 8, 2015.

(51) Int. Cl.
*G01N 33/574* (2006.01)
(52) U.S. Cl.
CPC ... *G01N 33/57415* (2013.01); *G01N 2800/52* (2013.01); *G01N 2800/56* (2013.01)

(58) Field of Classification Search
CPC ......... G01N 33/57415; G01N 2800/52; G01N 2800/56
See application file for complete search history.

(56) References Cited

FOREIGN PATENT DOCUMENTS

WO   WO 2016/094373   6/2016

OTHER PUBLICATIONS

International Preliminary Report on Patentability for PCT/US2015/064437, published as WO2016/094373, dated Jun. 13, 2017.
International Search Report for PCT/US2015/064437, published as WO2016/094373, dated Apr. 1, 2016.
Written Opinion of the International Searching Authority for PCT/US2015/064437, published as WO2016/094373, dated Apr. 1, 2016.
Wulfkuhle et al., Protein pathway activation mapping of LCM tumor epithelium from I-SPY 1 Trial surgical specimens reveals activation of receptor tyrosine kinase drug target signaling networks in the non-responding patient cohort. Cancer Res Dec. 15, 2013 vol. 73 No. 24 Suppl. Abstract p. 04-01, Abstract.
Zang, et al. Activity of lapatinib is independent of EGFR expression level in HER2-overexpressing breast cancer cells, Mol Cancer Ther Jul. 2008 vol. 7 No. 7 pp. 1846-1850. p. 1847 Fig. 1A, Abstract.

*Primary Examiner* — Zohreh A Fay
(74) *Attorney, Agent, or Firm* — Morris, Manning & Martin, LLP; Daniel E. Sineway, Esq.

(57) ABSTRACT

Disclosed herein are methods for treating subjects with breast cancer, comprising determining a therapeutic regimen for cancer by measuring the level (amount) of proteins of one or more biomarkers. Also disclosed are methods of predicting or assessing therapeutic outcome for subject.

9 Claims, 24 Drawing Sheets

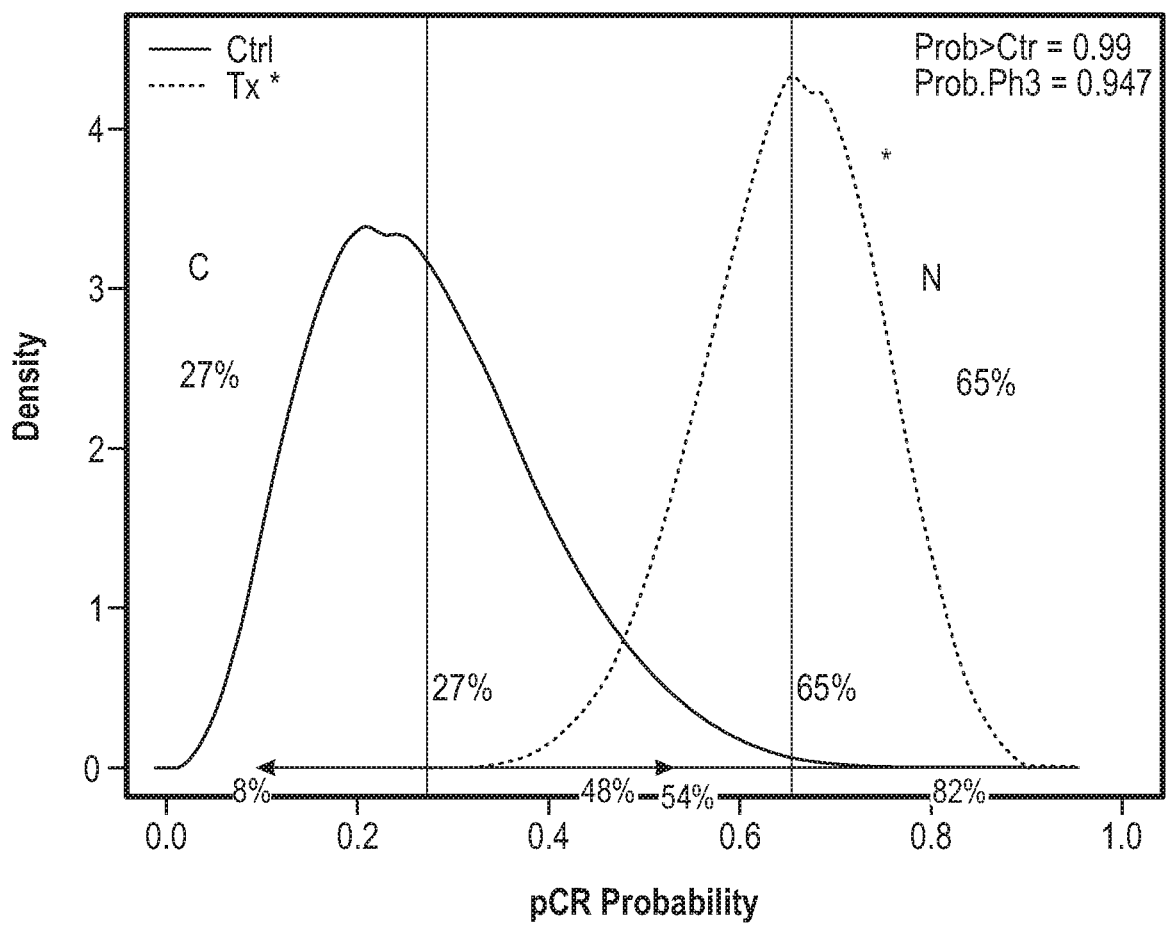

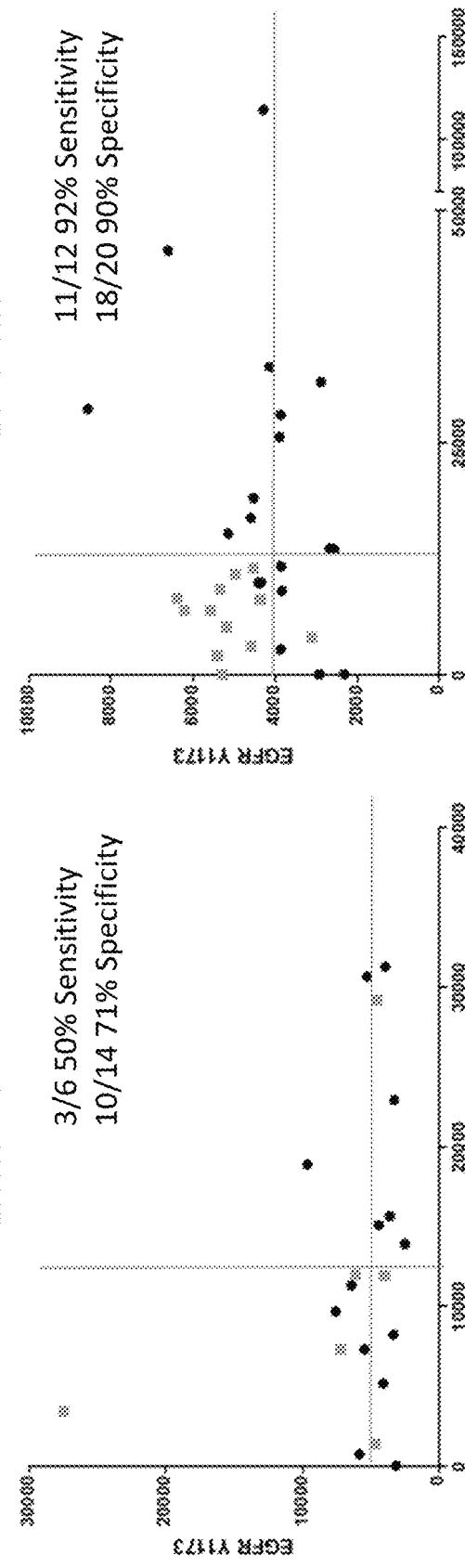
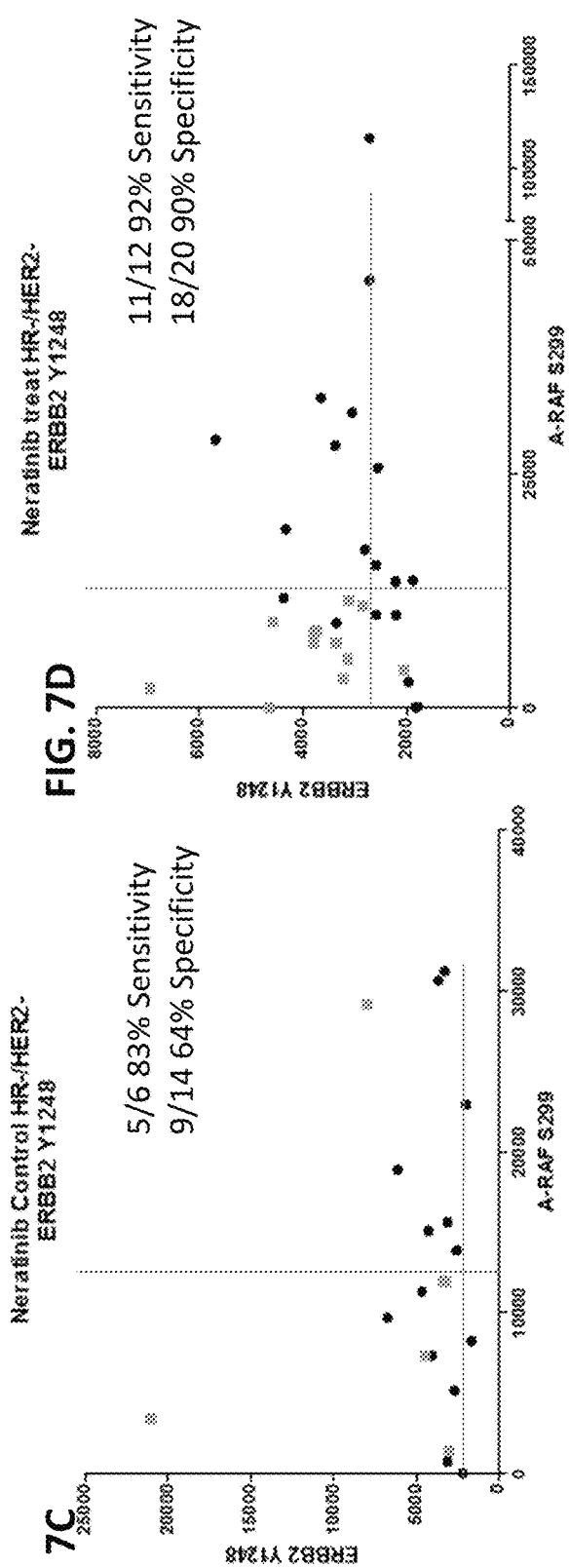
FIG. 7A, FIG. 7B, FIG. 7C, FIG. 7D

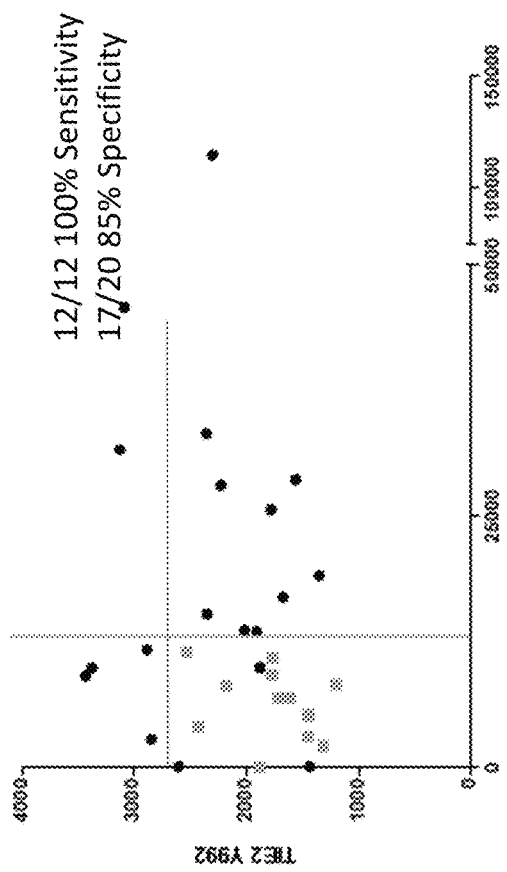
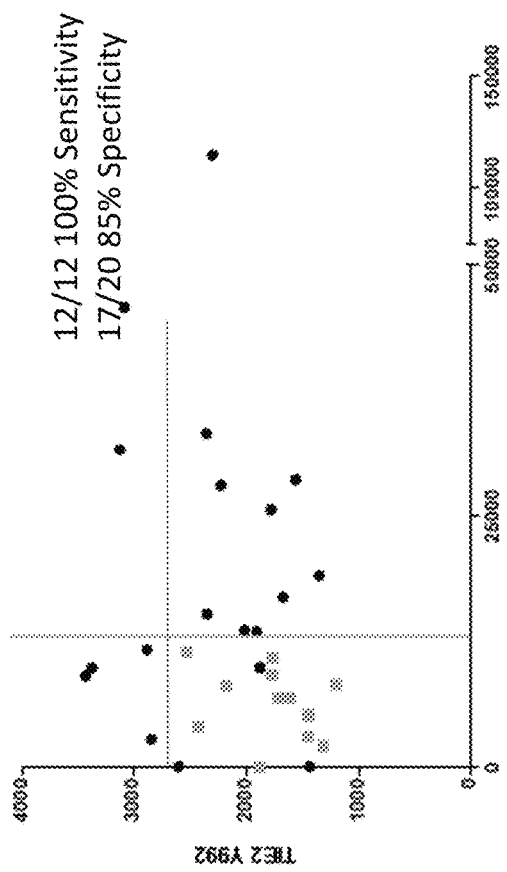
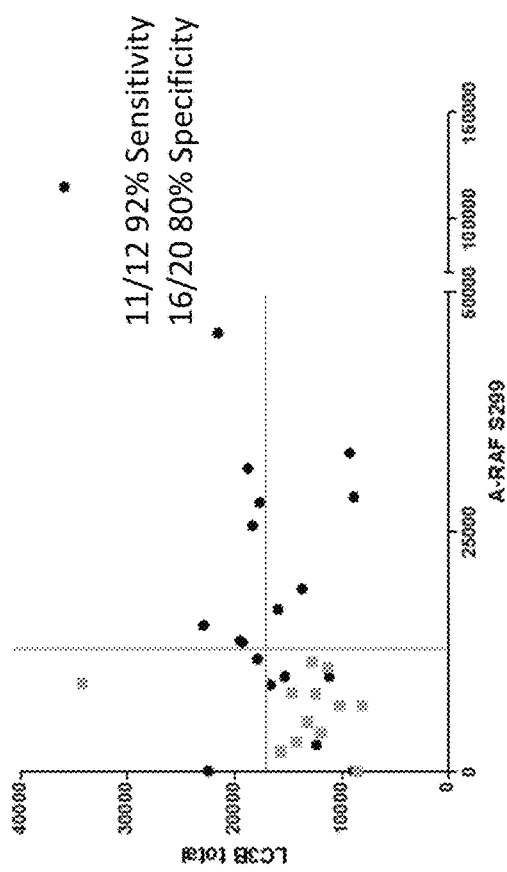
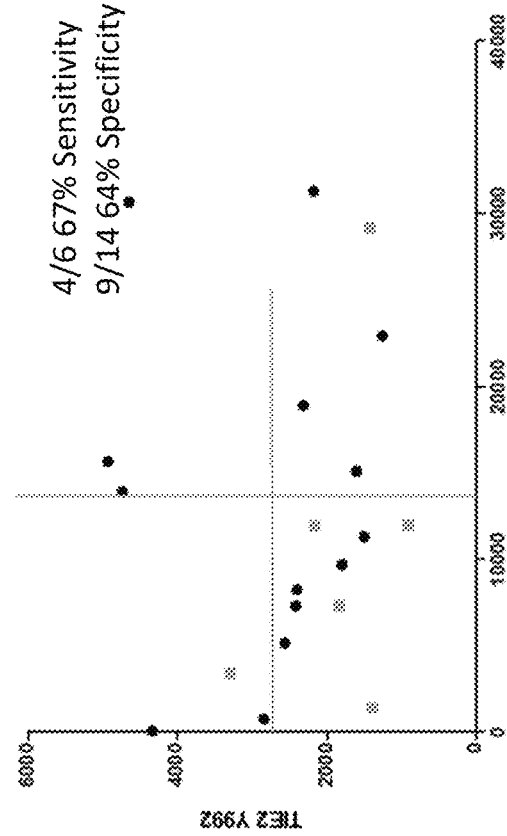
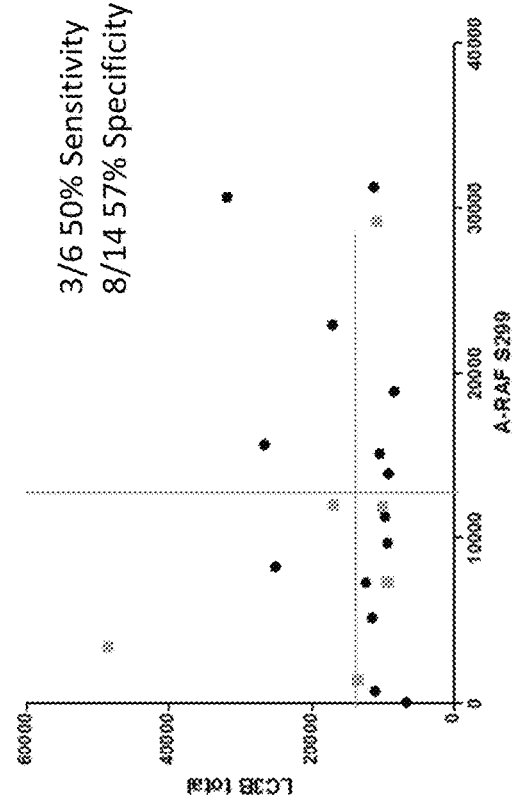

METHODS FOR BREAST CANCER TREATMENT

CROSS-REFERENCE TO RELATED APPLICATIONS

This application is a national stage application under 35 U.S.C. § 371, and claims priority to and the benefit of the filing date of International Application Number PCT/US2015/064437, filed Dec. 8, 2015, which claims priority to U.S. Provisional Patent Application No. 62/089,120, filed Dec. 8, 2014, each of which is herein incorporated in its entirety.

FIELD OF THE INVENTION

Disclosed herein are methods for treating breast cancer comprising predicting or assessing the efficacy of a therapeutic regimen for breast cancer and administering an effective amount of a therapeutic agent to treat breast cancer in subjects. Specifically, disclosed are methods for measuring biomarkers associated with positive treatment outcomes for subjects with breast cancer.

BACKGROUND

Cancer is one of the leading causes of death in the world. Despite improvements in prevention, early detection, treatment and survival, the American Cancer Society states that breast cancer is the second most common newly diagnosed cancer and second leading cause of death among women in the United States. Breast cancer is a cancer that forms in tissues of the breast. The most common type of breast cancer is ductal carcinoma, which begins in the lining of the milk ducts (thin tubes that carry milk from the lobules of the breast to the nipple). Another type of breast cancer is lobular carcinoma, which begins in the lobules (milk glands) of the breast. Invasive breast cancer is breast cancer that has spread from where it began in the breast ducts or lobules to surrounding normal tissue. Breast cancer occurs in both men and women, although male breast cancer is rare.

Targeted therapy is one treatment option available to patients. Target therapy may involve the administration of drugs or macromolecules such as antibodies that are selective for cancer cells and leave normal cells relatively unharmed. Conventional therapeutics for breast cancer are limited in large part because it is not always possible to establish the efficacy of available drugs without trial and error. Further limitations include one or more of the following: high production cost, drug resistance, complications resulting from chemotherapy; and/or safety issues related to the use of the drug. Alternative approaches are needed for improving targeted therapy for breast cancer.

Treatment options for breast cancer include surgery, radiation therapy, hormone therapy, chemotherapy and targeted therapy. Treatment regimens are often determined based on the stage of breast cancer, whether the tumor has hormone receptors, whether the tumor has too much HER2 protein, general health, and other details such as the size of the tumor in relation to the size of the breast, or whether the subject has gone through menopause.

Many therapeutic agents and combinations of therapeutic agents are used to treat breast cancer, and a challenging aspect of treatment is determining which therapeutic or therapeutic combination is most optimal for treatment. Clinical studies continue to compare the most effective treatments against something that may be better. Common therapeutics used for early breast cancer include the anthracyclines (such as doxorubicin/Adriamycin® and epirubicin/Ellence®) and the taxanes (such as paclitaxel/Taxol® and docetaxel/Taxotere®). These may be used in combination with certain other therapeutics, like fluorouracil (5-FU), cyclophosphamide (Cytoxan®), and carboplatin. For cancers that are HER2 positive, the targeted therapeutic trastuzumab (Herceptin®) is often given with one of the taxanes. Pertuzumab (Perjeta®) can also be combined with trastuzumab and docetaxel for HER2 positive cancers.

What is needed are methods and compositions for determining the selection of effective therapeutics for treating cancer such as breast cancer, and methods for treating subjects with cancer.

BRIEF SUMMARY

Disclosed herein are methods for treating breast cancer comprising predicting or assessing therapeutic efficacy of a therapeutic agent that targets EGFR and HER2, including pan-HER inhibitors, the method comprising measuring protein levels of one or more biomarkers disclosed herein in cellular samples from subjects prior to treatment with the therapeutic agent, comparing the measured protein levels of the one or more biomarkers from the subjects to a baseline value for the protein levels of the respective one or more biomarkers, wherein an elevated or decreased level of the proteins of the one or more biomarkers indicates that the subject is a responder to the therapeutic agent. Measurements of proteins for methods disclosed herein may be made by protein detection methods including but not limited to, RPPA, immunohistochemistry, ELISA, suspension bead array, mass spectrometry, dot blot, or western blot. In certain aspects, the proteins that are measured are phosphorylated. In certain aspects, the proteins that are measured are not phosphorylated. In certain aspects, methods comprise measurement of proteins of the one or more biomarkers, or combinations thereof, disclosed herein, wherein the proteins may or may not be phosphorylated: wherein the one or more biomarkers comprise ALK.Y1586; ALK.Y1604; AMPKb1.S108; Caspase.7, cleaved D198; Cyclin.B1 total; Cyclin.D1.total; EGFR.Y1068, EGFR.Y1173, EGFR.Y992, eIF4G.S1108; IGFBP5.total; ERBB2.total; ERBB2.Y1248; ERBB2.Y877; ERBB3.Y1289; ERBB4.Y1284; FAK.Y576.Y577; JAK1.Y1022 and Y1023; JAK2.Y1007; MEK1.2.S217 and S211; MET.Y1234 and Y1235; p70S6K.T389; p70S6K.T412; PI3K.p85.Y458.p55. and Y199; AKT S473; AKT T308; EGFR total; EGFR Y1148; ERBB3 total; ERK1/2 T202/Y204; Heregulin total; mTOR S2448; mTOR total; PTEN S380; SHC Y317; PARP.total; PDGFRa.Y754; RET.Y905; RTK.ROR1.total; SHC.Y317; STAT5.Y694; VEGFR2.Y996; X4EBP1.S65; AMPKa1.S485; A.RAF.S299; IGF1R.Y1131. and IR.Y1146; MCSFR.Y732; A.RAF.S299; LC3B.total; TIE2.Y992; a JAK.STAT.pathway score (which is the sum of the measurements for JAK1 Y1022/Y1023, JAK1 Y1007, STAT1 Y701 STAT2Y727, STAT3 Y705, STAT5 Y694), a mTOR pathway score (which is the sum of the measurements for 4EBP1 S65; eIF4E S209; eIF4G S1108; eIF4G S1108; eIF4G S1108; mTOR S2448; p70S6K S371; p70S6K T389; p70S6K T412; S6RP S240/S244); a HER Family pathway score (which is the sum of the measurements for EGFR Y1068; EGFR Y1173; EGFR Y992; ERBB2 Y1248; ERBB3 Y1289; FAK Y576/Y577; SHC Y317; STAT5 Y694; RET Y905); and a RTK pathway score (which is the sum of the measurements for ALK Y1604; EGFR Y1068; EGFR Y1173; EGFR Y992; ERBB2 Y1248;

ERBB3 Y1289; FAK Y576/Y577; SHC Y317; STAT5 Y694; ERBB2 Y877; ERBB4 Y1284; MET Y1234-Y1235; ROS Y2274; RET Y905), or combinations thereof. As used herein with a biomarker, "total" means that the biomarker is the total amount of the particular protein measured, which would include phosphorylated and non-phosphorylated forms, if such forms exist, of the particular protein. Measurements of proteins may be made by protein detection methods including but not limited to, RPPA, immunohistochemistry, ELISA, suspension bead array, mass spectrometry, dot blot, or western blot.

Disclosed herein are methods of treating breast cancer comprising predicting or assessing an increased likelihood of tumor shrinkage after treatment with a TKI (tyrosine kinase inhibitor) therapeutic agent that targets EGFR and HER2, comprising a) measuring, in a pre-treatment tumor sample comprising cancer cells from a subject, protein levels of one or more biomarkers disclosed herein, b) comparing the measured protein levels of the one or more biomarkers from the subjects to a baseline value for the respective protein levels of the one or more biomarkers, wherein an elevated or decreased level of the proteins of the respective one or more biomarkers indicates that the subject is a responder to the therapeutic agent and has an increased likelihood of tumor shrinkage after treatment with the TKI therapeutic agent, and administering an effective amount of a therapeutic agent to treat the breast cancer. One or more biomarkers comprise, ALK.Y1586; ALK.Y1604; AMPKb1.S108; Caspase.7, cleaved D198; Cyclin.B1 total; Cyclin.D1.total; EGFR.Y1068, EGFR.Y1173, EGFR.Y992, eIF4G.S1108; IGFBP5.total; ERBB2.total; ERBB2.Y1248; ERBB2.Y877; ERBB3.Y1289; ERBB4.Y1284; FAK.Y576.Y577; JAK1.Y1022 and Y1023; JAK2.Y1007; MEK1.2.S217 and S211; MET.Y1234 and Y1235; p70S6K.T389; p70S6K.T412; PI3K.p85.Y458.p55. and Y199; AKT S473; AKT T308; EGFR total; EGFR Y1148; ERBB3 total; ERK1/2 T202/Y204; Heregulin total; mTOR S2448; mTOR total; PTEN S380; SHC Y317; PARP.total; PDGFRa.Y754; RET.Y905; RTK.ROR1.total; SHC.Y317; STAT5.Y694; VEGFR2.Y996; X4EBP1.S65; AMPKa1.S485; A.RAF.S299; IGF1R.Y1131. and IR.Y1146; MCSFR.Y732; A.RAF.S299; LC3B.total; TIE2.Y992; a JAK.STAT.pathway score (which is the sum of the measurements for JAK1 Y1022/Y1023, JAK1 Y1007, STAT1 Y701 STAT2Y727, STAT3 Y705, STAT5 Y694), a mTOR pathway score (which is the sum of the measurements for 4EBP1 S65; eIF4E S209; eIF4G S1108; eIF4G S1108; eIF4G S1108; mTOR S2448; p70S6K S371; p70S6K T389; p70S6K T412; S6RP S240/S244); a HER Family pathway score (which is the sum of the measurements for EGFR Y1068; EGFR Y1173; EGFR Y992; ERBB2 Y1248; ERBB3 Y1289; FAK Y576/Y577; SHC Y317; STAT5 Y694; RET Y905); and a RTK pathway score (which is the sum of the measurements for ALK Y1604; EGFR Y1068; EGFR Y1173; EGFR Y992; ERBB2 Y1248; ERBB3 Y1289; FAK Y576/Y577; SHC Y317; STAT5 Y694; ERBB2 Y877; ERBB4 Y1284; MET Y1234-Y1235; ROS Y2274; RET Y905), or combinations thereof. Measurements of proteins may be made by protein detection methods including but not limited to, RPPA, immunohistochemistry, ELISA, suspension bead array, mass spectrometry, dot blot, or western blot In an aspect, disclosed is a method for treating breast cancer comprising predicting or assessing an increased likelihood of tumor shrinkage after treatment with a TKI therapeutic agent that targets EGFR and HER2, comprising measuring, in a pre-treatment tumor sample comprising cancer cells from a subject, protein levels of one or more biomarkers disclosed herein, comparing the measured protein levels of the one or more biomarkers from the subjects to a baseline value for the respective protein levels of the one or more biomarkers, wherein an elevated or decreased level of the one or more biomarkers indicates that the subject is a responder to the therapeutic agent and has an increased likelihood of tumor shrinkage after treatment with the TKI therapeutic agent, wherein the one or more biomarkers comprise, AKT S473, AKT T308, EGFR total, EGFR Y1068, EGFR Y1148, EGFR Y1173, EGFR Y992, ERBB2 total, ERBB2 Y1248, ERBB3 total, ERBB3 Y1289, ERK1/2 T202/Y204, Heregulin total, mTOR S2448, mTOR total, PI3K p85 Y458/p55 Y199, PTEN S380, and SHC Y317, or combinations thereof, and administering an effective amount of a therapeutic agent to treat the breast cancer. As used herein, a "pre-treatment tumor sample" means a sample obtained from a subject before the subject is administered the particular therapeutic agent or agents under consideration, and does not mean that the subject has not previously been treated with chemotherapeutic agents or other therapies. A subject may have undergone one or more therapeutic regimens, and a pre-treatment tumor sample is the sample obtained before the administration of a therapeutic agent, such as a TKI that targets EGFR and/or HER2, or a pan-HER inhibitor, or a pan-EGFR inhibitor.

Disclosed are methods of treating cancer in a subject comprising administering a TKI that targets EGFR and HER2, wherein the subject has been identified as having an elevated or decreased level (amount) of proteins of one or more biomarkers, wherein the protein level measured is compared to a baseline value for the proteins of the respective one or more biomarkers, wherein the one or more biomarkers comprise ALK.Y1586; ALK.Y1604; AMPKb1.S108; Caspase.7, cleaved D198; Cyclin.B1 total; Cyclin.D1.total; EGFR.Y1068, EGFR.Y1173, EGFR.Y992, eIF4G.S1108; IGFBP5.total; ERBB2.total; ERBB2.Y1248; ERBB2.Y877; ERBB3.Y1289; ERBB4.Y1284; FAK.Y576.Y577; JAK1.Y1022 and Y1023; JAK2.Y1007; MEK1.2.S217 and S211; MET.Y1234 and Y1235; p70S6K.T389; p70S6K.T412; PI3K.p85.Y458.p55. and Y199; PARP.total; PDGFRa.Y754; RET.Y905; RTK.ROR1.total; SHC.Y317; STAT5.Y694; VEGFR2.Y996; X4EBP1.S65; AMPKa1.S485; A.RAF.S299; IGF1R.Y1131. and IR.Y1146; MCSFR.Y732; A.RAF.S299; LC3B.total; TIE2.Y992; a JAK.STAT.pathway score (which is the sum of the measurements for JAK1 Y1022/Y1023, JAK1 Y1007, STAT1 Y701 STAT2Y727, STAT3 Y705, STAT5 Y694), a mTOR pathway score (which is the sum of the measurements for 4EBP1 S65; eIF4E S209; eIF4G S1108; eIF4G S1108; eIF4G S1108; mTOR S2448; p70S6K S371; p70S6K T389; p70S6K T412; S6RP S240/S244); a HER Family pathway score (which is the sum of the measurements for EGFR Y1068; EGFR Y1173; EGFR Y992; ERBB2 Y1248; ERBB3 Y1289; FAK Y576/Y577; SHC Y317; STAT5 Y694; RET Y905); and a RTK pathway score (which is the sum of the measurements for ALK Y1604; EGFR Y1068; EGFR Y1173; EGFR Y992; ERBB2 Y1248; ERBB3 Y1289; FAK Y576/Y577; SHC Y317; STAT5 Y694; ERBB2 Y877; ERBB4 Y1284; MET Y1234-Y1235; ROS Y2274; RET Y905); or combinations thereof, and administering an effective amount of a therapeutic agent to treat the breast cancer.

Disclosed are methods of treating cancer in a subject comprising administering a TKI that targets EGFR and HER2, wherein the subject has been identified as having an elevated or decreased level (amount) of proteins of one or more biomarkers, wherein the protein level measured is compared to a baseline value for the proteins of the respective one or more biomarkers, wherein the one or more biomarkers comprise AKT S473, AKT T308, EGFR total, EGFR Y1068, EGFR Y1148, EGFR Y1173, EGFR Y992, ERBB2 total, ERBB2 Y1248, ERBB3 total, ERBB3 Y1289, ERK1/2 T202/Y204, Heregulin total, mTOR S2448, mTOR total, PI3K p85 Y458/p55 Y199, PTEN S380, and SHC Y317, or combinations thereof, in a pre-treatment tumor sample comprising cancer cells obtained from the subject, and administering an effective amount of a therapeutic agent to treat the breast cancer.

Disclosed are methods of treating cancer in a subject comprising, a) measuring in a pre-treatment tumor sample comprising cancer cells from a subject, protein levels of one or more biomarkers disclosed herein, b) comparing the measured protein levels of the one or more biomarkers from the subjects to a baseline value for the respective protein levels of the one or more biomarkers, wherein the one or more biomarkers comprise ALK.Y1586; ALK.Y1604; AMPKb1. S108; Caspase.7, cleaved D198; Cyclin.B1 total; Cyclin.D1.total; EGFR.Y1068, EGFR.Y1173, EGFR.Y992, eIF4G.S1108; IGFBP5.total; ERBB2.total; ERBB2.Y1248; ERBB2.Y877; ERBB3.Y1289; ERBB4.Y1284; FAK.Y576.Y577; JAK1.Y1022 and Y1023; JAK2.Y1007; MEK1.2.S217 and S211; MET.Y1234 and Y1235; p70S6K.T389; p70S6K.T412; PI3K.p85.Y458.p55. and Y199; PARP.total; PDGFRa.Y754; RET.Y905; RTK.ROR1.total; SHC.Y317; STAT5.Y694; VEGFR2.Y996; X4EBP1.S65; AMPKa1.S485; A.RAF.S299; IGF1R.Y1131. and IR.Y1146; MCSFR.Y732; A.RAF.S299; LC3B.total; TIE2.Y992; a JAK.STAT.pathway score (which is the sum of the measurements for JAK.STAT and related proteins in the JAK.STATpathway), a mTOR pathway score (which is the sum of the measurements for 4EBP1 S65; eIF4E S209; eIF4G S1108; eIF4G S1108; eIF4G S1108; mTOR S2448; p70S6K S371; p70S6K T389; p70S6K T412; S6RP S240/S244); a HER Family pathway score (which is the sum of the measurements for EGFR Y1068; EGFR Y1173; EGFRY992; ERBB2 Y1248; ERBB3 Y1289; FAK Y576/Y577; SHC Y317; STAT5 Y694; RET Y905); and a RTK pathway score (which is the sum of the measurements for ALK Y1604; EGFR Y1068; EGFR Y1173; EGFR Y992; ERBB2 Y1248; ERBB3 Y1289; FAK Y576/Y577; SHC Y317; STAT5 Y694; ERBB2 Y877; ERBB4 Y1284; MET Y1234-Y1235; ROS Y2274; RET Y905); or combinations thereof, wherein an elevated or decreased level of the one or more biomarkers indicates that the subject is a responder to a therapeutic agent and has an increased likelihood of tumor shrinkage after treatment with the therapeutic agent; and administering to the subject an effective amount of one or more therapeutic agents, including but not limited to, a TKI, an agent that targets EGFR and HER2, neratinib, affatinib, lapatinib and other known pan-HER or pan-EGFR inhibitors. Methods disclosed herein may comprises a series of active steps including first measuring the levels (amounts) of one or more particular biomarkers to detect a change in one or more biomarkers from the baseline measured biomarkers. A change in a biomarker may include, but is not limited to an elevation or reduction in a) amounts (levels) of particular individual proteins, b) combinations of particular proteins, c) phosphorylation of particular individual proteins or combinations of proteins, and/or d) total protein; The change is recognized by comparing one or more measured biomarkers from the subject, such as those comprising the levels of phosphorylation and/or total protein levels of the proteins selected, to exogenous reference standards and/or calibration standards (also referred to herein as a baseline value, and by implication, each biomarker included in a method would have its particular baseline value for comparison). Other steps of methods disclosed herein may comprise interpolating or extrapolating the data; generating a report that describes the biomarkers, such as activation/phosphorylation protein levels or total protein levels, on a patient-by-patient basis; and providing this report to another, such as to a physician, who then can use this information for treating the subject with a therapeutic agent; and administering an effective amount of at least one therapeutic agent to the subject For example, a therapeutic agent may be a TKI that targets EGFR and HER2, including, but not limited to, neratinib, affatinib, lapatinib and other known pan-HER or pan-EGFR inhibitors.

Disclosed are methods of treating cancer in a subject comprising, a) measuring, in a pre-treatment tumor sample comprising cancer cells from a subject, protein levels of one or more biomarkers disclosed herein, b) comparing the measured protein levels of the one or more biomarkers from the subjects to a baseline value for the respective protein levels of the one or more biomarkers, wherein the one or more biomarkers comprise AKT S473, AKT T308, EGFR total, EGFR Y1068, EGFR Y1148, EGFR Y1173, EGFR Y992, ERBB2 total, ERBB2 Y1248, ERBB3 total, ERBB3 Y1289, ERK1/2 T202/Y204, Heregulin total, mTOR S2448, mTOR total, PI3K p85 Y458/p55 Y199, PTEN S380, and SHC Y317; or combinations thereof, wherein an elevated or decreased level of the one or more biomarkers indicates that the subject is a responder to a therapeutic agent and/or has an increased likelihood of tumor shrinkage after treatment with the therapeutic agent. The method further comprises treating the subject with the therapeutic agent. For example, the therapeutic agent may be a TKI that targets EGFR and HER2, including, but not limited to, neratinib, affatinib, lapatinib and other known pan-HER or pan-EGFR inhibitors.

Additional advantages of the disclosed methods will be set forth in part in the description which follows, and in part will be understood from the description, or may be learned by practice of the disclosed methods. The advantages of the disclosed methods will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 2A-D are pCR distribution plots of patients who achieved response in the neratinib (N) and control (C) arms. Area under the curve (AUC) values are shown, FIG. 2A is the distribution plot and AUC for the HER2+/HR− graduating population and FIG. 2B for the EGFR Y1773 biomarker, showing superior AUC for pEGFR Y1773 compared to the predicate HER2+/HR− group, which was determined by FISH/IHC testing. FIGS. 2C and D show superior AUC for additive or subtractive additions of pEGFR Y1773 and HER2+/HR− subgroups.

FIGS. 7A-L show two-way scatter plots for HR−/HER2− subjects, control and treated subjects, for various biomarkers.

DETAILED DESCRIPTION

Figure 1A:
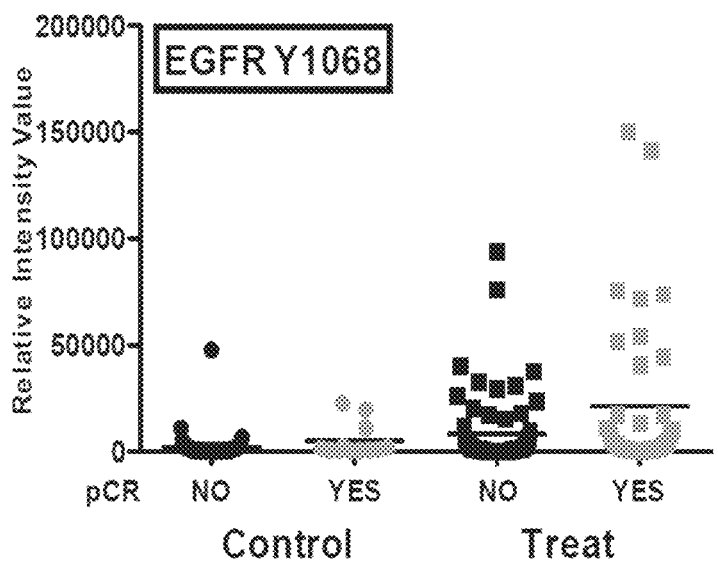
FIGS. 1A-G provide scatter plots of seven HER family signaling pathway biomarkers, comprising proteins and phosphoproteins, (FIG. 1 A—EGFR Y1068, FIG. 1 B—EGFR Y1173, FIG. 1 C—EGFR Y992, FIG. 1 D—ERBB2 total, FIG. 1 E—ERBB2 Y1248, FIG. 1 F—ERBB3 Y1289, FIG. 1 G—SHC Y317) that were statistically significantly elevated ($p<0.05$) in all subjects treated with neratinib (regardless of HER2 and HR status) who achieved pCR (i.e. pCR YES) and not in the matched control arm. The plots show the levels of the measured proteins for the tumor cells that were obtained from the pre-treatment biopsy sample from HER2+ or HER2−, HR+ or HR− breast cancer patients.
Figure 1B:
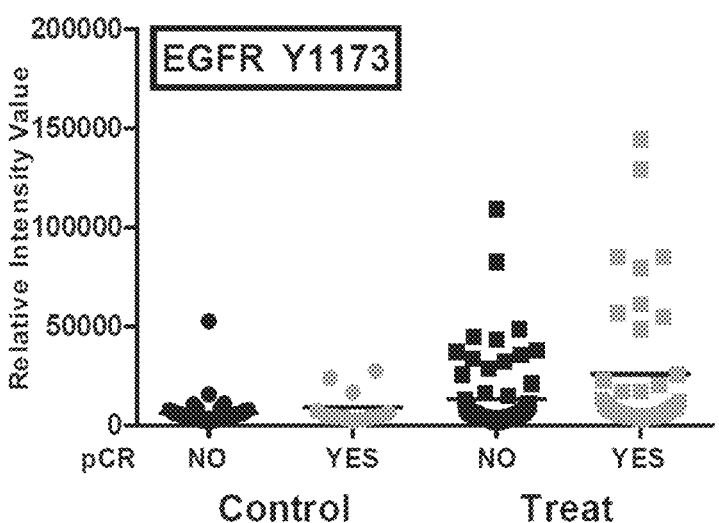
Figure 1C:
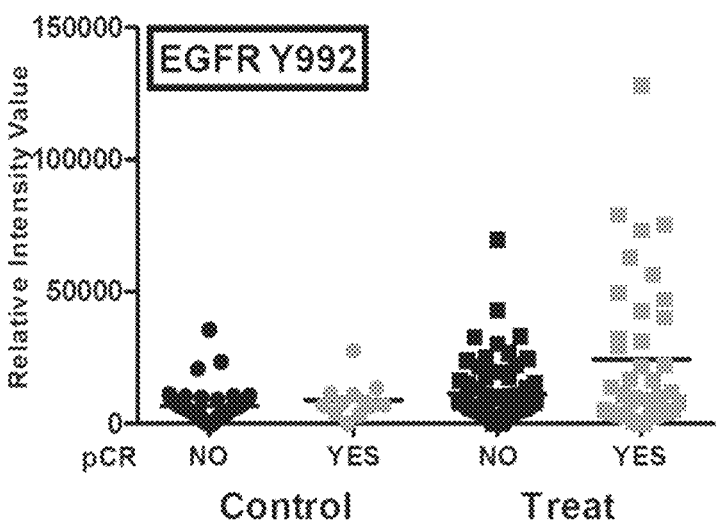
Figure 1D:
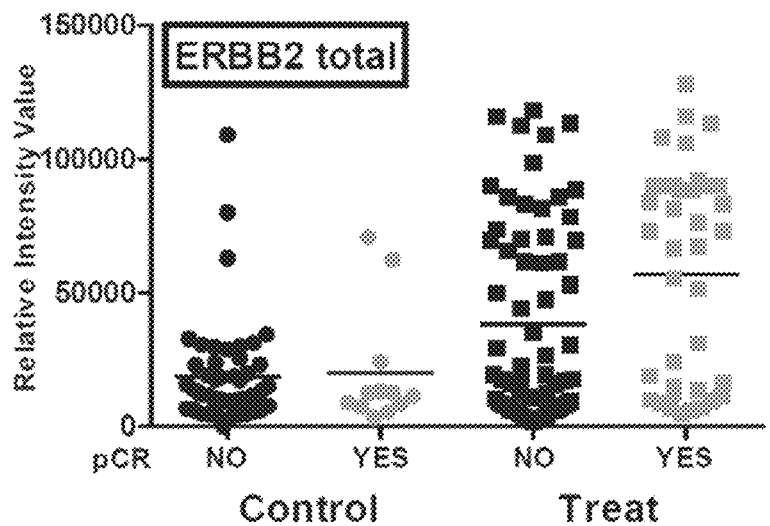
Figure 1E:
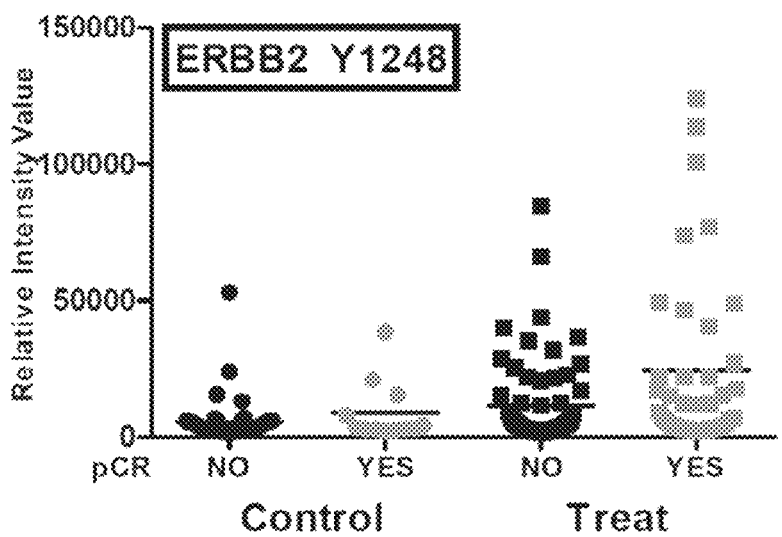
Figure 1F:
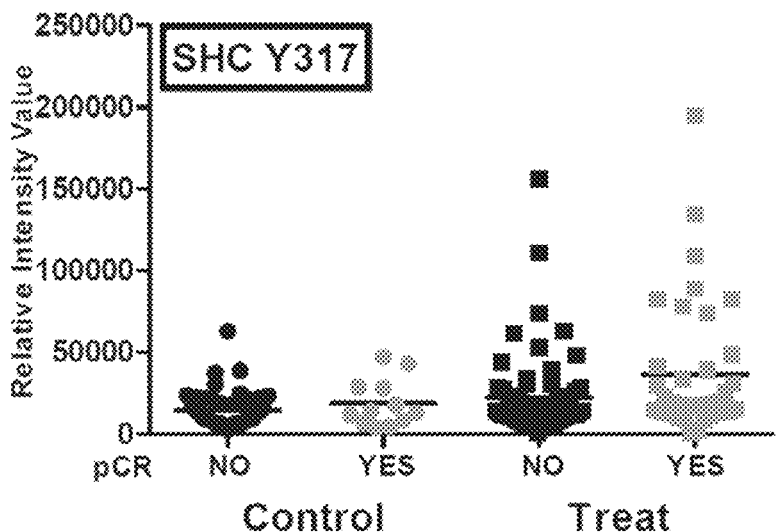
Figure 1G:
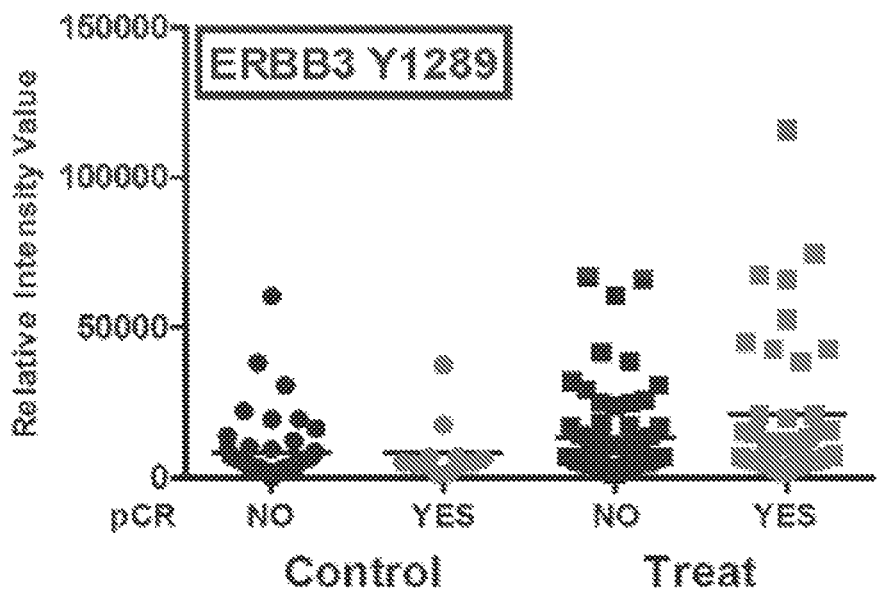

The disclosed methods and compositions may be understood more readily by reference to the following detailed description of particular embodiments and the Examples included therein and to the Figures and their previous and following descriptions.
It is understood that disclosed methods are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Currently, treatment of Stage II/III breast cancer involves neoadjuvant treatment (pre-surgical) with drug regimens that may include therapies targeting specific molecular defects. Disclosed herein are novel methods for treatment of breast cancer comprising identifying biomarkers that predict response to therapeutic agents used in the pre-surgical stage of treatment of cancer. Subjects providing samples (pre-treatment biopsies) for studies described herein were characterized based on measurement of estrogen/hormone receptor (HR) and HER2 (c-erbB2), and were described by HER2−/HR−, HER2+/HR+, HER2+/HR−, HER2−/HR+ phenotypes. Response to treatment was determined by the amount of tumor shrinkage and a lack of appreciable tumor evident at surgery. A response of tumor shrinkage and/or lack of tumor when examined (such as at surgery) is referred to herein as "complete pathological response" (pCR), and has recently been deemed by the US FDA as an appropriate clinical endpoint for therapeutic approval. Neratinib is a therapeutic agent with a mechanism of action that is as a tyrosine kinase inhibitor that binds to and inhibits c-erbB2 and EGFR protein activity and the respective linked downstream pathways. Therapeutic agents, including affatinib, lapatinib and other known pan-HER or pan-EGFR inhibitors, have a similar mechanism of action and are effective in the methods described herein. Methods described herein may comprise obtaining measurements of the amounts proteins from a subject sample using a protein array technology developed by the inventors, and is referred to herein as "reverse phase protein microarray" (RPPA). This microarray allows for quantitative measurement of the amount of proteins and/or phosphorylated proteins in the tumor or cancerous cells from pretreatment sample, for example from biopsy specimens of women with Stage II/III breast cancer. Subjects who may benefit from the methods disclosed herein are subjects who have a high risk of recurrence and who may be treated with a tyrosine kinase inhibitor (TKI), including but not limited to neratinib, in addition to treatment with other chemotherapeutic agents. In the studies disclosed herein neratinib showed statistically significant clinical response in the HER2+/HR− subtype, and pCR was observed in every subtype regardless of HER2/HR status.

Disclosed herein are methods for treating breast cancer comprising treating a subject identified as having breast cancer with at least one therapeutic agent that targets EGFR and HER2, wherein the efficacy of the at least one therapeutic agent has been determined by predicting or assessing therapeutic efficacy of a therapeutic agent that targets EGFR and HER2, comprising a) measuring protein levels of one or more biomarkers disclosed herein in cellular samples from subjects prior to treatment with the therapeutic agent, b) comparing the measured protein levels of the one or more biomarkers from the subjects to a baseline value for the protein levels of the respective one or more biomarkers, wherein an elevated or decreased level of the proteins of the one or more biomarkers indicates that the subject is a responder to the therapeutic agent, and further comprising, administering an effective amount of a therapeutic agent to treat the breast cancer.

A method for treating breast cancer comprises, administering to a subject identified as having breast cancer, at least one therapeutic agent that targets EGFR and HER2, wherein the efficacy of the at least one therapeutic agent has been determined by a) measuring protein levels of one or more biomarkers disclosed herein in cellular samples from subjects prior to treatment with the therapeutic agent, and b) comparing the measured protein levels of the one or more biomarkers from the subjects to a baseline value for the protein levels of the respective one or more biomarkers, wherein an elevated or decreased level of the proteins of the one or more biomarkers indicates that the subject is a responder to the therapeutic agent, wherein the one or more biomarkers comprise ALK.Y1586; ALK.Y1604; AMPKb1.S108; Caspase.7, cleaved D198; Cyclin.B1 total; Cyclin.D1.total; EGFR.Y1068, EGFR.Y1173, EGFR.Y992, eIF4G.S1108; IGFBP5.total; ERBB2.total; ERBB2.Y1248; ERBB2.Y877; ERBB3.Y1289; ERBB4.Y1284; FAK.Y576.Y577; JAK1.Y1022 and Y1023; JAK2.Y1007; MEK1.2.S217 and S211; MET.Y1234 and Y1235; p70S6K.T389; p70S6K.T412; PI3K.p85.Y458.p55. and Y199; AKT S473; AKT T308; EGFR total; EGFR Y1148; ERBB3 total; ERK1/2 T202/Y204; Heregulin total; mTOR S2448; mTOR total; PTEN S380; SHC Y317; PARP.total; PDGFRa.Y754; RET.Y905; RTK.ROR1.total; SHC.Y317;

STAT5.Y694; VEGFR2.Y996; X4EBP1.S65; AMPKa1.S485; A.RAF.S299; IGF1R.Y1131. and IR.Y1146; MCSFR.Y732; A.RAF.S299; LC3B.total; TIE2.Y992; a JAK.STAT.pathway score (which is the sum of the measurements for JAK1 Y1022/Y1023, JAK1 Y1007, STAT1 Y701 STAT2Y727, STAT3 Y705, STAT5 Y694), a mTOR pathway score (which is the sum of the measurements for 4EBP1 S65; eIF4E S209; eIF4G S1108; eIF4G S1108; eIF4G S1108; mTOR S2448; p70S6K S371; p70S6K T389; p70S6K T412; S6RP S240/S244); a HER Family pathway score (which is the sum of the measurements for EGFR Y1068; EGFR Y1173; EGFR Y992; ERBB2 Y1248; ERBB3 Y1289; FAK Y576/Y577; SHC Y317; STAT5 Y694; RET Y905); and a RTK pathway score (which is the sum of the measurements for ALK Y1604; EGFR Y1068; EGFR Y1173; EGFR Y992; ERBB2 Y1248; ERBB3 Y1289; FAK Y576/Y577; SHC Y317; STAT5 Y694; ERBB2 Y877; ERBB4 Y1284; MET Y1234-Y1235; ROS Y2274; RET Y905), or combinations thereof. In certain aspects, the proteins that are measured are phosphorylated. In certain aspects, the proteins that are measured are not phosphorylated. In an aspect, methods for treating breast cancer comprise administering to a subject identified as having breast cancer an effective amount of at least one therapeutic agent that targets EGFR and HER2, wherein determining the efficacy of the at least one therapeutic agent comprises predicting or assessing therapeutic efficacy of a therapeutic agent that targets EGFR and HER2, comprise measurement of proteins of one or more biomarkers comprising ALK.Y1586; ALK.Y1604; AMPKb1.S108; Caspase.7, cleaved D198; Cyclin.B1 total; Cyclin.D1.total; EGFR.Y1068, EGFR.Y1173, EGFR.Y992, eIF4G. S1108; IGFBP5.total; ERBB2.total; ERBB2.Y1248; ERBB2.Y877; ERBB3.Y1289; ERBB4.Y1284; FAK.Y576.Y577; JAK1.Y1022 and Y1023; JAK2.Y1007; MEK1.2.S217 and S211; MET.Y1234 and Y1235; p70S6K.T389; p70S6K.T412; PI3K.p85.Y458.p55. and Y199; AKT S473; AKT T308; EGFR total; EGFR Y1148; ERBB3 total; ERK1/2 T202/Y204; Heregulin total; mTOR S2448; mTOR total; PTEN S380; SHC Y317; PARP.total; PDGFRa.Y754; RET.Y905; RTK.ROR1.total; SHC.Y317; STAT5.Y694; VEGFR2.Y996; X4EBP1.S65; AMPKa1.S485; A.RAF.S299; IGF1R.Y1131. and IR.Y1146; MCSFR.Y732; A.RAF.S299; LC3B.total; TIE2.Y992; a JAK.STAT.pathway score (which is the sum of the measurements for JAK1 Y1022/Y1023, JAK1 Y1007, STAT1 Y701 STAT2Y727, STAT3 Y705, STAT5 Y694), a mTOR pathway score (which is the sum of the measurements for 4EBP1 S65; eIF4E S209; eIF4G S1108; eIF4G S1108; eIF4G S1108; mTOR S2448; p70S6K S371; p70S6K T389; p70S6K T412; S6RP S240/S244); a HER Family pathway score (which is the sum of the measurements for EGFR Y1068; EGFR Y1173; EGFR Y992; ERBB2 Y1248; ERBB3 Y1289; FAK Y576/Y577; SHC Y317; STAT5 Y694; RET Y905); and a RTK pathway score (which is the sum of the measurements for ALK Y1604; EGFR Y1068; EGFR Y1173; EGFR Y992; ERBB2 Y1248; ERBB3 Y1289; FAK Y576/Y577; SHC Y317; STAT5 Y694; ERBB2 Y877; ERBB4 Y1284; MET Y1234-Y1235; ROS Y2274; RET Y905), or combinations thereof. As used herein with a biomarker, "total" means that the biomarker is the total amount of the particular protein measured, which would include phosphorylated and nonphosphorylated forms, if such forms exist, of the particular protein. As used herein, "protein pathway activation module score" or "pathway score" were defined on the basis of known biochemical linkages between the individual phosphoproteins, and for example, were quantitatively measured by RPPA, and could also be measured by protein detection methods including but not limited to, RPPA, immunohistochemistry, ELISA, suspension bead array, mass spectrometry, dot blot, or western blot. Pathway activation module scores were calculated by first scaling the relative intensity values within each endpoint to the sample with the highest value, resulting in values ranging from 1 to 0 that were designated as the "single endpoint score". Second, final pathway activation module scores for each sample were generated by summing the single individual phosphoprotein score for each endpoint component in a given module. These scores, referred to as a "protein pathway activation module score" or "pathway score" represent the entire activation status of each of the pathways in each patient.

In an aspect, methods for treating breast cancer comprising administering to a subject identified as having breast cancer an effective amount of at least one therapeutic agent that targets EGFR and HER2, wherein the efficacy of the at least one therapeutic agent has been determined by predicting or assessing therapeutic efficacy of a therapeutic agent that targets EGFR and HER2, comprise measurement of proteins of one or more biomarkers comprising ALK.Y1586; Cyclin.B1. total; Cyclin.D1.PI3K.p85.Y458.p55.Y199; EGFR.Y1068; EGFR.Y1173; EGFR.Y992; eIF4G.S1108; ERBB2 total; ERBB2.Y1248; ERBB4.Y1284; RET.Y905; SHC.Y317; ERBB2.Y877; mTOR total; HER total; or RTK total; or combinations thereof. Measurements may be made by RPPA for this method and any other method disclosed herein. Measurements may be made using protein detection methods including but not limited to, RPPA, immunohistochemistry, ELISA, suspension bead array, mass spectrometry, dot blot, or western blot. In an aspect, methods for predicting or assessing or assessing the therapeutic efficacy of a therapeutic agent that targets EGFR and HER2, comprise measurement of proteins of one or more biomarkers comprising Cyclin.D1.total; IGFBP5.total; or PARP.total; or combinations thereof. In an aspect, methods for predicting or assessing therapeutic efficacy of a therapeutic agent that targets EGFR and HER2, comprise measurement of proteins of one or more biomarkers comprising mTOR pathway activation score; HER family pathway activation score; RTK pathway activation score; ALK.Y1586; EGFR.Y992; p70S6K.T412, or Cyclin.B1.total; or combinations thereof. In an aspect, methods for predicting or assessing therapeutic efficacy of a therapeutic agent that targets EGFR and HER2, comprise measurement of proteins of one or more biomarkers comprising AKT S473; AKT T308; EGFR; EGFR Y1068; EGFR Y1148; EGFR Y1173; EGFR Y992; ERBB2; ERBB2 Y1248; ERBB3; ERBB3 Y1289; ERK1/2 T202/Y204; Heregulin; mTOR; mTOR S2448; PI3K p85 Y458/p55 Y199; PTEN S380; or SHC Y317; or combinations thereof. In an aspect, methods for predicting or assessing therapeutic efficacy of a therapeutic agent that targets EGFR and HER2, comprise measurement of proteins of one or more biomarkers comprising EGFR Y1068; EGFR Y1173; EGFR Y992; ERBB2 total; ERBB2 Y1248; ERBB3 Y1289; SHC Y317; or combinations thereof. In an aspect, methods for predicting or assessing therapeutic efficacy of a therapeutic agent that targets EGFR and HER2, comprise measurement of proteins of one or more biomarkers comprising IGFBP5.total. In an aspect, methods for predicting or assessing therapeutic efficacy of a therapeutic agent that targets EGFR and HER2, comprise measurement of proteins of one or more biomarkers comprising EGFR.Y1173; ERBB2.Y1248; ERBB4.Y1284; PDGFRa.Y754; or RTK-.ROR1 total; or combinations thereof. In an aspect, methods for predicting or assessing therapeutic efficacy of a therapeutic agent that targets EGFR and HER2, comprise measurement of proteins of one or more biomarkers comprising A.RAF.S299; LC3B.total; or TIE2.Y992; or combinations thereof. As used herein, "measurement of proteins" includes measurement of the amount (i.e., mg or µg), the presence or absence of a protein; whether a protein is phosphorylated or not, or other alterations to a protein, and each of the measurements are compared to the baseline or control status of the biomarker. Those of skill in the art can establish a baseline or control reference point for a particular biomarker and such a baseline or control reference point may be derived from cancer cells or from normal (non-cancerous) cells.

Disclosed herein are methods of predicting or assessing an increased likelihood of tumor shrinkage after treatment with a TKI (tyrosine kinase inhibitor) therapeutic agent that targets EGFR and HER2, comprising a) measuring, in a pre-treatment tumor sample comprising cancer cells from a subject, protein levels of one or more biomarkers disclosed herein, b) comparing the measured protein levels of the one or more biomarkers from the subjects to a baseline value for the respective protein levels of the one or more biomarkers, wherein an elevated or decreased level of the proteins of the respective one or more biomarkers indicates that the subject is a responder to the therapeutic agent and has an increased likelihood of tumor shrinkage after treatment with the TKI therapeutic agent. One or more biomarkers comprise, ALK.Y1586; ALK.Y1604; AMPKb1.S108; Caspase.7, cleaved D198; Cyclin.B1 total; Cyclin.D1.total; EGFR.Y1068, EGFR.Y1173, EGFR.Y992, eIF4G.S1108; IGFBP5.total; ERBB2.total; ERBB2.Y1248; ERBB2.Y877; ERBB3.Y1289; ERBB4.Y1284; FAK.Y576.Y577; JAK1.Y1022 and Y1023; JAK2.Y1007; MEK1.2.S217 and S211; MET.Y1234 and Y1235; p70S6K.T389; p70S6K.T412; PI3K.p85.Y458.p55. and Y199; AKT S473; AKT T308; EGFR total; EGFR Y1148; ERBB3 total; ERK1/2 T202/Y204; Heregulin total; mTOR S2448; mTOR total; PTEN S380; SHC Y317; PARP.total; PDGFRa.Y754; RET.Y905; RTK.ROR1.total; SHC.Y317; STAT5.Y694; VEGFR2.Y996; X4EBP1.S65; AMPKa1.S485; A.RAF.S299; IGF1R.Y1131. and IR.Y1146; MCSFR.Y732; A.RAF.S299; LC3B.total; TIE2.Y992; a JAK.STAT.pathway score (which is the sum of the measurements for JAK1 Y1022/Y1023, JAK1 Y1007, STAT1 Y701 STAT2Y727, STAT3 Y705, STAT5 Y694), a mTOR pathway score (which is the sum of the measurements for 4EBP1 S65; eIF4E S209; eIF4G S1108; eIF4G S1108; eIF4G S1108; mTOR S2448; p70S6K S371; p70S6K T389; p70S6K T412; S6RP S240/S244); a HER Family pathway score (which is the sum of the measurements for EGFR Y1068; EGFR Y1173; EGFR Y992; ERBB2 Y1248; ERBB3 Y1289; FAK Y576/Y577; SHC Y317; STAT5 Y694; RET Y905); and a RTK pathway score (which is the sum of the measurements for ALK Y1604; EGFR Y1068; EGFR Y1173; EGFR Y992; ERBB2 Y1248; ERBB3 Y1289; FAK Y576/Y577; SHC Y317; STAT5 Y694; ERBB2 Y877; ERBB4 Y1284; MET Y1234-Y1235; ROS Y2274; RET Y905), or combinations thereof.

In an aspect, a method for treating breast cancer comprises, administering to a subject identified as having breast cancer, at least one therapeutic agent that targets EGFR and HER2, wherein the efficacy of the at least one therapeutic agent has been determined by predicting or assessing an increased likelihood of tumor shrinkage after treatment with a TKI therapeutic agent comprise measurement of proteins of one or more biomarkers comprising ALK.Y1586; Cyclin.B1. total; Cyclin.D1.PI3K.p85.Y458.p55.Y199; EGFR.Y1068; EGFR.Y1173; EGFR.Y992; eIF4G.S1108; ERBB2 total; ERBB2.Y1248; ERBB4.Y1284; RET.Y905; SHC.Y317; ERBB2.Y877; mTOR total; HER total; or RTK total; or combinations thereof. In an aspect, a method for treating breast cancer comprises, administering to a subject identified as having breast cancer, at least one therapeutic agent that targets EGFR and HER2, wherein the efficacy of the at least one therapeutic agent has been determined by predicting or assessing an increased likelihood of tumor shrinkage after treatment with a TKI therapeutic agent comprise measurement of proteins of one or more biomarkers comprising Cyclin.D1.total; IGFBP5.total; or PARP.total; or combinations thereof. In an aspect, a method for treating breast cancer comprises, administering to a subject identified as having breast cancer, at least one therapeutic agent that targets EGFR and HER2, wherein the efficacy of the at least one therapeutic agent has been determined by predicting or assessing an increased likelihood of tumor shrinkage after treatment with a TKI therapeutic agent comprise measurement of proteins of one or more biomarkers comprising mTOR pathway activation.score; HER Family pathway activation score; RTK pathway activation score; ALK.Y1586; EGFR.Y992; p70S6K.T412, or Cyclin.B1.total; or combinations thereof. In an aspect, a method for treating breast cancer comprises, administering to a subject identified as having breast cancer, at least one therapeutic agent that targets EGFR and HER2, wherein the efficacy of the at least one therapeutic agent has been determined by predicting or assessing an increased likelihood of tumor shrinkage after treatment with a TKI therapeutic agent comprise measurement of proteins of one or more biomarkers comprising AKT S473; AKT T308; EGFR; EGFR Y1068; EGFR Y1148; EGFR Y1173; EGFR Y992; ERBB2; ERBB2 Y1248; ERBB3; ERBB3 Y1289; ERK1/2 T202/Y204; Heregulin; mTOR; mTOR S2448; PI3K p85 Y458/p55 Y199; PTEN S380; or SHC Y317; or combinations thereof. In an aspect, a method for treating breast cancer comprises, administering to a subject identified as having breast cancer, at least one therapeutic agent that targets EGFR and HER2, wherein the efficacy of the at least one therapeutic agent has been determined by predicting or assessing an increased likelihood of tumor shrinkage after treatment with a TKI therapeutic agent comprise measurement of proteins of one or more biomarkers comprising EGFR Y1068; EGFR Y1173; EGFR Y992; ERBB2 total; ERBB2 Y1248; ERBB3 Y1289; SHC Y317; or combinations thereof. In an aspect, a method for treating breast cancer comprises, administering to a subject identified as having breast cancer, at least one therapeutic agent that targets EGFR and HER2, wherein the efficacy of the at least one therapeutic agent has been determined by predicting or assessing an increased likelihood of tumor shrinkage after treatment with a TKI therapeutic agent comprise measurement of proteins of one or more biomarkers comprising IGFBP5.total. In an aspect a method for treating breast cancer comprises, administering to a subject identified as having breast cancer, at least one therapeutic agent that targets EGFR and HER2, wherein the efficacy of the at least one therapeutic agent has been determined by predicting or assessing an increased likelihood of tumor shrinkage after treatment with a TKI therapeutic agent comprise measurement of proteins of one or more biomarkers comprising EGFR.Y1173; ERBB2.Y1248; ERBB4.Y1284; PDGFRa.Y754; or RTK.ROR1.total; or combinations thereof. In an aspect, a method for treating breast cancer comprises, administering to a subject identified as having breast cancer, at least one therapeutic agent that targets EGFR and HER2, wherein the efficacy of the at least one therapeutic agent has been determined by predicting or assessing an increased likelihood of tumor shrinkage after treatment with a TKI therapeutic agent comprise measurement of proteins of one or more biomarkers comprising A.RAF.S299; LC3B.total; or TIE2.Y992; or combinations thereof.

Disclosed are methods of treating cancer in a subject comprising administering an effective amount of a TKI that targets EGFR and HER2, wherein the subject has been identified as having an elevated or decreased level (amount) of proteins of one or more biomarkers, wherein the protein level measured is compared to a baseline value for the proteins of the respective one or more biomarkers, wherein the one or more biomarkers comprise ALK.Y1586; ALK.Y1604; AMPKb1.S108; Caspase.7, cleaved D198; Cyclin.B1 total; Cyclin.D1.total; EGFR.Y1068, EGFR.Y1173, EGFR.Y992, eIF4G. S1108; IGFBP5.total; ERBB2.total; ERBB2.Y1248; ERBB2.Y877; ERBB3.Y1289; ERBB4.Y1284; FAK.Y576.Y577; JAK1.Y1022 and Y1023; JAK2.Y1007; MEK1.2.S217 and S211; MET.Y1234 and Y1235; p70S6K.T389; p70S6K.T412; PI3K.p85.Y458.p55. and Y199; AKT S473; AKT T308; EGFR total; EGFR Y1148; ERBB3 total; ERK1/2 T202/Y204; Heregulin total; mTOR S2448; mTOR total; PTEN S380; SHC Y317; PARP.total; PDGFRa.Y754; RET.Y905; RTK.ROR1.total; SHC.Y317; STAT5.Y694; VEGFR2.Y996; X4EBP1.S65; AMPKa1.S485; A.RAF.S299; IGF1R.Y1131. and IR.Y1146; MCSFR.Y732; A.RAF.S299; LC3B.total; TIE2.Y992; a JAK.STAT.pathway score (which is the sum of the measurements for JAK1 Y1022/Y1023, JAK1 Y1007, STAT1 Y701 STAT2Y727, STAT3 Y705, STAT5 Y694), a mTOR pathway score (which is the sum of the measurements for 4EBP1 S65; eIF4E S209; eIF4G S1108; eIF4G S1108; eIF4G S1108; mTOR S2448; p70S6K S371; p70S6K T389; p70S6K T412; S6RP S240/S244); a HER Family pathway score (which is the sum of the measurements for EGFR Y1068; EGFR Y1173; EGFR Y992; ERBB2 Y1248; ERBB3 Y1289; FAK Y576/Y577; SHC Y317; STAT5 Y694; RET Y905); and a RTK pathway score (which is the sum of the measurements for ALK Y1604; EGFR Y1068; EGFR Y1173; EGFR Y992; ERBB2 Y1248; ERBB3 Y1289; FAK Y576/Y577; SHC Y317; STAT5 Y694; ERBB2 Y877; ERBB4 Y1284; MET Y1234-Y1235; ROS Y2274; RET Y905), or combinations thereof. For example, the therapeutic agent may be a TKI that targets EGFR and HER2, including, but not limited to, neratinib, affatinib, lapatinib and other known pan-HER or pan-EGFR inhibitors. Measurements may be made by protein detection methods including but not limited to, RPPA, immunohistochemistry, ELISA, suspension bead array, mass spectrometry, dot blot, or western blot.

In an aspect, a method of treating cancer in a subject comprising administering an effective amount of a TKI that targets EGFR and HER2, wherein the subject has been identified as having an elevated or decreased level (amount) of proteins of one or more biomarkers in a pre-treatment tumor sample comprising cancer cells obtained from the subject, comprises measurement of proteins of one or more biomarkers comprising ALK.Y1586; Cyclin.B1. total; Cyclin.D1.PI3K.p85.Y458.p55.Y199; EGFR.Y1068; EGFR.Y1173; EGFR.Y992; eIF4G.S1108; ERBB2 total; ERBB2.Y1248; ERBB4.Y1284; RET.Y905; SHC.Y317; ERBB2.Y877; mTOR total; HER total; or RTK total; or combinations thereof. For example, the therapeutic agent may be a TKI that targets EGFR and HER2, including, but not limited to, neratinib, affatinib, lapatinib and other known pan-HER or pan-EGFR inhibitors. Measurements may be made by protein detection methods including but not limited to, RPPA, immunohistochemistry, ELISA, suspension bead array, mass spectrometry, dot blot, or western blot. In an aspect, a method of treating cancer in a subject comprising administering an effective amount of one or more of TKI that targets EGFR and HER2, wherein the subject has been identified as having an elevated or decreased level (amount) of proteins of one or more biomarkers in a pre-treatment tumor sample comprising cancer cells obtained from the subject, comprises measurement of proteins of one or more biomarkers comprising Cyclin.D1.total; IGFBP5.total; or PARP.total; or combinations thereof. For example, the therapeutic agent may be a TKI that targets EGFR and HER2, including, but not limited to, neratinib, affatinib, lapatinib and other known pan-HER or pan-EGFR inhibitors. Measurements may be made by protein detection methods including but not limited to, RPPA, immunohistochemistry, ELISA, suspension bead array, mass spectrometry, dot blot, or western blot. In an aspect, a method of treating cancer in a subject comprising administering an effective amount of one or more of a TKI that targets EGFR and HER2, wherein the subject has been identified as having an elevated or decreased level (amount) of proteins of one or more biomarkers in a pre-treatment tumor sample comprising cancer cells obtained from the subject, comprises measurement of proteins of one or more biomarkers comprising mTOR pathway activation.score; HER Family pathway activation score; RTK pathway activation score; ALK.Y1586; EGFR.Y992; p70S6K.T412, or Cyclin.B1.total; or combinations thereof. For example, the therapeutic agent may be a TKI that targets EGFR and HER2, including, but not limited to, neratinib, affatinib, lapatinib and other known pan-HER or pan-EGFR inhibitors. Measurements may be made by protein detection methods including but not limited to, RPPA, immunohistochemistry, ELISA, suspension bead array, mass spectrometry, dot blot, or western blot. In an aspect, a method of treating cancer in a subject comprising administering an effective amount of one or more of a TKI that targets EGFR and HER2, wherein the subject has been identified as having an elevated or decreased level (amount) of proteins of one or more biomarkers in a pre-treatment tumor sample comprising cancer cells obtained from the subject, comprises measurement of proteins of one or more biomarkers comprising AKT S473; AKT T308; EGFR; EGFR Y1068; EGFR Y1148; EGFR Y1173; EGFR Y992; ERBB2; ERBB2 Y1248; ERBB3; ERBB3 Y1289; ERK1/2 T202/Y204; Heregulin; mTOR; mTOR S2448; PI3K p85 Y458/p55 Y199; PTEN S380; or SHC Y317; or combinations thereof. For example, the therapeutic agent may be a TKI that targets EGFR and HER2, including, but not limited to, neratinib, affatinib, lapatinib and other known pan-HER or pan-EGFR inhibitors. Measurements may be made by protein detection methods including but not limited to, RPPA, immunohistochemistry, ELISA, suspension bead array, mass spectrometry, dot blot, or western blot. In an aspect, a method of treating cancer in a subject comprising administering an effective amount of one or more of a TKI that targets EGFR and HER2, wherein the subject has been identified as having an elevated or decreased level (amount) of proteins of one or more biomarkers in a pre-treatment tumor sample comprising cancer cells obtained from the subject, comprises measurement of proteins of one or more biomarkers comprising EGFR Y1068; EGFR Y1173; EGFR Y992; ERBB2 total; ERBB2 Y1248; ERBB3 Y1289; SHC Y317; or combinations thereof. For example, the therapeutic agent may be a TKI that targets EGFR and HER2, including, but not limited to, neratinib, affatinib, lapatinib and other known pan-HER or pan-EGFR inhibitors. Measurements may be made by protein detection methods including but not limited to, RPPA, immunohistochemistry, ELISA, suspension bead array, mass spectrometry, dot blot, or western blot. In an aspect, a method of treating cancer in a subject comprising administering an effective amount of one or more of a TKI that targets EGFR and HER2, wherein the subject has been identified as having an elevated or decreased level (amount) of proteins of one or more biomarkers in a pre-treatment tumor sample comprising cancer cells obtained from the subject, comprises measurement of proteins of one or more biomarkers comprising IGFBP5.total. For example, the therapeutic agent may be a TKI that targets EGFR and HER2, including, but not limited to, neratinib, affatinib, lapatinib and other known pan-HER or pan-EGFR inhibitors. Measurements may be made by protein detection methods including but not limited to, RPPA, immunohistochemistry, ELISA, suspension bead array, mass spectrometry, dot blot, or western blot. In an aspect, a method of treating cancer in a subject comprising administering an effective amount of one or more of a TKI that targets EGFR and HER2, wherein the subject has been identified as having an elevated or decreased level (amount) of proteins of one or more biomarkers in a pre-treatment tumor sample comprising cancer cells obtained from the subject, comprises measurement of proteins of one or more biomarkers comprising EGFR.Y1173; ERBB2.Y1248; ERBB4.Y1284; PDGFRa.Y754; or RTK.ROR1.total; or combinations thereof. For example, the therapeutic agent may be a TKI that targets EGFR and HER2, including, but not limited to, neratinib, affatinib, lapatinib and other known pan-HER or pan-EGFR inhibitors. Measurements may be made by protein detection methods including but not limited to, RPPA, immunohistochemistry, ELISA, suspension bead array, mass spectrometry, dot blot, or western blot. In an aspect, a method of treating cancer in a subject comprising administering an effective amount of one or more of a TKI that targets EGFR and HER2, wherein the subject has been identified as having an elevated or decreased level (amount) of proteins of one or more biomarkers in a pre-treatment tumor sample comprising cancer cells obtained from the subject, comprises measurement of proteins of one or more biomarkers comprising A.RAF.S299; LC3B.total; or TIE2.Y992; or combinations thereof. For example, the therapeutic agent may be a TKI that targets EGFR and HER2, including, but not limited to, neratinib, affatinib, lapatinib and other known pan-HER or pan-EGFR inhibitors. Measurements may be made by protein detection methods including but not limited to, RPPA, immunohistochemistry, ELISA, suspension bead array, mass spectrometry, dot blot, or western blot.

Disclosed are methods of treating cancer in a subject comprising, a) measuring in a pre-treatment tumor sample comprising cancer cells from a subject, protein levels of one or more biomarkers disclosed herein, b) comparing the measured protein levels of the one or more biomarkers from the subjects to a baseline value for the respective protein levels of the one or more biomarkers, wherein the one or more biomarkers comprise ALK.Y1586; ALK.Y1604; AMPKb1.S108; Caspase.7, cleaved D198; Cyclin.B1 total; Cyclin.D1.total; EGFR.Y1068, EGFR.Y1173, EGFR.Y992, eIF4G.S1108; IGFBP5.total; ERBB2.total; ERBB2.Y1248; ERBB2.Y877; ERBB3.Y1289; ERBB4.Y1284; FAK.Y576.Y577; JAK1.Y1022 and Y1023; JAK2.Y1007; MEK1.2.S217 and S211; MET.Y1234 and Y1235; p70S6K.T389; p70S6K.T412; PI3K.p85.Y458.p55. and Y199; AKT S473; AKT T308; EGFR total; EGFR Y1148; ERBB3 total; ERK1/2 T202/Y204; Heregulin total; mTOR S2448; mTOR total; PTEN S380; SHC Y317; PARP.total; PDGFRa.Y754; RET.Y905; RTK.ROR1.total; SHC.Y317; STAT5.Y694; VEGFR2.Y996; X4EBP1.S65; AMPKa1.S485; A.RAF.S299; IGF1R.Y1131. and IR.Y1146; MCSFR.Y732; A.RAF.S299; LC3B.total; TIE2.Y992; a JAK.STAT.pathway score (which is the sum of the measurements for JAK1 Y1022/Y1023, JAK1 Y1007, STAT1 Y701 STAT2Y727, STAT3 Y705, STAT5 Y694), a mTOR pathway score (which is the sum of the measurements for 4EBP1 S65; eIF4E S209; eIF4G S1108; eIF4G S1108; eIF4G S1108; mTOR S2448; p70S6K S371; p70S6K T389; p70S6K T412; S6RP S240/S244); a HER Family pathway score (which is the sum of the measurements for EGFR Y1068; EGFR Y1173; EGFR Y992; ERBB2 Y1248; ERBB3 Y1289; FAK Y576/Y577; SHC Y317; STAT5 Y694; RET Y905); and a RTK pathway score (which is the sum of the measurements for ALK Y1604; EGFR Y1068; EGFR Y1173; EGFR Y992; ERBB2 Y1248; ERBB3 Y1289; FAK Y576/Y577; SHC Y317; STAT5 Y694; ERBB2 Y877; ERBB4 Y1284; MET Y1234-Y1235; ROS Y2274; RET Y905), or combinations thereof, wherein an elevated or decreased level of the one or more biomarkers indicates that the subject is a responder to a therapeutic agent and has an increased likelihood of tumor shrinkage after treatment with the therapeutic agent. In an aspect, a method may further comprise administering to the subject an effective amount of the therapeutic agent. For example, the therapeutic agent may be a TKI that targets EGFR and HER2, including, but not limited to, neratinib, affatinib, lapatinib and other known pan-HER or pan-EGFR inhibitors. Measurements may be made by protein detection methods including but not limited to, RPPA, immunohistochemistry, ELISA, suspension bead array, mass spectrometry, dot blot, or western blot.

In an aspect, a method of treating cancer in a subject comprising, a) measuring in a pre-treatment tumor sample comprising cancer cells from a subject, protein levels of one or more biomarkers disclosed herein, b) comparing the measured protein levels of the one or more biomarkers from the subjects to a baseline value for the respective protein levels of the one or more biomarkers, wherein the one or more biomarkers comprise ALK.Y1586; Cyclin.B1. total; Cyclin.D1.PI3K.p85.Y458.p55.Y199; EGFR.Y1068; EGFR.Y1173; EGFR.Y992; eIF4G.S1108; ERBB2 total; ERBB2.Y1248; ERBB4.Y1284; RET.Y905; SHC.Y317; ERBB2.Y877; mTOR total; HER total; or RTK total; or combinations thereof, and further comprising administering an effective amount of one of more TKIs that target EGFR and HER2, including, but not limited to, neratinib, affatinib, lapatinib and other known pan-HER or pan-EGFR inhibitors. Measurements may be made by protein detection methods including but not limited to, RPPA, immunohistochemistry, ELISA, suspension bead array, mass spectrometry, dot blot, or western blot. In an aspect, a method of treating cancer in a subject comprising, a) measuring in a pre-treatment tumor sample comprising cancer cells from a subject, protein levels of one or more biomarkers disclosed herein, b) comparing the measured protein levels of the one or more biomarkers from the subjects to a baseline value for the respective protein levels of the one or more biomarkers, wherein the one or more biomarkers comprise Cyclin.D1.total; IGFBP5.total; or PARP.total; or combinations thereof; and further comprising administering an effective amount of one of more TKIs that target EGFR and HER2, including, but not limited to, neratinib, affatinib, lapatinib and other known pan-HER or pan-EGFR inhibitors. Measurements may be made by R protein detection methods including but not limited to, RPPA, immunohistochemistry, ELISA, suspension bead array, mass spectrometry, dot blot, or western blot. In an aspect, a method of treating cancer in a subject comprising, a) measuring in a pre-treatment tumor sample comprising cancer cells from a subject, protein levels of one or more biomarkers disclosed herein, b) comparing the measured protein levels of the one or more biomarkers from the subjects to a baseline value for the respective protein levels of the one or more biomarkers, wherein the one or more biomarkers comprise mTOR pathway activation.score; HER Family pathway activation score; RTK pathway activation score; ALK.Y1586; EGFR.Y992; p70S6K.T412, or Cyclin.B1.total; or combinations thereof, and further comprising administering an effective amount of one of more TKIs that target EGFR and HER2, including, but not limited to, neratinib, affatinib, lapatinib and other known pan-HER or pan-EGFR inhibitors. Measurements may be made by protein detection methods including but not limited to, RPPA, immunohistochemistry, ELISA, suspension bead array, mass spectrometry, dot blot, or western blot. In an aspect, a method of treating cancer in a subject comprising, a) measuring in a pre-treatment tumor sample comprising cancer cells from a subject, protein levels of one or more biomarkers disclosed herein, b) comparing the measured protein levels of the one or more biomarkers from the subjects to a baseline value for the respective protein levels of the one or more biomarkers, wherein the one or more biomarkers comprise AKT S473; AKT T308; EGFR; EGFR Y1068; EGFR Y1148; EGFR Y1173; EGFR Y992; ERBB2; ERBB2 Y1248; ERBB3; ERBB3 Y1289; ERK1/2 T202/Y204; Heregulin; mTOR; mTOR S2448; PI3K p85 Y458/p55 Y199; PTEN S380; or SHC Y317; or combinations thereof, and further comprising administering an effective amount of one of more TKIs that target EGFR and HER2, including, but not limited to, neratinib, affatinib, lapatinib and other known pan-HER or pan-EGFR inhibitors. Measurements may be made by protein detection methods including but not limited to, RPPA, immunohistochemistry, ELISA, suspension bead array, mass spectrometry, dot blot, or western blot. In an aspect, a method of treating cancer in a subject comprising, a) measuring in a pre-treatment tumor sample comprising cancer cells from a subject, protein levels of one or more biomarkers disclosed herein, b) comparing the measured protein levels of the one or more biomarkers from the subjects to a baseline value for the respective protein levels of the one or more biomarkers, wherein the one or more biomarkers comprise EGFR Y1068; EGFR Y1173; EGFR Y992; ERBB2 total; ERBB2 Y1248; ERBB3 Y1289; SHC Y317; or combinations thereof, and further comprising administering an effective amount of one of more TKIs that target EGFR and HER2, including, but not limited to, neratinib, affatinib, lapatinib and other known pan-HER or pan-EGFR inhibitors. Measurements may be made by protein detection methods including but not limited to, RPPA, immunohistochemistry, ELISA, suspension bead array, mass spectrometry, dot blot, or western blot. In an aspect, a method of treating cancer in a subject comprising, a) measuring in a pre-treatment tumor sample comprising cancer cells from a subject, protein levels of one or more biomarkers disclosed herein, b) comparing the measured protein levels of the one or more biomarkers from the subjects to a baseline value for the respective protein levels of the one or more biomarkers, wherein the one or more biomarkers comprise IGFBP5 total, and further comprising administering an effective amount of one of more TKIs that target EGFR and HER2, including, but not limited to, neratinib, affatinib, lapatinib and other known pan-HER or pan-EGFR inhibitors. Measurements may be made by protein detection methods including but not limited to, RPPA, immunohistochemistry, ELISA, suspension bead array, mass spectrometry, dot blot, or western blot. In an aspect, a method of treating cancer in a subject comprising, a) measuring in a pre-treatment tumor sample comprising cancer cells from a subject, protein levels of one or more biomarkers disclosed herein, b) comparing the measured protein levels of the one or more biomarkers from the subjects to a baseline value for the respective protein levels of the one or more biomarkers, wherein the one or more biomarkers comprise EGFR.Y1173; ERBB2.Y1248; ERBB4.Y1284; PDGFRa.Y754; or RTK.ROR1.total; or combinations thereof, and further comprising administering an effective amount of one of more TKIs that target EGFR and HER2, including, but not limited to, neratinib, affatinib, lapatinib and other known pan-HER or pan-EGFR inhibitors. Measurements may be made by protein detection methods including but not limited to, RPPA, immunohistochemistry, ELISA, suspension bead array, mass spectrometry, dot blot, or western blot. In an aspect, a method of treating cancer in a subject comprising, a) measuring in a pre-treatment tumor sample comprising cancer cells from a subject, protein levels of one or more biomarkers disclosed herein, b) comparing the measured protein levels of the one or more biomarkers from the subjects to a baseline value for the respective protein levels of the one or more biomarkers, wherein the one or more biomarkers comprise A.RAF.S299; LC3B.total; or TIE2.Y992; or combinations thereof, and further comprising administering an effective amount of one of more TKIs that target EGFR and HER2, including, but not limited to, neratinib, affatinib, lapatinib and other known pan-HER or pan-EGFR inhibitors. Measurements may be made by protein detection methods including but not limited to, RPPA, immunohistochemistry, ELISA, suspension bead array, mass spectrometry, dot blot, or western blot. Such methods comprise wherein an elevated or decreased level of the one or more biomarkers indicates that the subject is a responder to a therapeutic agent and has an increased likelihood of tumor shrinkage after treatment with the therapeutic agent. The method may further comprise administering to the subject an effective amount of the therapeutic agent. For example, the therapeutic agent may be a TKI that targets EGFR and HER2, including, but not limited to, neratinib, affatinib, lapatinib and other known pan-HER or pan-EGFR inhibitors.

While data are specifically presented for predicting or assessing tumor shrinkage in breast cancer patients treated with neratinib, the phosphoproteins identified as predictive markers are ubiquitously found in every tumor type including lung, colon, gastric, rectal, ovarian, pancreatic, prostate, brain, melanomas, sarcomas, etc as well as leukemias, myelomoas and lymphomas. Given the recent findings that drug efficacy transcends tumor type or cancer type, but is based on underpinning drug target expression (eg. HER2 therapy success for HER2+/mutated lung, gastric and prostate cancers), it would be rational to expect the markers described herein would be useful for predicting or assessing response in these other tumor types. Moreover, it would be reasonable to expect that these specific predictive phosphoproteins would be predictive for tumor shrinkage and clinical response for therapeutics that have similar mechanisms of action such as Gilotrif™ (affatinib) and Tykerb™ (lapatinib).

Data presented herein demonstrate that the measurement of specific phosphorylation sites such as Y1173 and Y1068 on EGFR were predictive of neratinib response, given the coincident phosphorylation events driven by kinase-substrate interactions and domain based (e.g. SH2-SH3) protein-protein interactions, one could reasonably expect that other protein phosphorylation sites on the proteins described herein would be predictive for treatment response/tumor shrinkage.

For example, with some phenotypes or no particular phenotype, particular biomarker(s) were found to be useful in treating subjects and in predicting or assessing outcome (pCR). The following protein/phosphoproteins levels for biomarkers were statistically significantly ($p<0.05$) higher in ALL patients (without pre-selection by HER2/HR testing) who received neratinib and achieved pCR versus those who did not, and were not different between response groups in the control arm of the trial: ALK.Y1586; Cyclin.B1. total; Cyclin.D1.PI3K.p85.Y458.p55.Y199; EGFR.Y1068; EGFR.Y1173; EGFR.Y992; eIF4G.S1108; ERBB2 total; ERBB2.Y1248; ERBB4.Y1284; RET.Y905; SHC.Y317; ERBB2.Y877; mTOR total; HER total; or RTK total; or combinations thereof.

The following proteins/phosphoproteins for biomarkers were statistically significantly ($p<0.05$) lower in ALL patients (without pre-selection by HER2/HR testing) who received neratinib and achieved pCR versus those who did not and were not different between response groups in the control arm of the trial: Cyclin.D1.total; IGFBP5.total; or PARP.total; or combinations thereof.

The following proteins/phosphoprotein levels for biomarkers were statistically significantly ($p<0.05$) higher in all HER2+ patients who received neratinib without pre-selection by HR testing and achieved pCR vs those who didn't, and were not different between response groups in patients who did not receive the drug: mTOR pathway activation-.score; HER Family pathway activation score; RTK pathway activation score; ALK.Y1586; EGFR.Y992; p70S6K.T412, or Cyclin.B1.total; or combinations thereof. The following proteins/phosphoprotein levels were statistically significantly ($p<0.05$) higher in all HER2+/HR+ patients who received neratinib and achieved pCR versus those who did not, and not different between response groups in patients who did not receive the drug: ALK.Y1586; ALK.Y1604; AMPKb1.S108; Caspase.7, cleaved D198; Cyclin.B1 total; Cyclin.D1.total; EGFR.Y1068, EGFR.Y1173, EGFR.Y992; eIF4G. S1108; IGFBP5.total; ERBB2.total; ERBB2.Y1248; ERBB2.Y877; ERBB3.Y1289; ERBB4.Y1284; FAK.Y576.Y577; JAK1.Y1022 and Y1023; JAK2.Y1007; MEK1.2.S217 and S211; MET.Y1234 and Y1235; p70S6K.T389; p70S6K.T412; PI3K.p85.Y458.p55. and Y199; AKT S473; AKT T308; EGFR total; EGFR Y1148; ERBB3 total; ERK1/2 T202/Y204; Heregulin total; mTOR S2448; mTOR total; PTEN S380; SHC Y317; PARP.total; PDGFRa.Y754; RET.Y905; RTK.ROR1.total; SHC.Y317; STAT5.Y694; VEGFR2.Y996; X4EBP1.S65; AMPKa1.S485; A.RAF.S299; IGF1R.Y1131. and IR.Y1146; MCSFR.Y732; A.RAF.S299; LC3B.total; TIE2.Y992; a JAK.STAT.pathway score (which is the sum of the measurements for JAK1 Y1022/Y1023, JAK1 Y1007, STAT1 Y701 STAT2Y727, STAT3 Y705, STAT5 Y694), a mTOR pathway score (which is the sum of the measurements for 4EBP1 S65; eIF4E S209; eIF4G S1108; eIF4G S1108; eIF4G S1108; mTOR S2448; p70S6K S371; p70S6K T389; p70S6K T412; S6RP S240/S244); a HER Family pathway score (which is the sum of the measurements for EGFR Y1068; EGFR Y1173; EGFR Y992; ERBB2 Y1248; ERBB3 Y1289; FAK Y576/Y577; SHC Y317; STAT5 Y694; RET Y905); and a RTK pathway score (which is the sum of the measurements for ALK Y1604; EGFR Y1068; EGFR Y1173; EGFR Y992; ERBB2 Y1248; ERBB3 Y1289; FAK Y576/Y577; SHC Y317; STAT5 Y694; ERBB2 Y877; ERBB4 Y1284; MET Y1234-Y1235; ROS Y2274; RET Y905), or combinations thereof. The following protein for the biomarker was lower in HER2+/HR+ patients who received neratinib and achieved pCR and not between response groups in patients who did not receive neratinib: IGFBP5.total. The following proteins/phosphoproteins for biomarkers were statistically significantly ($p<0.05$) activated/over-expressed in all HER2-/HR- patients who received neratinib and achieved pCR and not between response groups in patients who did not receive the drug: EGFR.Y1173; ERBB2.Y1248; ERBB4.Y1284; PDGFRa.Y754; or RTK.ROR1.total; or combinations thereof. The following proteins/phosphoproteins for biomarkers were statistically significantly ($p<0.05$) lower in HER2-/HR- patients who received neratinib and achieved pCR and were not different between response groups in patients who did not receive the drug: A.RAF.S299; LC3B.total; or TIE2.Y992; or combinations thereof.

In methods described herein, administration or delivery of the therapeutic agents to cells can be via one or more modes of administration or formulations. For example, the therapeutic agent can be formulated as a pharmaceutical composition. Additionally, dosing regimens and dose amounts can be determined by methods known to those of skill in the art. Pharmaceutical compositions can be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration can include ointments, lotions, creams, gels, drops, suppositories, sprays, liquids and powders. Conventional pharmaceutical carriers, aqueous, powder or oily bases, thickeners and the like may be necessary or desirable. Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Methods disclosed herein comprise detection of proteins of biomarkers disclosed herein. The detection methods used may include reverse phase microarray analysis, or any other methods known for protein detection known to those skilled in the art.

While the reverse phase protein microarray (RPPA) technology was used as a discovery platform that uncovered predictive biomarkers disclosed herein and methods to better select and treat patients for neratinib treatment, there are a number of proteomic technologies that could be used to measure the specific markers for clinical implementation. Such technologies include, but are not limited to, suspension bead arrays, immunohistochemistry, mass cytometry, mass spectrometry, ELISA, western blotting, etc. Detection methods could be colorimetric, florescent, chemiluminescent, electrochemical or any routinely used means of measuring proteins from a tissue sample. Use of detection methods are within the knowledge of those of skill in the art.

An aspect of the invention is a kit for predicting or assessing a subject's response to a therapeutic agent and/or the subject's prognosis or prediction of tumor shrinkage, comprising one or more agents for measuring the level of protein of one or more biomarkers disclosed herein. The agents can be, e.g., antibodies specific for phosphorylated or non-phosphorylated forms of the proteins. The kit may include agents suitable for a label or label-free method known in the art to measure protein levels of one or more biomarkers disclosed herein, such as agents for using mass spectrometry or electrophoretic mobility. Biomarkers may comprise one or more of ALK.Y1586; ALK.Y1604; AMPKb1.S108; Caspase.7, cleaved D198; Cyclin.B1 total; Cyclin.D1.total; EGFR.Y1068, EGFR.Y1173, EGFR.Y992, eIF4G.S1108; IGFBP5.total; ERBB2.total; ERBB2.Y1248; ERBB2.Y877; ERBB3.Y1289; ERBB4.Y1284; FAK.Y576.Y577; JAK1.Y1022 and Y1023; JAK2.Y1007; MEK1.2.S217 and S211; MET.Y1234 and Y1235; p70S6K.T389; p70S6K.T412; PI3K.p85.Y458.p55. and Y199; AKT S473; AKT T308; EGFR total; EGFR Y1148; ERBB3 total; ERK1/2 T202/Y204; Heregulin total; mTOR S2448; mTOR total; PTEN S380; SHC Y317; PARP.total; PDGFRa.Y754; RET.Y905; RTK.ROR1.total; SHC.Y317; STAT5.Y694; VEGFR2.Y996; X4EBP1.S65; AMPKa1.S485; A.RAF.S299; IGF1R.Y1131. and IR.Y1146; MCSFR.Y732; A.RAF.S299; LC3B.total; TIE2.Y992; a JAK.STAT.pathway score (which is the sum of the measurements for JAK1 Y1022/Y1023, JAK1 Y1007, STAT1 Y701 STAT2Y727, STAT3 Y705, STAT5 Y694), a mTOR pathway score (which is the sum of the measurements for 4EBP1 S65; eIF4E S209; eIF4G S1108; eIF4G S1108; eIF4G S1108; mTOR S2448; p70S6K S371; p70S6K T389; p70S6K T412; S6RP S240/S244); a HER Family pathway score (which is the sum of the measurements for EGFR Y1068; EGFR Y1173; EGFR Y992; ERBB2 Y1248; ERBB3 Y1289; FAK Y576/Y577; SHC Y317; STAT5 Y694; RET Y905); and a RTK pathway score (which is the sum of the measurements for ALK Y1604; EGFR Y1068; EGFR Y1173; EGFR Y992; ERBB2 Y1248; ERBB3 Y1289; FAK Y576/Y577; SHC Y317; STAT5 Y694; ERBB2 Y877; ERBB4 Y1284; MET Y1234-Y1235; ROS Y2274; RET Y905), or combinations thereof.

An aspect of the invention is a pharmaceutical composition, or a kit for treating a subject in need thereof, comprising a TKI that targets EGFR and HER2. Pharmaceutical compositions comprise a pharmaceutically acceptable carrier. The pharmaceutical agent or kit may further comprise a chemotherapeutic agent that can be administered in conjunction with the that targets EGFR and HER2. Such kits disclosed may be combined so as to provide the pharmaceutical composition and agents for detecting the desired biomarkers.

Definitions

It must be noted that as used herein and in the appended claims, the singular forms "a", "an", and "the" include plural reference unless the context clearly dictates otherwise. Thus, for example, reference to "a therapeutic" includes a plurality of such therapeutics, reference to "the breast" is a reference to one or more breast cancer associated complications known to those skilled in the art, and so forth.

The term "dose" refers to the quantity or amount of a composition taken, administered, or recommended to be taken or administered at or over a particular time. The time can be per administration or per day. For example, a dose of a therapeutic can be, but is not limited to, a specific amount of a composition, such as an immunosuppressant, administered 2× a day. A dose can also be a specific amount of a composition administered every day for 2 weeks.

As used herein, "cancer" is meant to mean any of many diseases characterized by the presence of cancerous tissue in a subject. As used herein, "cancerous tissue" is meant to mean a tissue that comprises malignant neoplastic cells, exhibits an abnormal growth of cells and/or hyperproliferative cells. Cancerous tissue can be a primary malignant tumor, arising in a tissue or organ of origin, or it can be a metastatic malignant tumor, growing in a body tissue which was not the source of the original tumor. Thus, malignant neoplastic cells can invade and destroy nearby tissue and spread to other parts of the body (metastasize). As used herein, the term "neoplastic" means an abnormal growth of a cell or tissue (e.g., a tumor or non-solid hyper proliferative cellular activity) which may be benign or malignant (cancerous). As used herein, "abnormal growth of cells" and/or "hyperproliferative cells" are meant to refer to cell growth independent of normal regulatory mechanisms (e.g., loss of contact inhibition), including the abnormal growth of benign and malignant cells or other neoplastic diseases. As used herein, the term "tumor" includes neoplasms that are identifiable through clinical screening or diagnostic procedures including, but not limited to, palpation, biopsy, cell proliferation index, endoscopy, ultrasonography, computed tomography (CT), magnetic resonance imaging (MRI), positron emission tomography (PET), radiography, radionuclide evaluation, CT- or MRI-guided aspiration cytology, and imaging-guided needle biopsy, among others. Such diagnostic techniques are well known to those skilled in the art and are described in Holland, et al., Cancer Medicine, 4th Ed., Vol. One, Williams & Wilkins, Baltimore, Md. (1997).

A "breast cancer" is a cancer that occurs in the breast of a subject. Breast cancer is a tumor (that may be malignant) that starts in the cells of the breast. A malignant tumor is a group of cancer cells that can grow into (invade) surrounding tissues or spread (metastasize) to distant areas of the body. The disease occurs almost entirely in women, but men can get it, too. Examples of breast cancer include, but are not limited to, invasive ductal carcinoma, invasive lobular carcinoma, ductal carcinoma in situ, and lobular carcinoma in situ.

The term "efficacy" refers to the ability to produce a desired or intended result. For example, the efficacy of a therapeutic is the ability of the therapeutic to produce the intended result, such as treat a particular disease. Efficacy can be determined by evaluating laboratory tests, imaging results, signs and symptoms known to be useful in evaluating the status of breast cancer. In some situations, efficacy may be determined as observation of tumor shrinkage such as with MRI, or a definitive histological/pathological determination such as "complete pathological response", or pCR or residual cancer burden levels (RCB) wherein no or little tumor is present at the time of surgery during neoadjuvant treatment.

The term "therapeutic agent" refers to a composition that treats a disease. For example, the therapeutic agents disclosed herein are compositions that treat breast cancer.

The phrase "therapeutic effect" refers to the treatment, reduction of symptoms amelioration, prevention of disease, inhibition of disease progression, or reduced severity or incidence of disease as a result of the administration of a therapeutic.

The term "treating" refers to partially or completely alleviating, ameliorating, relieving, delaying onset of, inhibiting progression of, reducing severity of, and/or reducing incidence of one or more symptoms or features of a particular disease, disorder, and/or condition. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Neratinib is an orally available low molecular weight potent irreversible tyrosine kinase inhibitor, or TKI, that blocks signal transduction through the epidermal growth factor receptors, or EGFRs, HER1, HER2 and HER4.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range ¬ from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described.

Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if neratinib is disclosed and discussed and a number of modifications that can be made to the drug are discussed, each and every combination and permutation of the drug and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A "subject," as used herein, includes any animal, mammal, including a human, that has a cancer. Suitable subjects (patients) include laboratory animals (such as mouse, rat, rabbit, or guinea pig), farm animals, and domestic animals or pets (such as a cat or dog). Non-human primates and, human patients, are included.

A "baseline value," as used herein, refers to the level or amount of the same protein(s) or phosphoprotein(s) that are the biomarker, but the level or amount of protein(s) or phosphoprotein(s) are measured in cells from tumors obtained from control subjects such as women who did not achieve pCR, or an optimized "cut-point" value determined by statistical analysis such as receiver operating curve (ROC) of a population of data derived from tumors of patients who did or did not achieve clinical success (such as pCR or tumor shrinkage), or other relevant controls. An increase in the amount of a phosphoprotein can reflect either an increase in the number of suitable amino acid residues of the protein (e.g., serines, threonines or tyrosines) that are phosphorylated, or an increased frequency of phosphorylations at a particular amino acid residue. For example, a baseline value may include reference standards, where a predetermined threshold value (or range of values) determines whether the amount of measured protein, or the phosphorylation state of the protein, is above the "normal" value. The terms threshold level, control and baseline value are used interchangeably herein. For each protein whose level (amount) is determined, the value can be normalized to the total protein in the cell; or to the amount of a constitutively expressed protein (from a housekeeping gene), such as actin. Increased amounts or decreased amounts of total protein, particular proteins or phosphorylated proteins can be determined routinely. For example, reference standards can be used, where a predetermined threshold value (or range of values) determines whether the amount of measured protein is above the "baseline" value. Such a threshold value is sometimes referred to herein as a baseline value.

REFERENCES

1. Xia W, Liu Z, Zong R, Liu L, Zhao S, Bacus S S, Mao Y, He J, Wulfkuhle J D, Petricoin E F 3rd, Osada T, Yang X Y, Hartman Z C, Clay T M, Blackwell K L, Lyerly H K, Spector N L. Truncated ErbB2 expressed in tumor cell nuclei contributes to acquired therapeutic resistance to ErbB2 kinase inhibitors. Mol Cancer Ther. 2011 Jun. 14.
2. Popova T G, Narayanan A, Lance Liotta L Petricoin E F III, Bailey C, Kehn-Hall K, and Kashanchi F Reverse-phase phosphoproteome analysis (RPPA) of signaling pathways induced by HTLV-1 infection Retrovirology 2011, 8(Suppl 1)
3. Ibarra-Drendall C, Troch M M, Barry W T, Broadwater G, Petricoin E F 3rd, Wulfkuhle J, Liotta L A, Lem S, Baker J C Jr, Ford A C, Wilke L G, Zalles C, Kuderer N M, Hoffman A W, Shivraj M, Mehta P, Williams J, Tolbert N, Lee L W, Pilie P G, Yu D, Seewaldt V L. Pilot and feasibility study: prospective proteomic profiling of mammary epithelial cells from high-risk women provides evidence of activation of pro-survival pathways. Breast Cancer Res Treat. 2011 Jun. 7.
4. Improta G, Zupa A, Fillmore H, Deng J, Aieta M, Musto P, Liotta L A, Broaddus W, Petricoin E F, Wulfkuhle J. Protein Pathway Activation Mapping of Brain Metastasis from Lung and Breast Cancers Reveals Organ Type Specific Drug Target Activation. J Proteome Res. 2011 May 16. [Epub ahead of print]
5. Anderson T, Wulfkuhle J, Petricoin E, Winslow R L. High resolution mapping of the cardiac transmural proteome using reverse phase protein microarrays. Mol Cell Proteomics. 2011 Apr. 13. [Epub ahead of print]
6. Napoletani D, Signore M, Sauer T, Liotta L, Petricoin E. Homologous control of protein signaling networks. J Theor Biol. 2011 279(1):29-43.
7. Fodale V, Pierobon M, Liotta L, Petricoin E. *Mechanism of cell adaptation: when and how do cancer cells develop chemoresistance?* Cancer J. 2011 March-April; 17(2):89-95.
8. Gallagher R I, Silvestri A, Petricoin E F 3rd, Liotta L A, Espina V. *Reverse phase protein microarrays: fluorometric and colorimetric detection.* Methods Mol Biol. 2011; 723:275-301.
9. Silvestri A, Colombatti A, Calvert V S, Deng J, Mammano E, Belluco C, De Marchi F, Nitti D, Liotta L A, Petricoin E F, Pierobon M. Protein pathway biomarker analysis of human cancer reveals requirement for upfront cellular-enrichment processing. Lab Invest. 2010 May; 90(5):787-96.
10. Anderson T, Wulfkuhle J, Liotta L, Winslow R L, Petricoin E 3rd. Improved reproducibility of reverse phase protein microarrays using array microenvironment normalization Proteomics. 2009 December; 9(24):5562-6.
11. Pierobon M, Calvert V, Belluco C, Garaci E, Deng J, Lise M, Nitti D, Mammano E, Marchi F D, Liotta L, Petricoin E. Multiplexed Cell Signaling Analysis of Metastatic and Nonmetastatic Colorectal Cancer Reveals COX2-EGFR Signaling Activation as a Potential Prognostic Pathway Biomarker. Clin Colorectal Cancer. 2009 April; 8(2):110-7.
12. Wulfkuhle J D, Speer R, Pierobon M, Laird J, Espina V, Deng Jm Mammano E, Yang S X, Swain S M, Nitti D, Esserman L J, Belluco C, Liotta L A and Petricoin E F. Multiplexed Cell Signaling Analysis of Human Breast Cancer: Applications for Personalized Therapy. J of Prot Res. 2008 April; 7(4):1508-17.
13. Zhou, J, Wulfkuhle J, Zhang H, Gu P, Yang Y, Deng J, Margolick J B, Liotta L A, Petricoin E F, Zhang Y. Activation of the PTEN/mTOR/STAT3 pathway in breast cancer stem-like cells is required for viability and maintenance. PNAS 2007. Oct. 9; 104(41):16158-63.
14. VanMeter A, Signore M, Pierobon M, Espina V, Liotta L A, Petricoin E F Reverse-phase protein microarrays: application to biomarker discovery and translational medicine Expert Review of Molecular Diagnostics. 2007. 7(5): 625-633(9).
15. Rapkiewicz A, Espina V, Zujewski J A, Lebowitz P F, Filie A, Wulfkuhle J, Camphausen K, Petricoin E F 3rd, Liotta L A, Abati A. The needle in the haystack: Application of breast fine-needle aspirate samples to quantitative protein microarray technology. Cancer. 2007 Jun. 25; 111(3):173-84.

EXAMPLES

Example 1

Evaluation of HER Family Protein Signaling Network as a Predictive Biomarker for pCR for Breast Cancer Patients Treated with Neratinib in the I-SPY 2 TRIAL Adaptive design trials are constructed on the basis of assigning patients to certain signature groups such as signature biomarker groups, the goal being to determine predictive probabilities of success in Phase III trials for various targeted therapeutics. In essence, the design trials provide data that facilitates the determination of which patient biomarker signatures respond to various regimens. A regimen would "graduate" from trial if probability of statistical significance in Phase III reaches 85% for any signature, provided that a minimum of 60 patients have been assigned to the regimen. Neratinib was one of 7 agents tested in the experimental arms of the ISPY-2 TRIAL to date.

This example tested the hypothesis that the response to the pan-ERBB inhibitor, neratinib, was predicted by pre-treatment HER2-EGFR signaling. In the I-SPY 2 TRIAL, neratinib graduated in the HR−/HER2+ signature. All patients received at least standard chemotherapy (which was comprised of 12 weekly cycles of paclitaxel (a taxane) therapy followed by 4 cycles of doxorubicin/cyclophosph-amide (AC) therapy). For HER2+ patients, neratinib was administered in place of trastuzumab, and all HER2+ control arm patients received chemotherapy plus trastuzumab. 18 HER family signaling proteins were evaluated as biomarkers of neratinib response using reverse phase protein microarray (RPMA) data from pre-treatment laser capture microdissection (LCM) purified tumor epithelium. Reverse phase protein microarray (RPPA) was used to quantitatively measure the level of proteins and phosphorylated proteins in the pretreatment biopsy specimens of women with Stage breast cancer who have a high risk of recurrence and who were treated with neratinib+chemotherapy vs women who were treated with chemotherapy alone.

One hundred sixty-eight (168) patients (neratinib: 106, concurrent controls: 62) had RPMA and pathological complete response (pCR) data. Eighteen (18) protein/phospho-proteins biomarkers relating to HER family signaling were evaluated: AKT S473, AKT T308, EGFR, EGFR Y1068, EGFR Y1148, EGFR Y1173, EGFR Y992, ERBB2, ERBB2 Y1248, ERBB3 total, ERBB3 Y1289, ERK1/2 T202/Y204, Heregulin, mTOR, mTOR S2448, PI3K p85 Y458/p55 Y199, PTEN S380, and SHC Y317. This study assessed association between biomarker and response in the neratinib and control arms alone (likelihood ratio test), and relative performance between arms (biomarker×treatment interaction) using a logistic model. Analysis was also performed adjusting for HR/HER2 status. In an exploratory analysis, the marker with the greatest interaction (phosphorylated EGFR (Y1173)) was selected to dichotomize patients optimally based on the data and assessed it in the context of the graduating signature by adding the EGFR Y1173-High patients to the HR−/HER2+ subtype and evaluating the treatment effect in this 'biomarker-positive' group. Statistical calculations are descriptive (e.g. p-values are measures of distance with no inferential content).

Methods

ISPY-2 TRIAL pre-treatment biopsy specimens were subjected to LCM to procure tumor epithelium for reverse phase protein microarray (RPPA analysis). Approximately 10,000 cells were captured for each of 168 samples in the neratinib treatment and concurrent control arms. (107 N treatment arm, 64 control samples).

RPPA data was collected for 18 qualifying biomarker proteins/phosphoproteins related to HER family signaling: AKT S473, AKT T308, EGFR, EGFR Y1068, EGFR Y1148, EGFR Y1173, EGFR Y992, ERBB2, ERBB2 Y1248, ERBB3, ERBB3 Y1289, ERK1/2 T202/Y204, Heregulin, mTOR, mTOR S2448, PI3K p85 Y458/p55 Y199, PTEN S380, and SHC Y317.

Reverse-phase Protein Microarray Construction

A full description of the technology and associated methodology is discussed in Example 3. Briefly, lysates (approx 40 microliters) from LCM procured cells or cell culture were loaded into 384-well plates in serial dilutions (neat, 1:2, 1:4, 1:8 and 1:16) with negative control wells containing lysis buffer only. Each dilution series was printed in triplicate onto nitrocellulose-coated glass slides (Schleicher and Schuell Bioscience, Keene, N.H., USA) using a custom solid pin contact arrayer (Aushon 2470, Aushon Biosystems, Boston Mass.). In order to bridge between slides and for quantitation, controls and calibrators were printed on every slide. These consisted of lysates from A431 cell lines (+/−EGF stimulation, Hela+/−pervanadate, Jurkat+/−calyculin, Jurkat+/−Fas ligand; BD Pharmingen, San Diego, Calif.,). All phosphorylation and protein endpoints from the RPPA were normalized to total protein. This was performed by staining with Sypro Ruby Protein Blot Stain (Molecular Probes, Eugene, Oreg., USA) on one representative slide from each array run. This technique The slides were analyzed using a NovaRay™ Imaging System (Alpha Innotech, San Leandro, Calif.).

Reverse Phase Protein Microarray Data Analysis

Values obtained by the measurement of laser capture microdissected tumor epithelium using the reverse phase protein microarray technology quantitatively measured the activation/phosphorylation level as well as the total protein level of hundreds of signaling proteins at once. Values were obtained by comparison of values obtained from each patient tumor sample compared to calibrators that are printed on the same array so that a patient value was calculated and determined by a mathematical transformation to a relative intensity value if using reference standards (reference units or RU) or specific amounts of an analyte were used to make up the calibration curve to generate specific amounts or concentrations (e.g. micrograms or micrograms/milliliter).

Laser Capture Microdissection (LCM)

LCM was performed in order to obtain pure populations of input material for cell signaling analysis. Using LCM (Pixcell II, Arcturus Bioscience, Mountain View, Calif.), approximately 20,000 cells (approx 5000 laser shots) were obtained from tumor epithelium derived from separate alternate and concurrent cryostat sections. Tissue processing and preparation of tissue lysates have been described in the literature.

Immunostaining.

RPPA were immunostained on an automated slide stainer (Dako, Carpinteria, Calif.) using a biotinyl-linked catalyzed signal amplification system (CSA, DAKO) and a near-infrared dye coupled secondary antibody for florescent detection (LICOR Biosystems, Lincoln Nebr.). All antibodies were pre-validated by Western blot and antibody concentrations were optimized using test arrays similar to those included in the study.

Image Analysis

Stained slides were scanned using a Novarray fluorescent laser scanner with cooled CCD (Alpha Innotech). The florescent images were analyzed using MicroVigene software (VigeneTech, Boston, Mass.). Briefly, a single intensity value was determined for each endpoint and each patient by mathematically determining linear dynamic range of the sample, and extrapolation of the intensity value to the calibrator. The antibody intensity was normalized to total protein and to a secondary antibody alone control, and the replicates for each case were averaged. The intensity values for each antibody and case are imported into Microsoft Excel (Microsoft, Redmond, Wash., USA).

Statistical Analyses

Logistic regression was used to assess association with pCR in the control and neratinib treated populations individually. Relative biomarker performance between arms (biomarker×treatment interaction) was assessed using a logistic model (pCR~treatment+biomarker+treatment×biomarker). Analysis was also performed adjusting for HR/HER2 status (pCR~treatment+biomarker+treatment: biomarker+HR status+HER2 status). Permutation testing was used to determine statistical significance.
Bayesian Analyses Bayesian analysis was completed using the MCMC simulation based on I-SPY 2 data with the following model: pCR~HR+HER2+biomarker+treatment+treatment*HR+ treatment*HER2+treatment*biomarker. No multiple comparison adjustments were applied. The Bayesian analytical engine developed by Don Berry (Yee et al J Clin Oncol. 2012 Dec. 20; 30(36):4584-6), is a mathematical approach that evaluates the clinical performance of a drug (in this case, neratinib) in both the treatment arm (in this case tumor shrinkage estimates by size changes observed by MRI), coupled with complete pathological response (pCR) as measured as the final response determinant, and the response of the predicate therapy in the control arm. This evaluation determined success of a given therapy for a Phase III trial, and in this case, it was determined that phosphorylation of EGFR at Y1173 was not only statistically significant at predicting or assessing response to neratinib in all patients regardless of hormone receptor levels and HER2 levels (HER2+, HER2− and HR+ and HR−), but when patients with high levels of phosphorylated EGFR (Y1173) were added to the HR−/HER2+ subgroup, the prevalence of 'biomarker-positive' patients increased by 50%, while increasing the predicted probability of Phase III success to 90%. Moreover, when EGFR Y1173 was used as a single marker, a statistically significant increase in Phase III success was determined for all patients compared to HER2+/HR− status as measured by immunohistochemical methods. (93% vs 87%).
Results A number of HER family biomarkers associated with response in the neratinib treatment arm (see Table 1):

TABLE 1

Association With pCR in Neratinib Treated and Concurrent Control Populations

| | P-value | |
| --- | --- | --- |
| Endpoint | Control | Neratinib |
| AKT S473 | 0.986 | 0.475 |
| AKT T308 | 0.591 | 0.580 |
| EGFR total | 0.098 | 0.185 |
| EGFR Y1068 | 0.252 | 0.015 |
| EGFR Y1148 | 0.360 | 0.784 |
| EGFR Y1173 | 0.291 | 0.018 |
| EGFR Y992 | 0.291 | 0.001 |
| ERBB2 total | 0.847 | 0.019 |
| ERBB2 Y1248 | 0.247 | 0.007 |
| ERBB3 total | 0.138 | 0.498 |
| ERBB3 Y1289 | 0.968 | 0.034 |
| ERK1/2 T202/Y204 | 0.895 | 0.557 |
| Heregulin total | 0.860 | 0.611 |
| mTOR S2448 | 0.786 | 0.328 |
| mTOR total | 0.229 | 0.135 |
| PI3K p85 Y458/p55 Y199 | 0.943 | 0.238 |
| PTEN S380 | 0.733 | 0.976 |
| SHC Y317 | 0.269 | 0.025 |

Seven (7) HER pathway markers (EGFR Y1068, EGFR Y1173, EGFR Y992, ERBB2 total, ERBB2 Y1248, ERBB3 Y1289, SHC Y317) were associated with response in the Neratinib (all patients without regard to HER2/HR status) but not the control arm (see FIG. 1). However, the difference in performance between arms did not reach significance by permutation testing. Adjusting for HR/HER2 status, EGFR Y1173 shows a significant biomarker×treatment interaction (p=0.049). In an exploratory analysis, patients were dichotomized by their EGFR Y1173 levels and evaluated the distribution of pCR rates (Table 2).

TABLE 2

Distribution of pCR rates within EGFR Y1173 Low/High groups stratified by the graduating HR−/HER2+ signature in each treatment arm.

| | Neratinib (N = 106) | | Control (N = 62) | |
| --- | --- | --- | --- | --- |
| | EGFR Y1173 Low (N = 31) | EGFR Y1173 High (N = 75) | EGFR Y1173 Low (N = 29) | EGFR Y1173 High (N = 33) |
| HR−/HER2+ (N = 28) | 0/4 (0%) | 12/18 (67%) | 1/1 (100%) | 1/5 (20%) |
| Not HR−/HER2+ (N = 140) | 3/27 (11%) | 24/57 (42%) | 5/28 (18%) | 5/28 (18%) |

Figure 2A:
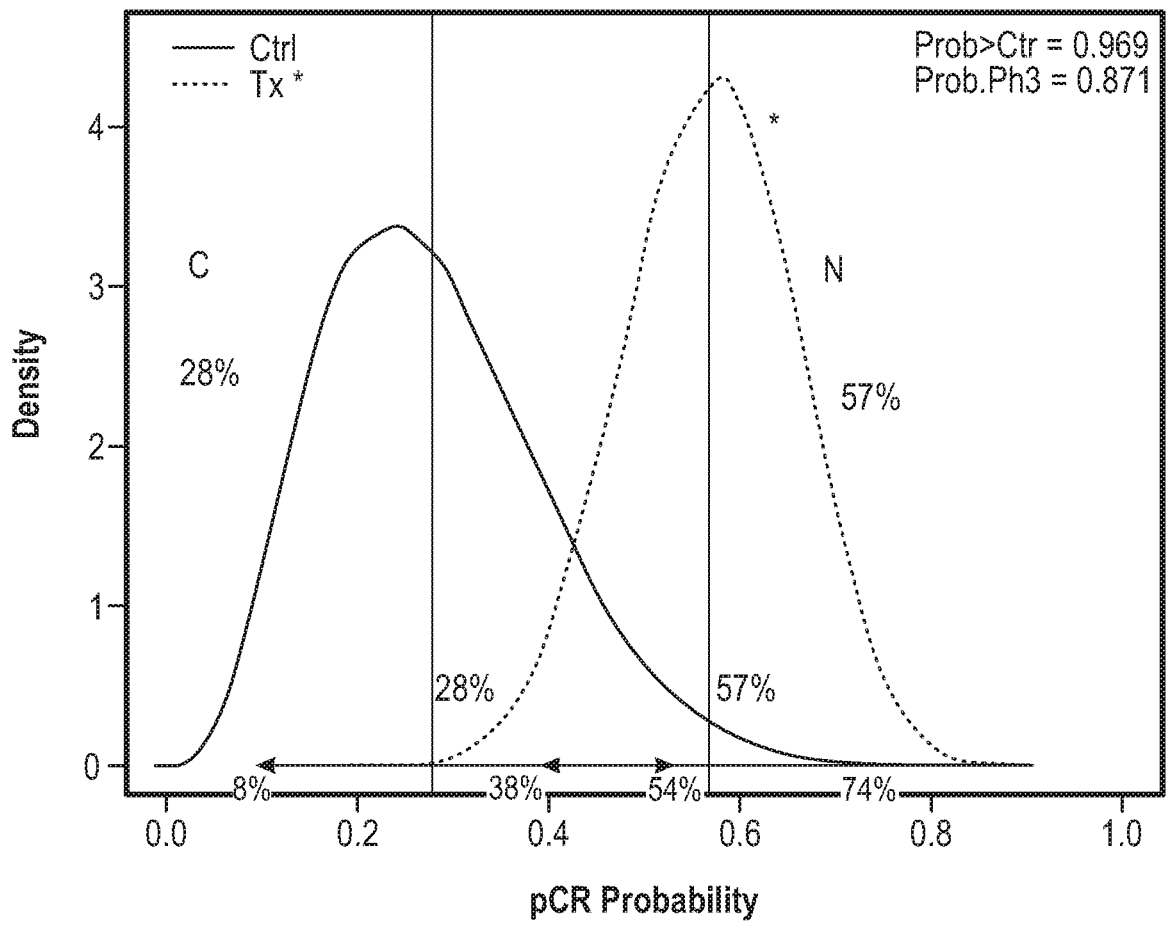
Figure 2B:
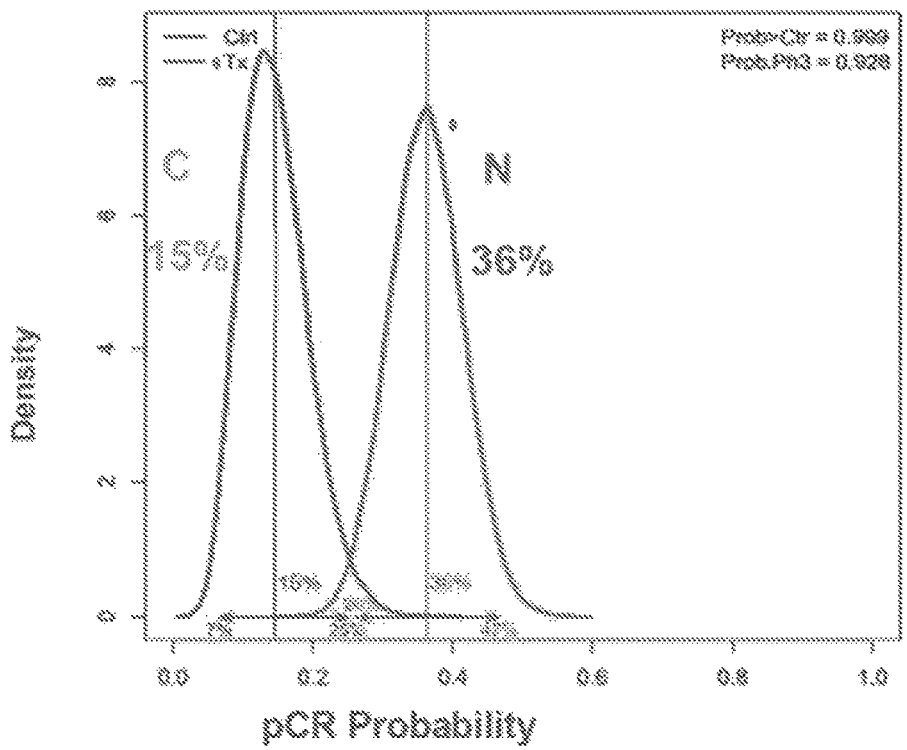
Figure 2C:
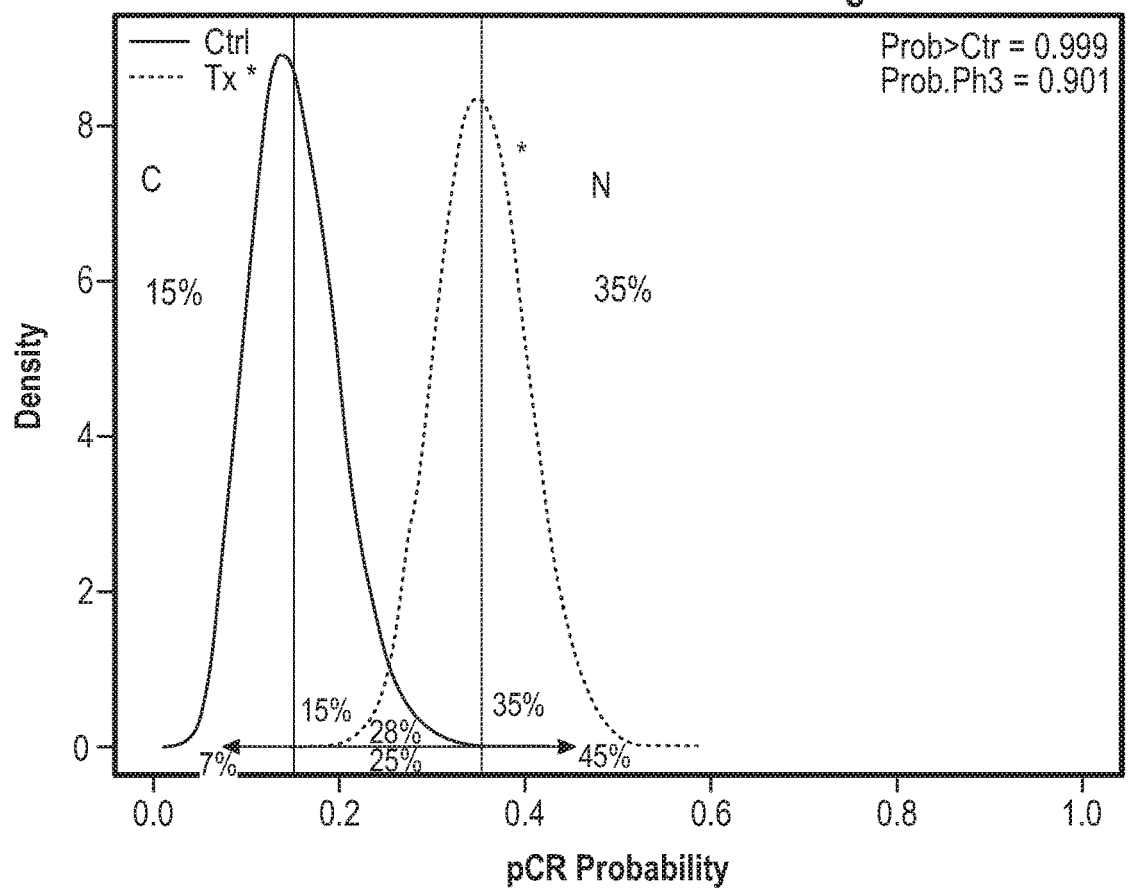

The odds ratio (OR) between EGFR Y1173 groups in the N relative to control arm was 10.1. When EGFR Y1173 High patients were added to the graduating HR−/HER2+ subset, the OR associated with treatment is 3.2 and is comparable to that in the HR−/HER2+ signature (OR: 2.1), while increasing the prevalence of biomarker-positive patients by ~50%. FIG. 2 provides Bayesian evaluation of EGFR Y1173 as a biomarker of neratinib response and Table 4 below provides estimates of probability of Neratinib superiority to control and probability of Phase III success.

TABLE 3

Bayesian Estimates of Probability of Neratinib Superiority to Control and Probability of Phase III Success

| | Prob > CTRL | Prob Ph III Success |
| --- | --- | --- |
| HR−/HER2+ | 0.97 | 0.87 |
| EGFR Y1173 High | 0.99 | 0.93 |
| HR−/HER2+ OR EGFR Y1173 High | 0.99 | 0.9 |
| HR−/HER2+ AND EGFR Y1173 High | 0.99 | 0.95 |

Measurements of the phosphorylation levels of EGFR (Y1173, Y992, Y1068) along with total and activated HER2 (Y1248) and SHC (Y317) were positively associated with response to neratinib combination therapy but not standard of care treatment. Levels of EGFR Y1173, but not total EGFR, are associated with response to neratinib combination therapy but not standard of care. As a single biomarker, dichotomized in an exploratory analysis using data from this trial, EGFR Y1173 appears to have a 93% probability of Phase III success, which exceeds that of the HR−/HER2+ graduating signature. When patients with high levels of phosphorylated EGFR (Y1173) are added to the HR−/HER2+ subgroup, the prevalence of 'biomarker-positive' patients increased by 50%, while increasing the predicted probability of Phase III success to 90%. These exploratory analyses suggest that EGFR Y1173 phosphoprotein represented a possible biomarker for expanding the predicted responding patient population.

Analysis shown here found that 7 HER pathway markers (EGFR Y1068, EGFR Y1173, EGFR Y992, ERBB2 total, ERBB2 Y1248, ERBB3 Y1289, SHC Y317) were associated with response to neratinib but not the control arm across all patients treated regardless of their HER2 and HR status.

Moreover, statistical analysis further revealed that EGFR Y1173 can be used to refine the specific HER2+HR− cohort where neratinib showed clinical success. The ability of these 7 markers to add to and refine the HER2+HR− cohort could provide significant improvement of patient selection for neratinib treatment and be valuable companion diagnostic/theranostic markers.

Example 2

In the same manner as described in Example 1, the following biomarkers were identified as being predictive for a positive outcome for the subjects of Example 1, pCR. The protein levels were measured for one or more of the biomarkers disclosed herein, the measured protein levels were compared to the protein levels from control samples (which formed the baseline value for each biomarker) ALK.Y1586; ALK.Y1604; AMPKb1.S108; Caspase.7, cleaved D198; Cyclin.B1 total; Cyclin.D1.total; EGFR.Y1068, EGFR.Y1173, EGFR.Y992, eIF4G.S1108; IGFBP5.total; ERBB2.total; ERBB2.Y1248; ERBB2.Y877; ERBB3.Y1289; ERBB4.Y1284; FAK.Y576.Y577; JAK1.Y1022 and Y1023; JAK2.Y1007; MEK1.2.S217 and S211; MET.Y1234 and Y1235; p70S6K.T389; p70S6K.T412; PI3K.p85.Y458.p55. and Y199; AKT S473; AKT T308; EGFR total; EGFR Y1148; ERBB3 total; ERK1/2 T202/Y204; Heregulin total; mTOR S2448; mTOR total; PTEN S380; SHC Y317; PARP.total; PDGFRa.Y754; RET.Y905; RTK.ROR1.total; SHC.Y317; STAT5.Y694; VEGFR2.Y996; X4EBP1.S65; AMPKa1.S485; A.RAF.S299; IGF1R.Y1131. and IR.Y1146; MCSFR.Y732; A.RAF.S299; LC3B.total; TIE2.Y992; a JAK.STAT.pathway score (which is the sum of the measurements for JAK1 Y1022/Y1023, JAK1 Y1007, STAT1 Y701 STAT2Y727, STAT3 Y705, STAT5 Y694), a mTOR pathway score (which is the sum of the measurements for 4EBP1 S65; eIF4E S209; eIF4G S1108; eIF4G S1108; eIF4G S1108; mTOR S2448; p70S6K S371; p70S6K T389; p70S6K T412; S6RP S240/S244); a HER Family pathway score (which is the sum of the measurements for EGFR Y1068; EGFR Y1173; EGFR Y992; ERBB2 Y1248; ERBB3 Y1289; FAK Y576/Y577; SHC Y317; STAT5 Y694; RET Y905); and a RTK pathway score (which is the sum of the measurements for ALK Y1604; EGFR Y1068; EGFR Y1173; EGFR Y992; ERBB2 Y1248; ERBB3 Y1289; FAK Y576/Y577; SHC Y317; STAT5 Y694; ERBB2 Y877; ERBB4 Y1284; MET Y1234-Y1235; ROS Y2274; RET Y905), or combinations thereof. FIGS. 5-10, inclusive of alphabetically labeled portions, show the analysis of these biomarkers as being predictive for a positive response to administration of neratinib for treatment of breast cancer.

Example 3

Reverse Phase Protein Microarray (RPPA)

The Reverse Phase Protein Microarray (RPPA) technology was developed to address the analytical challenges of the sandwich and forward phase protein arrays (e.g. mismatch of sandwich antibody affinity, imprecision within and between analytes, and poor sensitivity). The platform was designed to enable non-subjective, quantitative, multiplexed analysis of specific forms of cellular proteins (e.g. phosphorylated, unphosphorylated, and cleaved) from a limited amount of starting sample, such as with a fine needle aspirate or laser capture microdissected (LCM) cellular material to procure pure populations of the target cells of interest. Particularly suited for clinical tissue samples, RPPA uses a single antibody directed against the epitope of interest.

A key attribute of the RPPA was the ability to quantitatively measure hundreds of signaling proteins concomitantly from only a few thousand cells, thus providing a critical means of broad-scale cell signaling analysis directly from tissue samples, cell culture models, and animal tissues from pre-clinical studies. The RPPA technology was optimized for routine clinical sample analysis (1-10), and is currently employed within the CAP/CLIA complaint proteomics laboratory within the Center for Applied Proteomics and Molecular Medicine at George Mason University. No other technology can measure the activity of as many signaling proteins at once from such small amounts of input material.

The Reverse Phase Protein Microarrays (RPPA) immobilizes the test sample analytes (eg. lysate from laser capture microdissected cells) on the solid phase. An analyte-specific ligand (e.g. antibody) is applied in the solution phase (Capture). Bound antibodies are detected by secondary tagging and signal amplification (Signal Generation).

The RPPA method has the following major steps.
Overview of RPPA

A selection of peer-reviewed publications contains extensive detailed description of the basic core components RPPA methodology (See references). The RPPA format immobilizes an individual test sample in each array spot. See FIG. 3. An array can be comprised of up to hundreds of patient samples or cellular lysates. Each array was incubated with a single primary antibody and a single analyte end point was measured. Since RPPAs maintained the concentration of the input sample, the sensitivity was greater as compared with a forward phase, (e.g. antibody array) probed with the same small number of input cells.

With the RPPA technology, serial dilutions were printed of each sample, control or standard, to maintain sample concentration. Each spot contained a bait zone measuring only a few hundred microns in diameter. The detection probe can be tagged and signal amplified independently from the immobilized analyte protein. Coupling the detection antibody with highly sensitive amplification systems yielded detection sensitivities to fewer than 1,000 to 5,000 molecules per spot with good linearity (correlation coefficient or $R^2$=0.990-0.999) and inter-experiment precision ($R^2$=0.973). Between run and within run analytical precision was between a 3-13% CV (coefficient of variation) (7).

The RPPA technology has been developed and optimized for performance as a fluorescent-based calibrated assay, generally identical in design and analysis to standard ELISA or standard clinical immunoassays. As a calibrated assay, each assay consists of:

1. Experimental patient samples printed in triplicate two-spot dilutions (neat and 1:4)
2. High, medium, and low controls printed in triplicate two-spot dilutions (e.g., neat and 1:4)
3. A calibrator, consisting of a 6-10-point curve whereby the analyte of interest is decreasing in concentration in the background of a constant protein concentration.

The analyte concentration was thereby determined by extrapolation to a non-parametrically determined curve fit of the calibration curve and reported in relative fluorescent units.

Sample Preparation for Microarray

In order to prepare the sample for arraying, proteins were extracted from the LCM polymer cap as a whole cell lysate using a heated sodium dodecyl sulfate-based lysing solution which produced a denatured lysate suspended in the sample/ extraction buffer. The optimal extraction buffer for extracting proteins from tissue cells that have been procured by LCM, with the purpose of performing reverse phase protein arrays, consisted of a detergent, denaturing agent and buffer. This buffer was an efficient denaturing extraction buffer for the extraction and solubilization of cellular proteins from fixed and frozen tissue. An array layout grid was used to determine exact placement of sample and control cell lysates on the printed microarray. Cell lysate solutions for each sample, of a known volume and concentration were loaded into 384 well microtiter plates. Microtiter plates were specifically labeled and loaded into the well plate hotel in the correct order.

The RPPA used slides coated with nitrocellulose. This type of slide was chosen for its high binding capacity, high surface area, minimum effect on protein structure, and intrinsically low background signal. For the printing run, up to 100 slides, (10 slides/platen and 10 platens within the Substrate Hotel), were loaded into the Aushon 2470 Arrayer at a time.

Array Preparation

The Aushon 2470 Arrayer had a general software program to manage the printing process. The program enabled customization of array printing, with parameters such as top and left offset of printing, depositions/feature, slide lot number, number of replicates, dwell time for pins, total number of immersions, maximum number of extractions and wash sequences.

Calibration of Values

Figure 3:
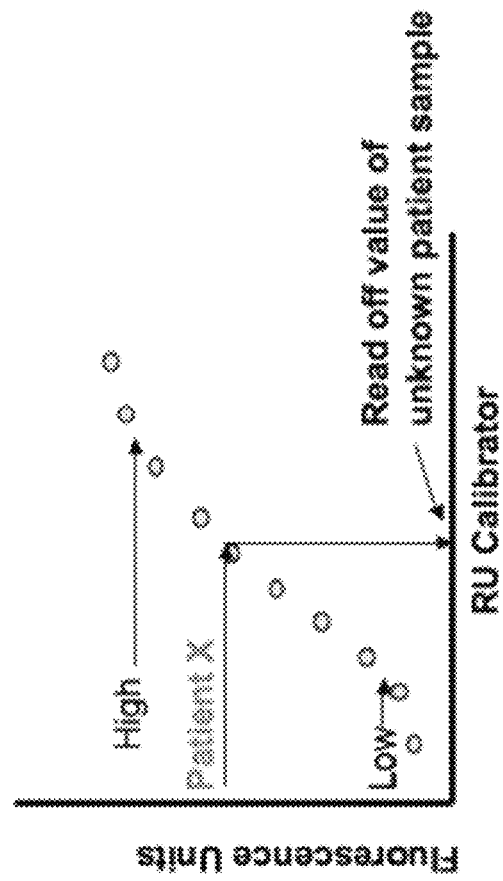
FIG. 3 shows an example of a reverse phase protein microarray.
Figure 3:
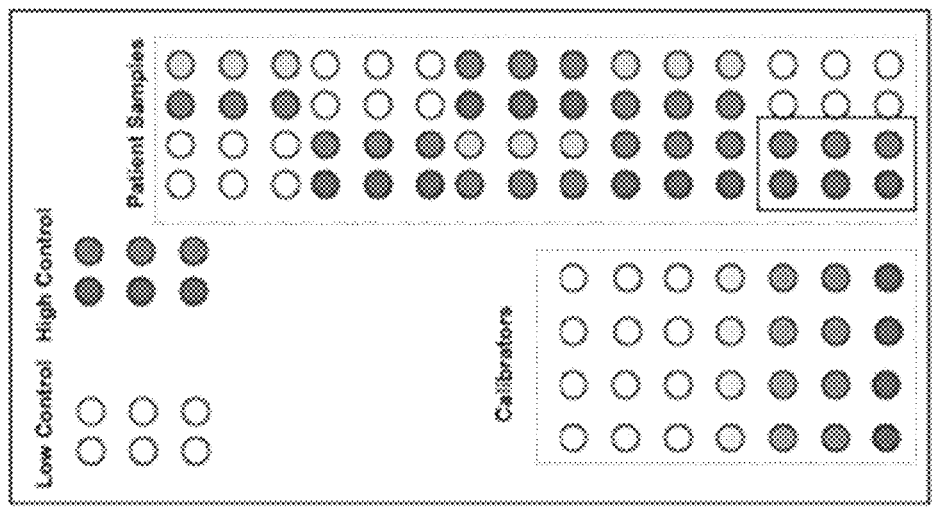
Figure 4A:
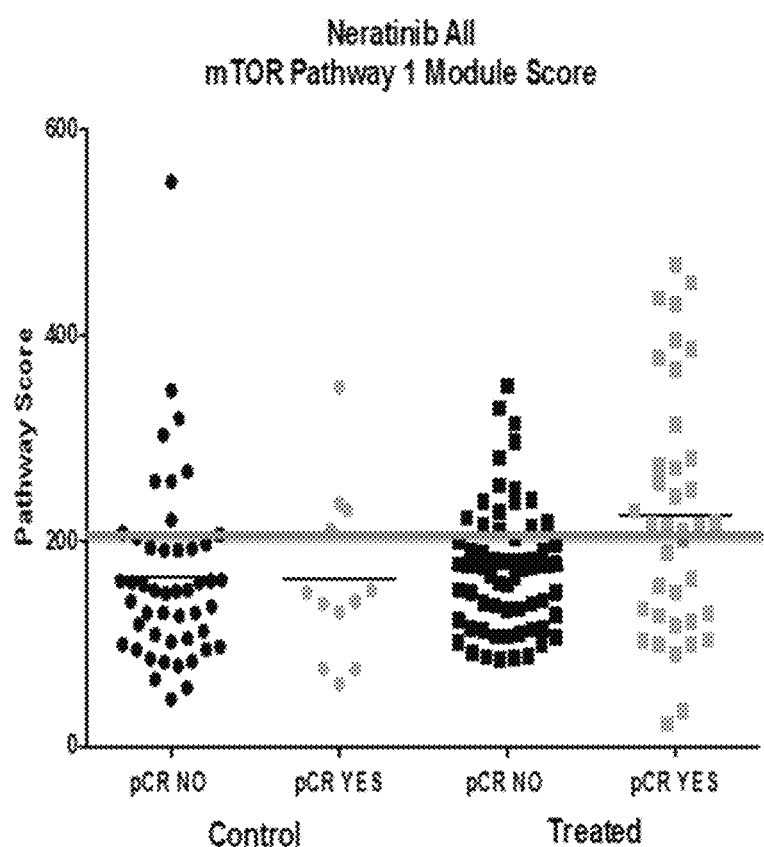
FIGS. 4A and 4B are scatter plots of all subjects, not divided by HR or HER2 phenotype, for biomarkers mTor pathway score (A) and HER pathway score (B).
Figure 4B:
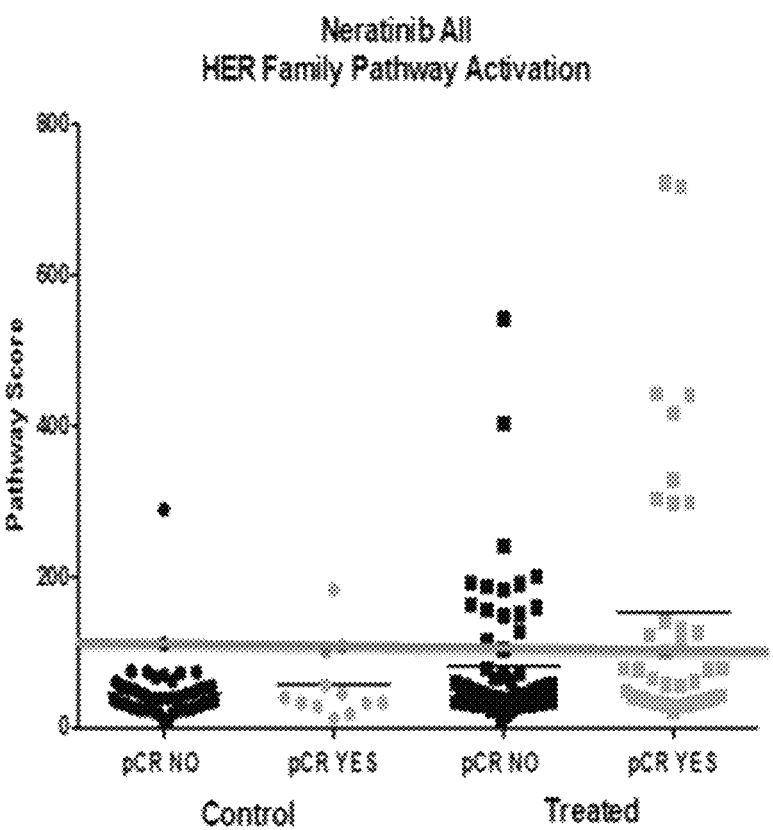
Figure 5A:
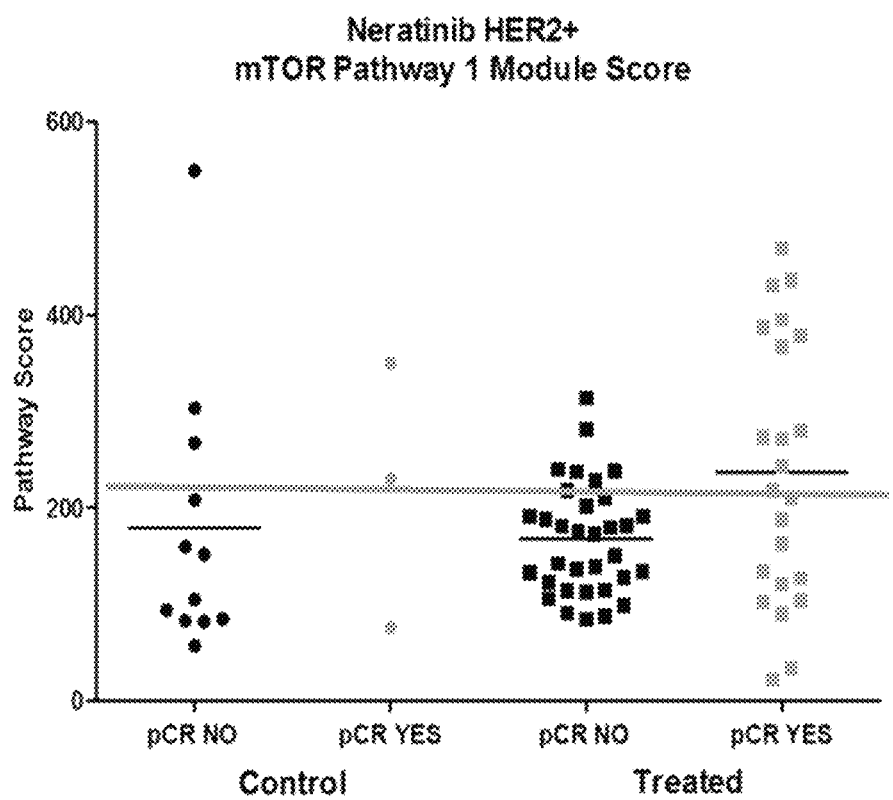
FIGS. 5A-E are scatter plots of HER2+ phenotype subjects, for biomarkers mTor pathway score (A); HER pathway score (B); ALK Y1586 (C); p70S6K T412 (D); EGFR Y992 (E).
Figure 5B:
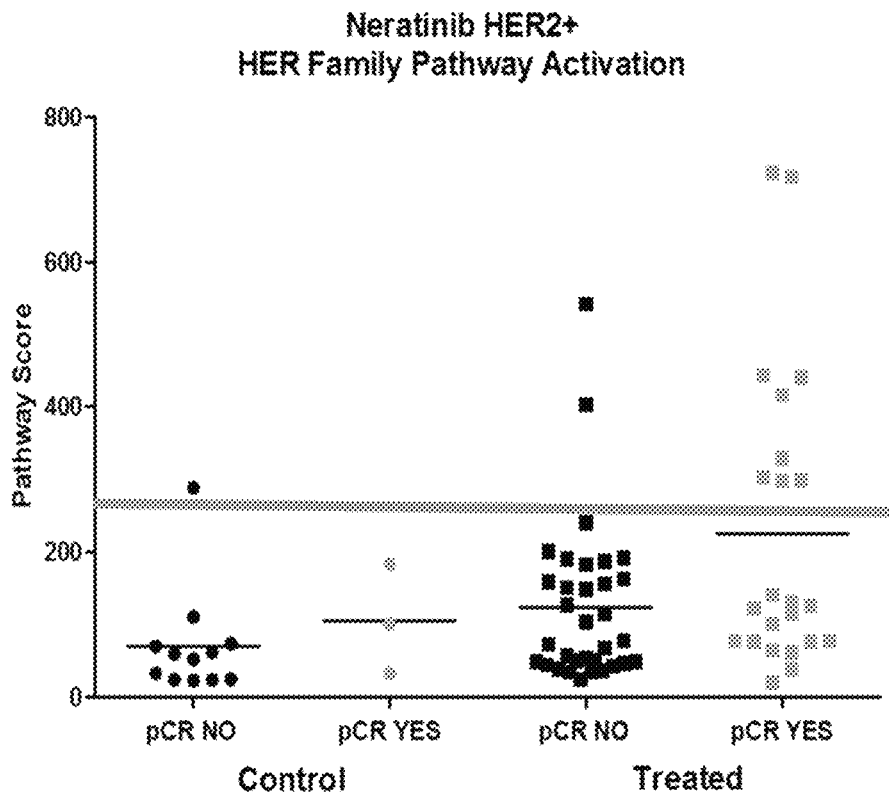
Figure 5C:
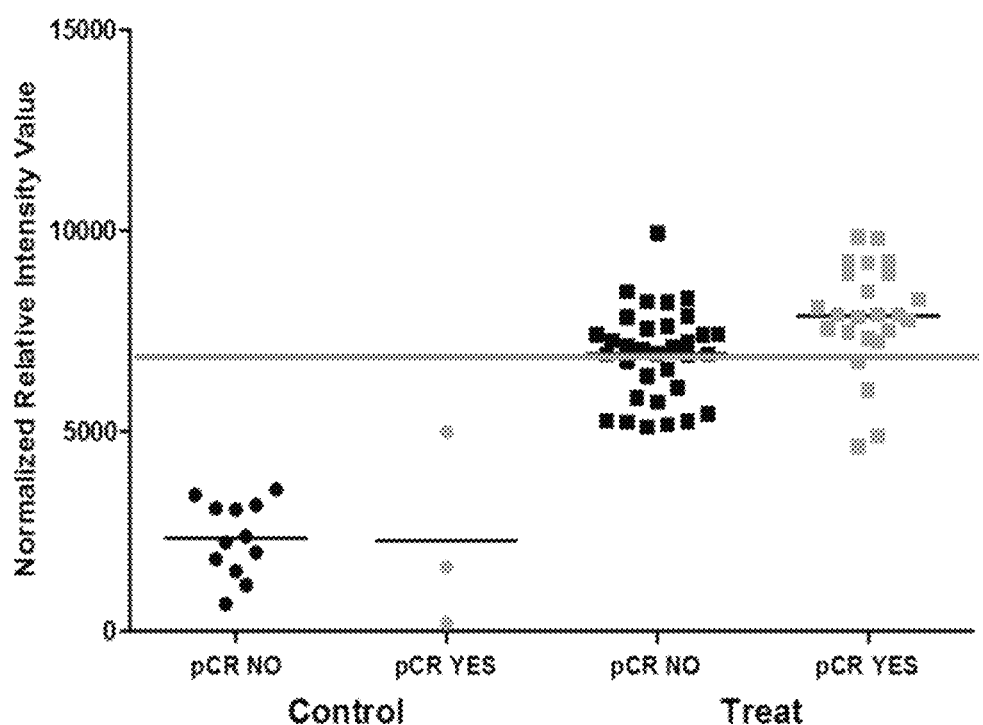
Figure 5D:
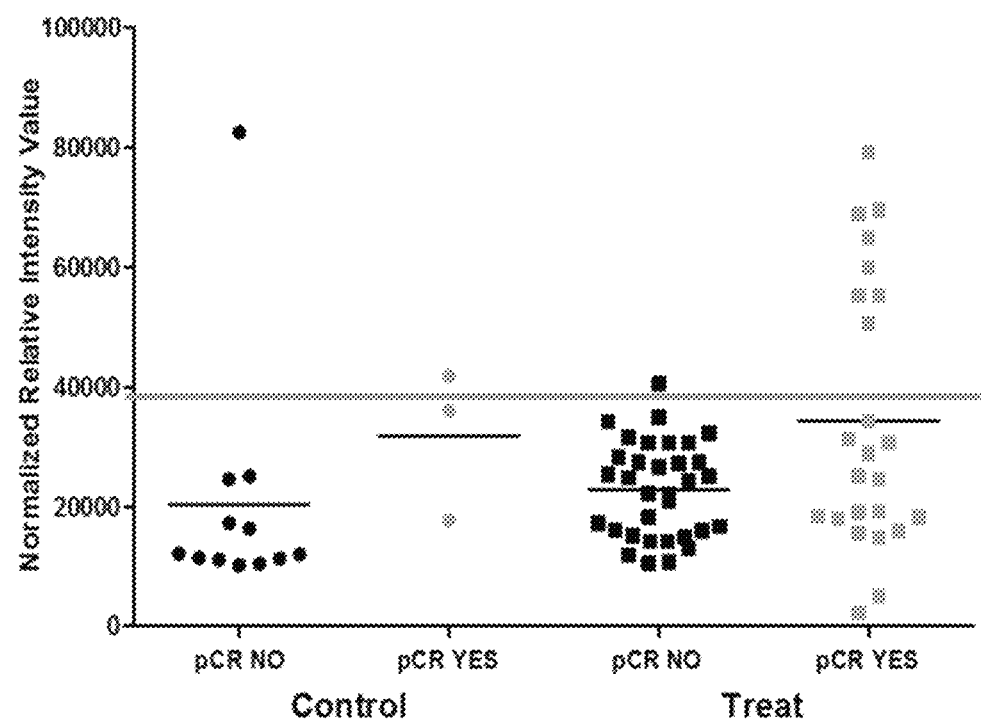
Figure 5E:
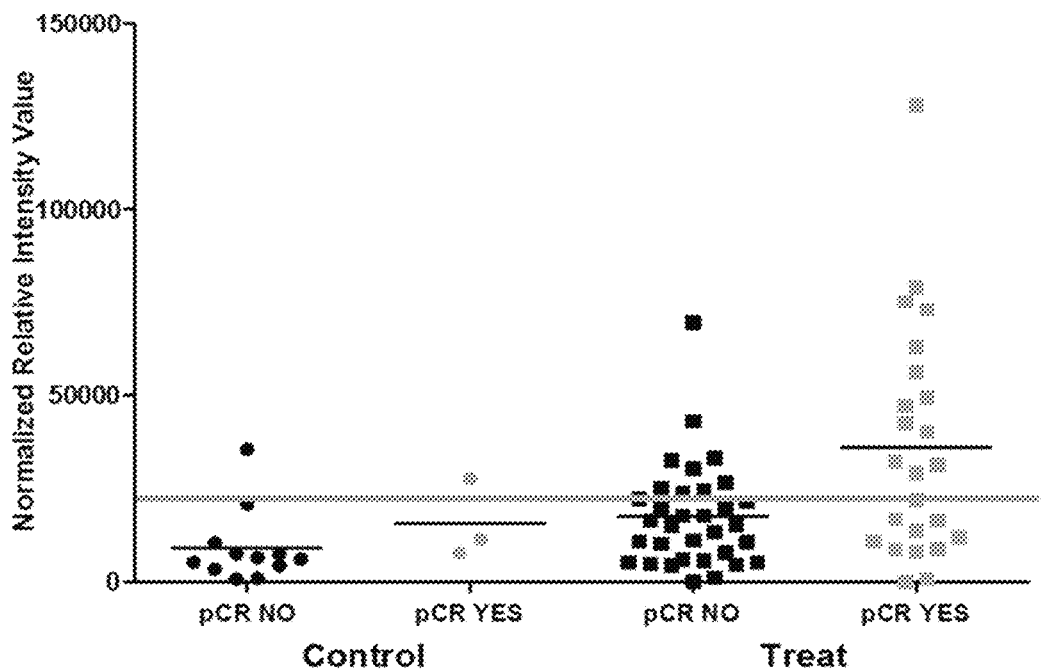
Figure 6A:
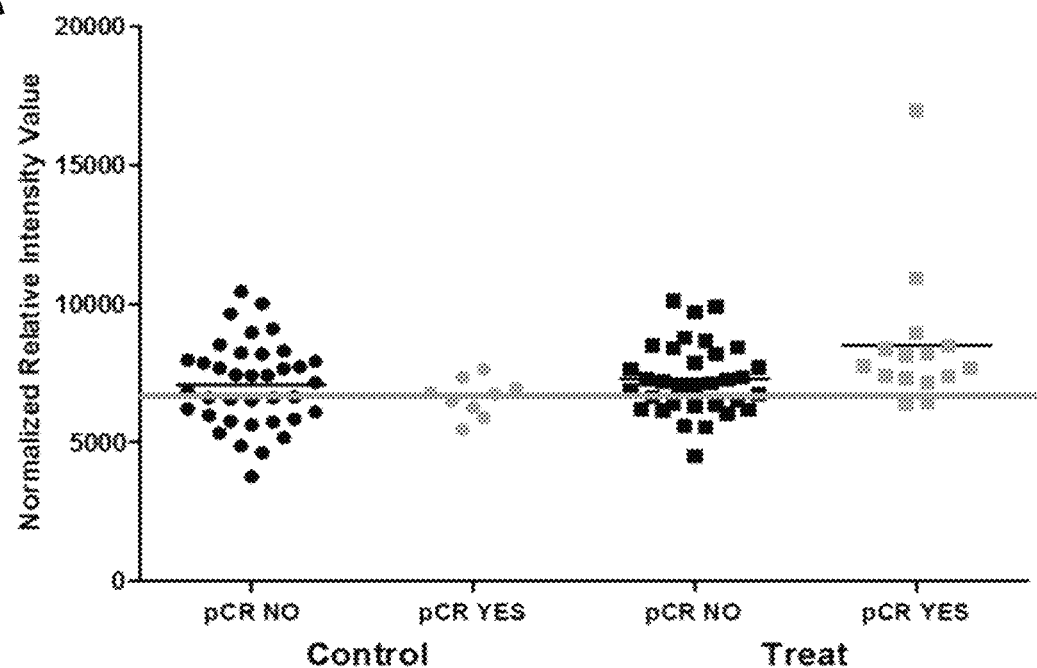
FIGS. 6A-D are scatterplots of HER2− phenotype subjects, for biomarkers ALK Y1586 (A); EGFR Y1173 (B); RTK-ROR1 total (C); TIE2 Y992 (D).
Figure 6B:
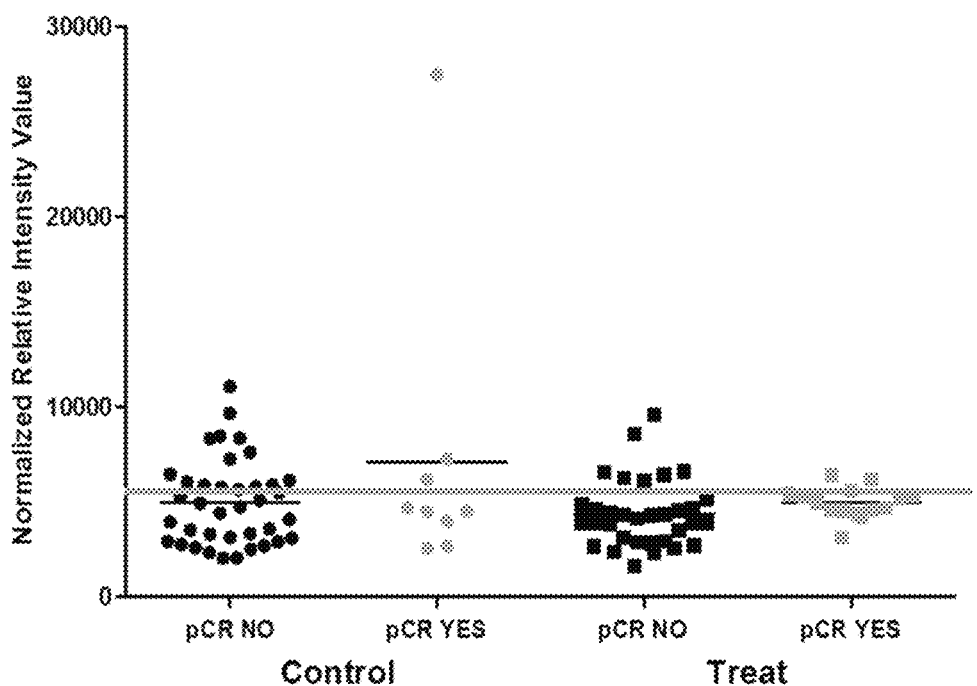
Figure 6C:
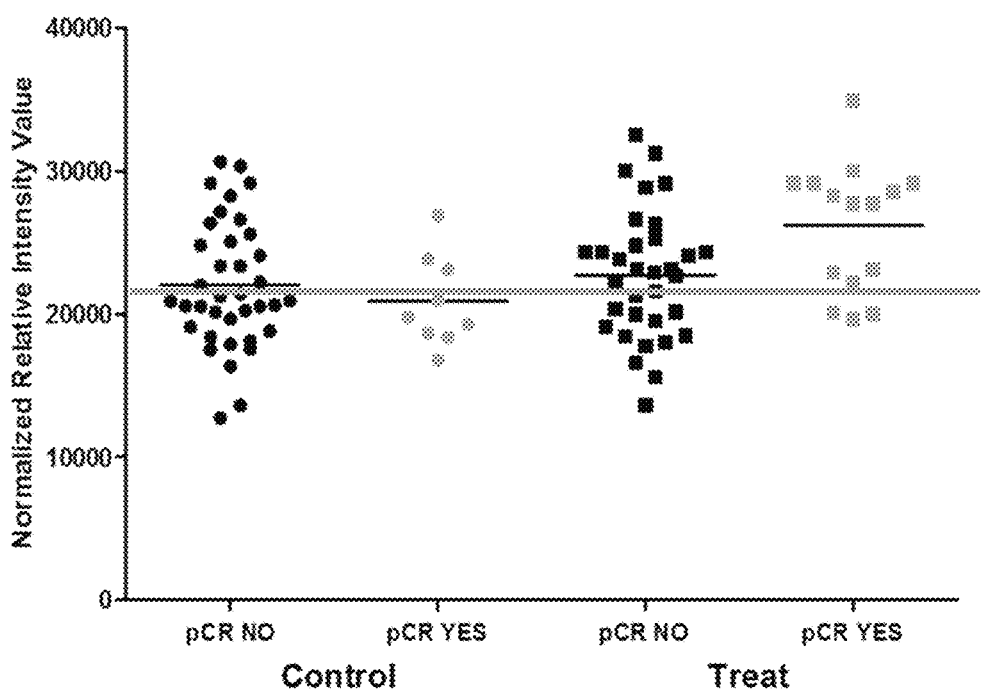
Figure 6D:
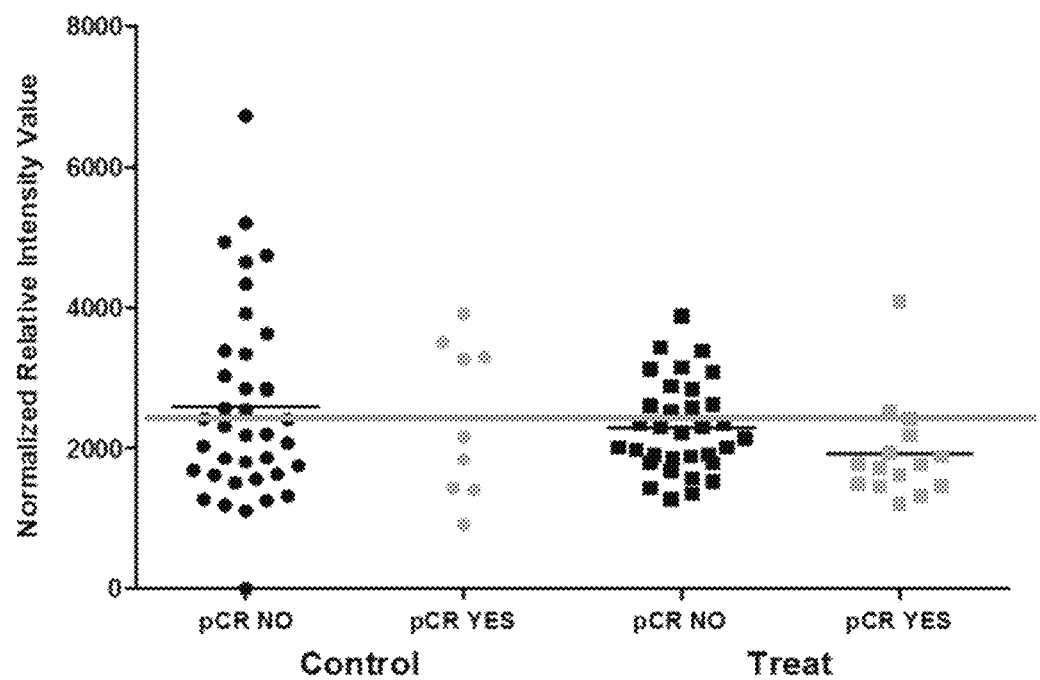
Figure 7I:
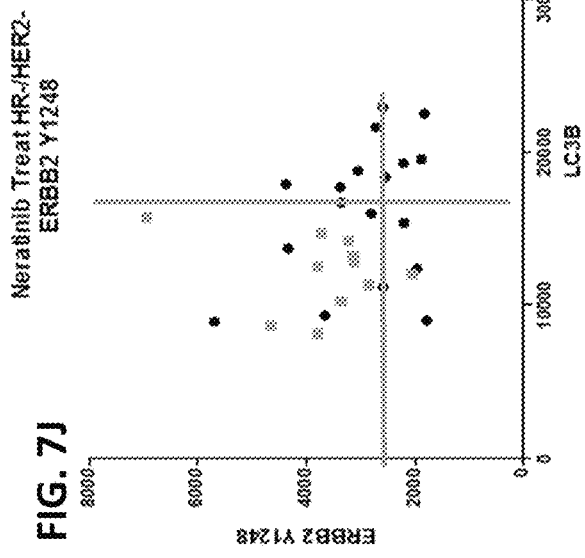
Figure 7K:
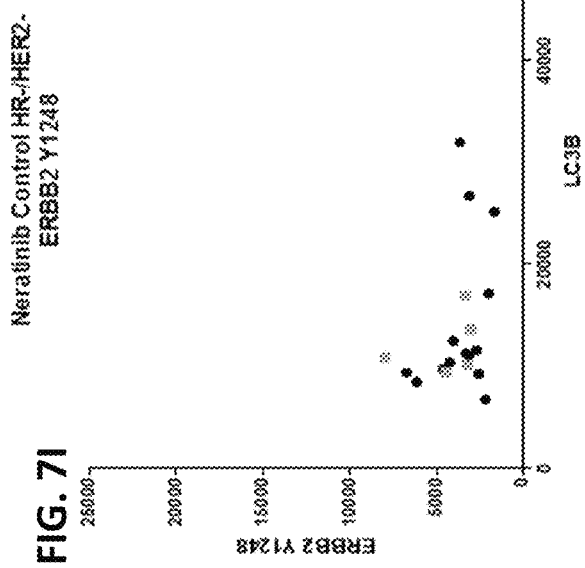
Figure 7J:
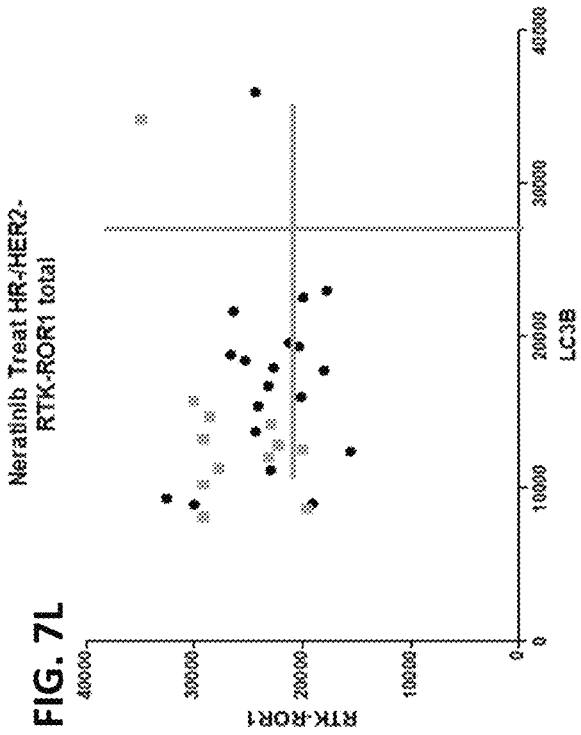
Figure 7L:
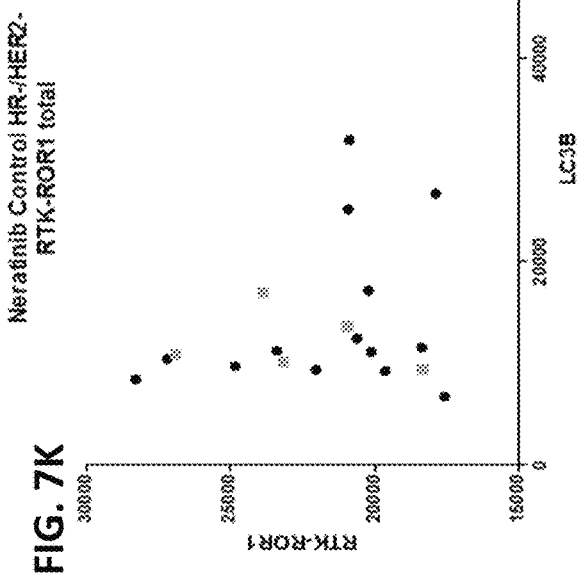
Figure 8A:
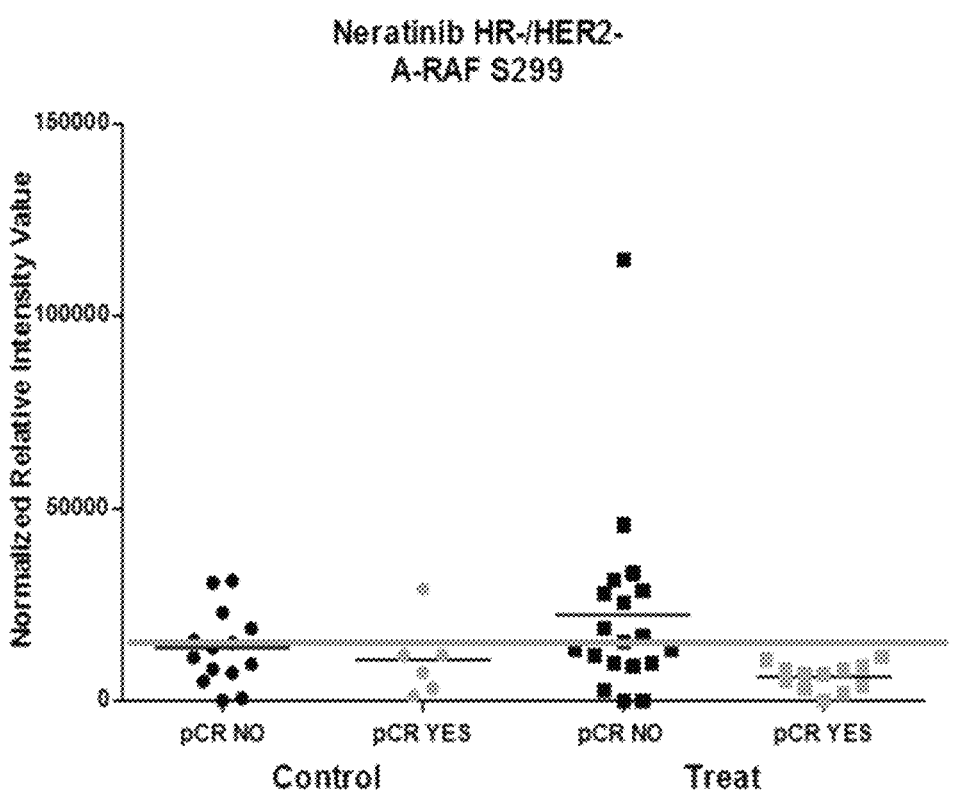
FIGS. 8A-D show two-way scatter plots for HR−/HER2− subjects, control and treated subjects, for various biomarkers.
Figure 8B:
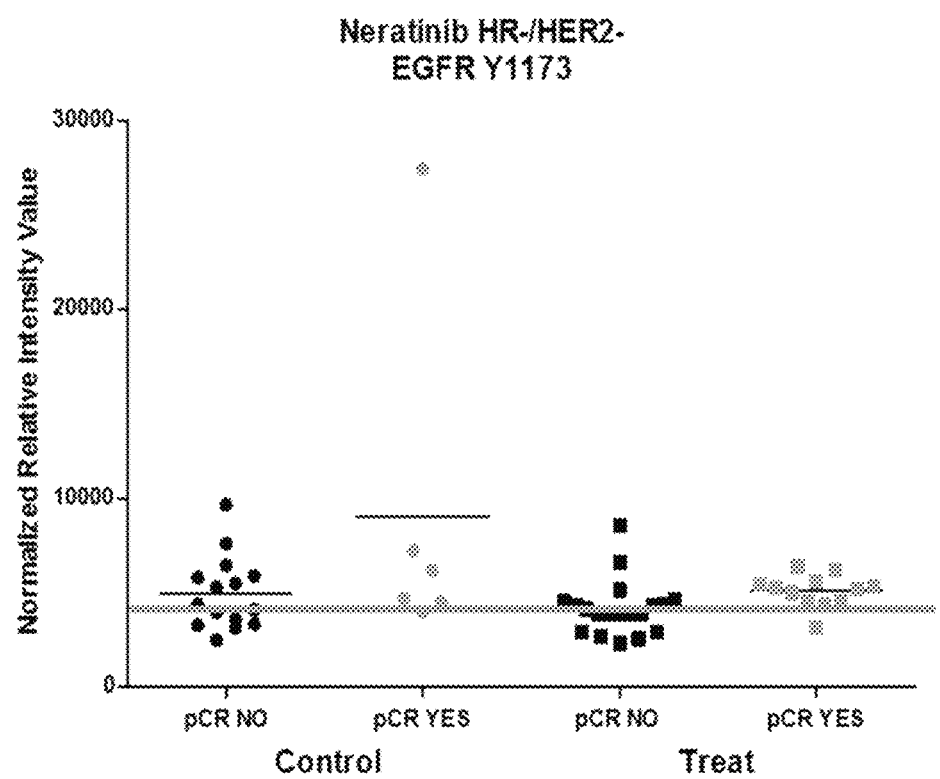
Figure 8C:
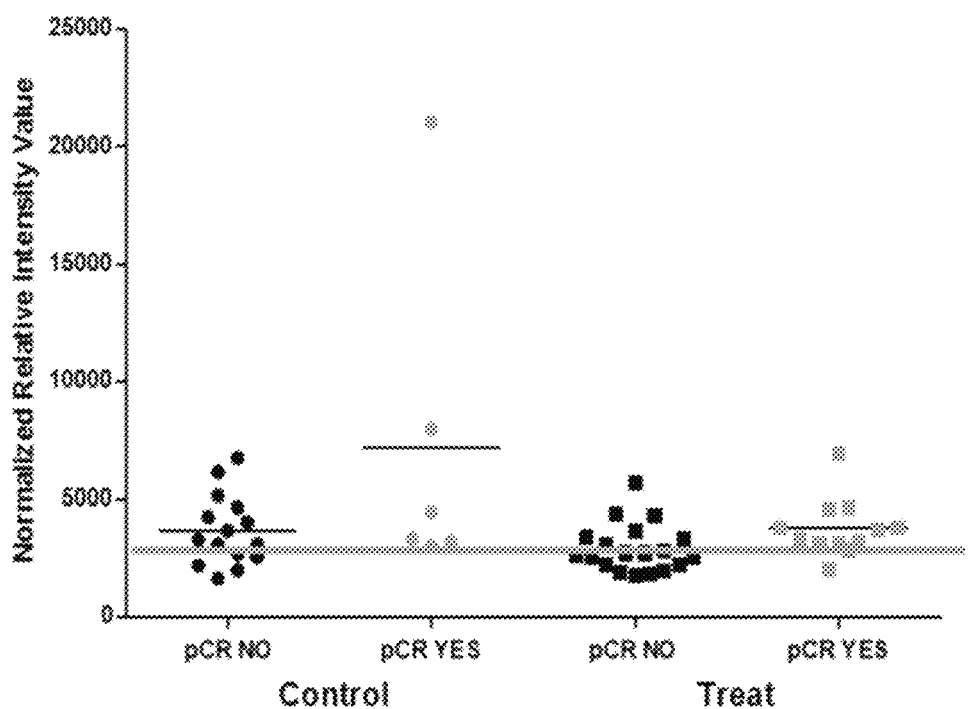
Figure 8D:
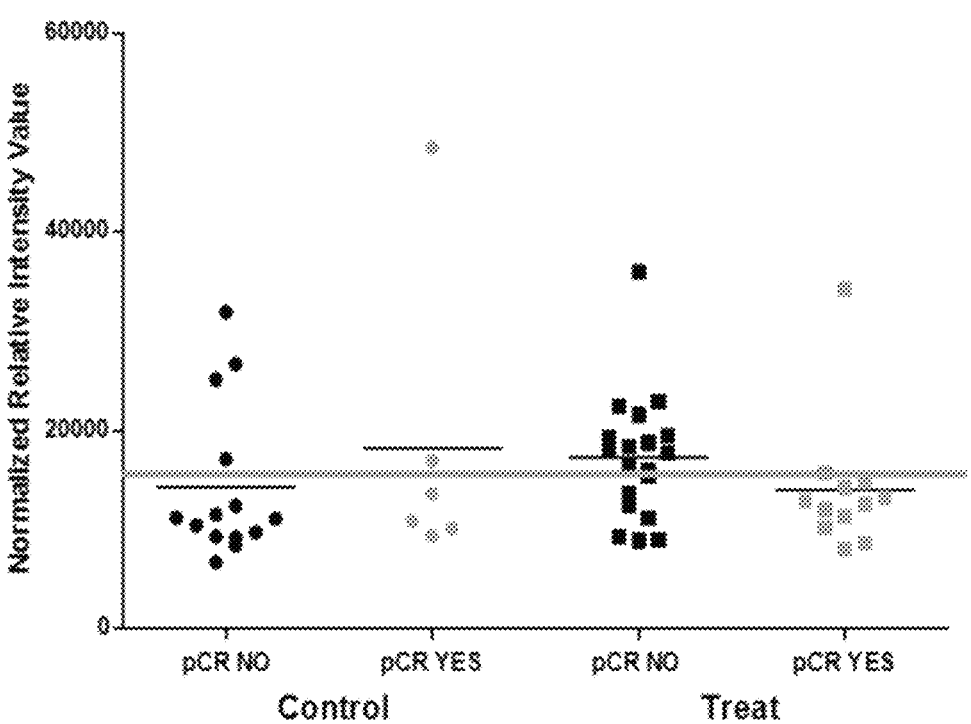
Figure 9A:
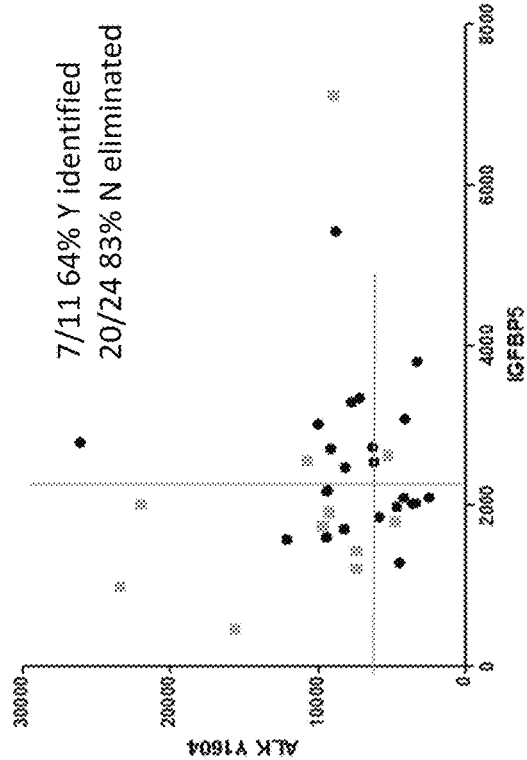
FIGS. 9A-H show two-way scatter plots for HR+/HER2+ subjects, control and treated subjects, for various biomarkers.
Figure 9B:
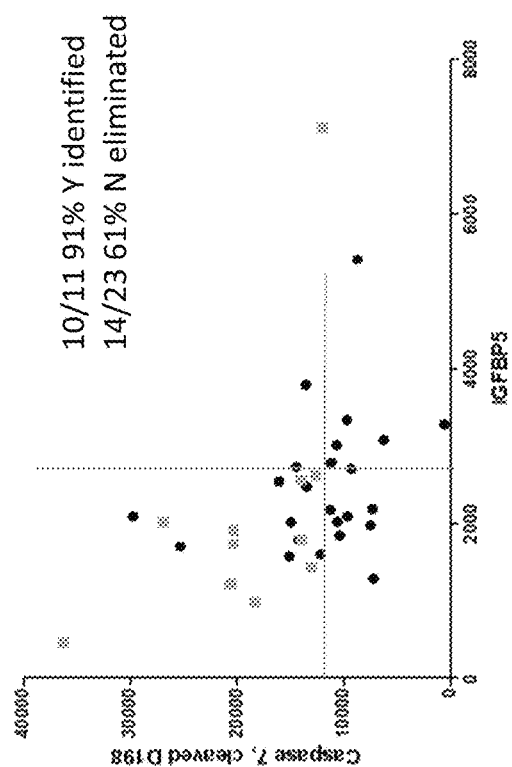
Figure 9C:
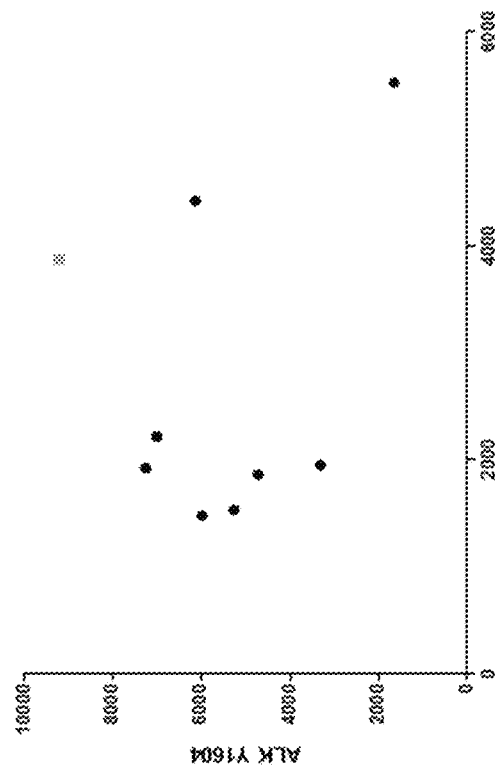
Figure 9D:
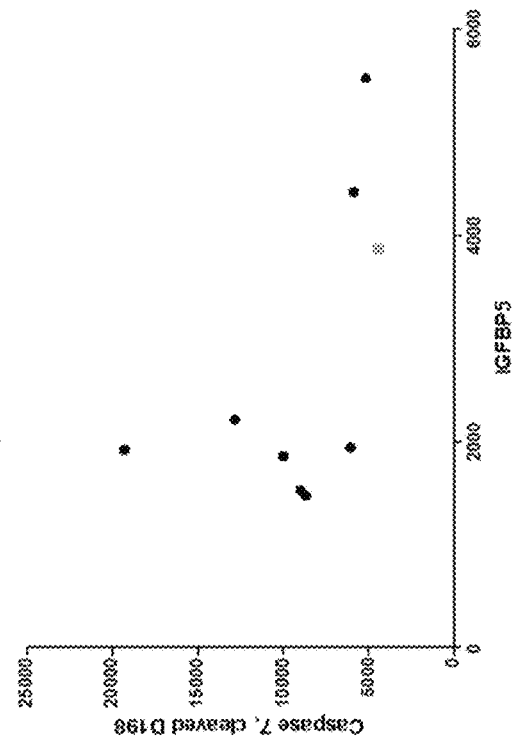
Figure 9E:
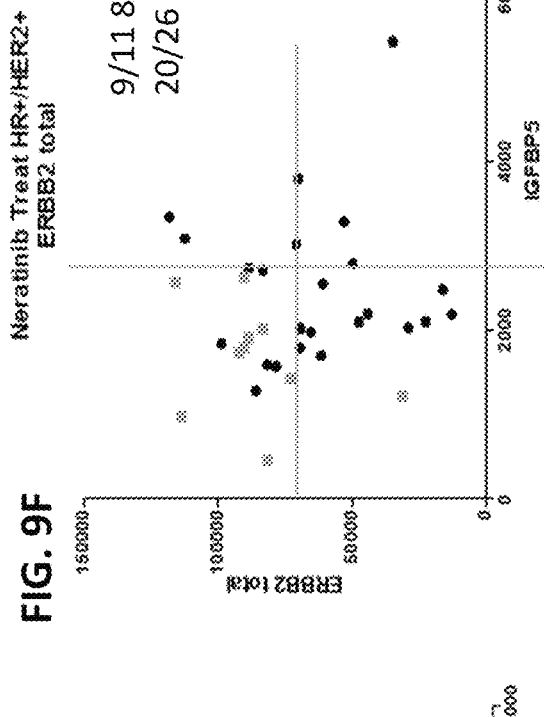
Figure 9F:
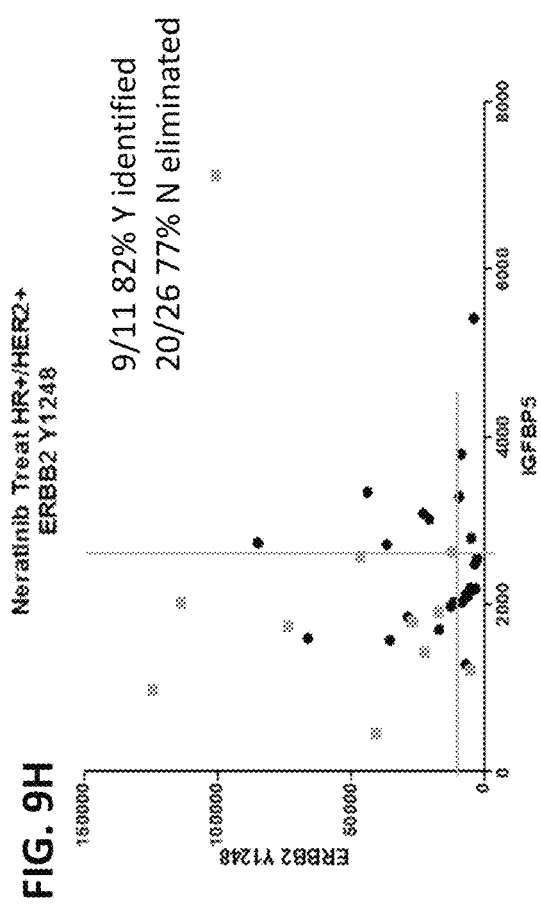
Figure 9G:
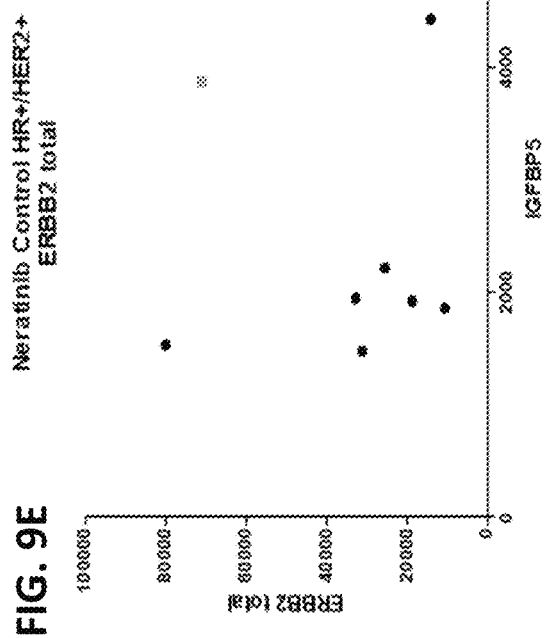
Figure 9H:
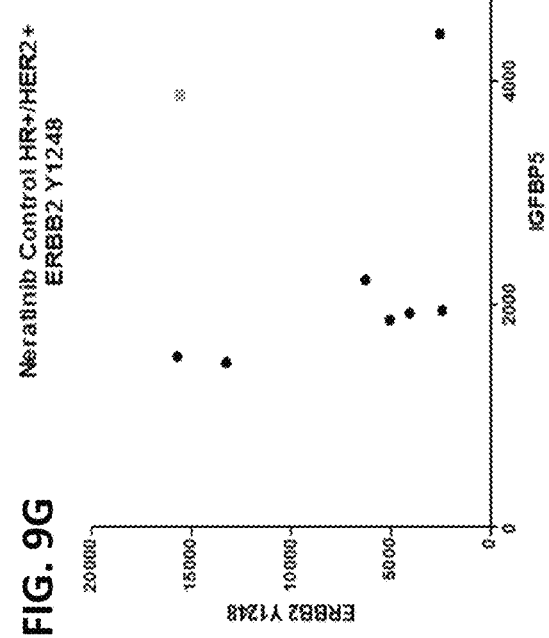
Figure 10A:
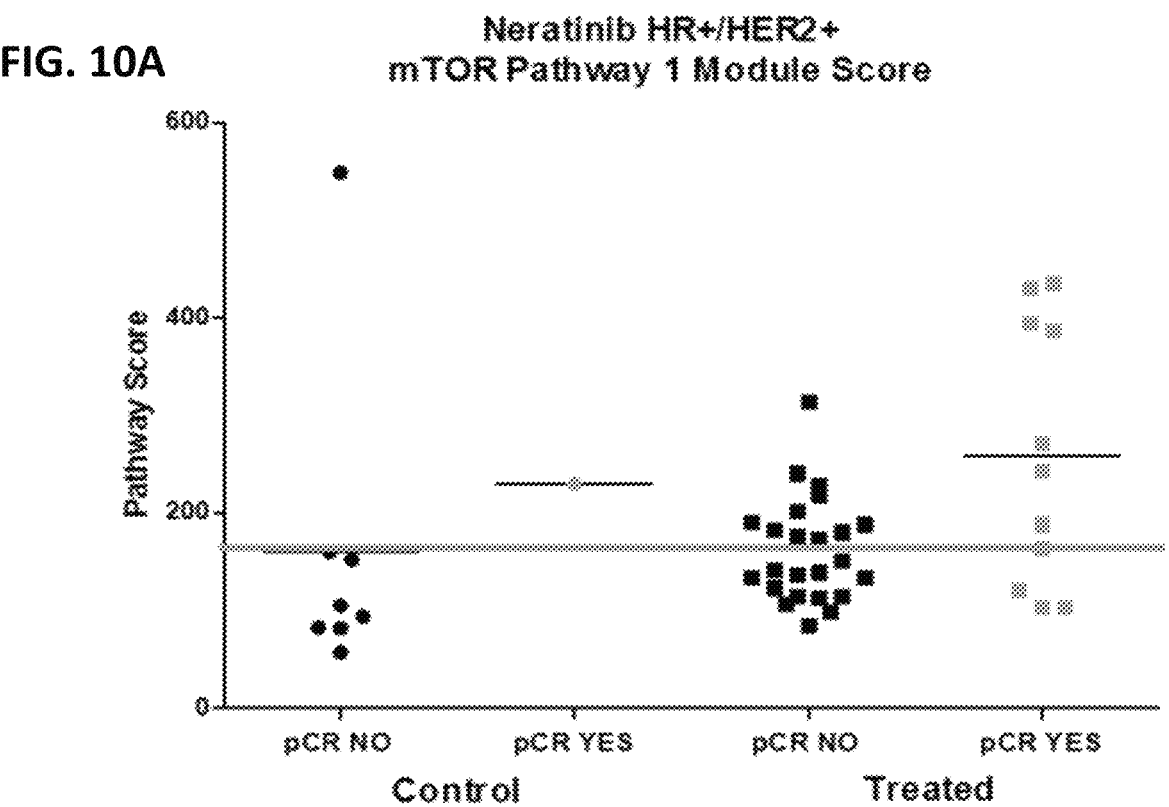
FIG. 10A-J show two-way scatter plots for HR+/HER2+ subjects, control and treated subjects, for various biomarkers.
Figure 10B:
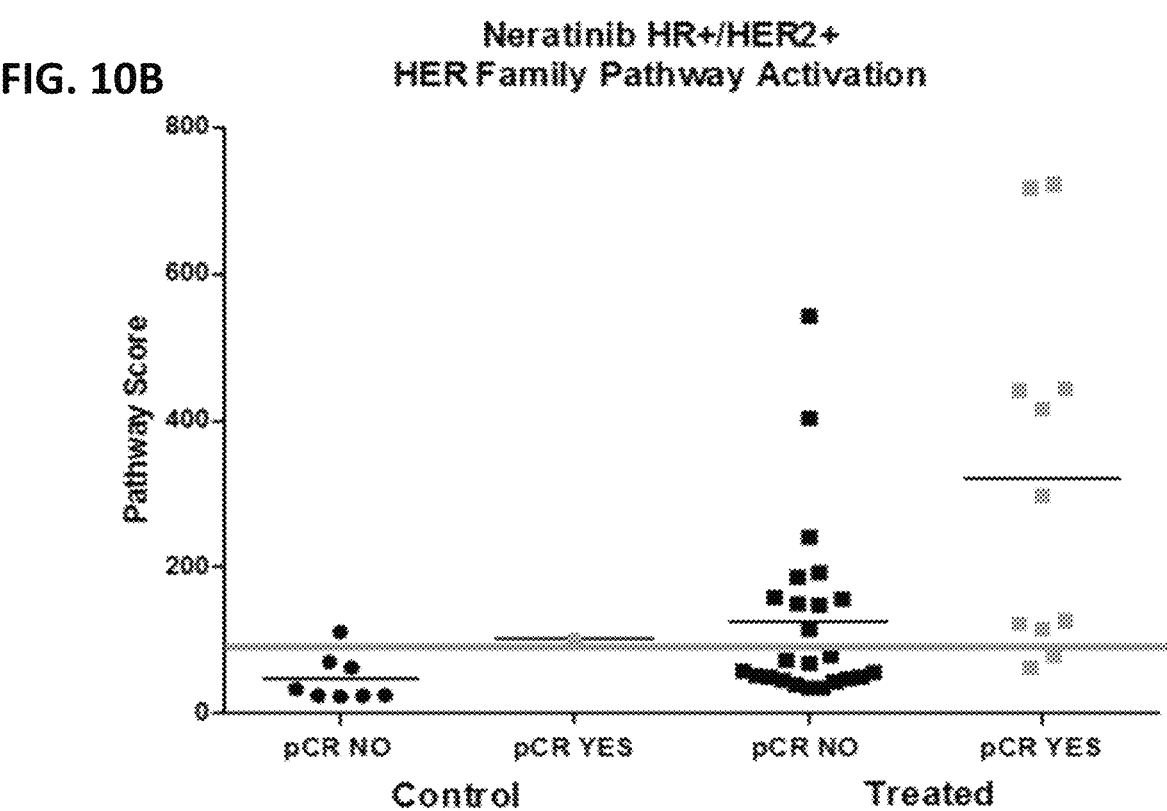
Figure 10C:
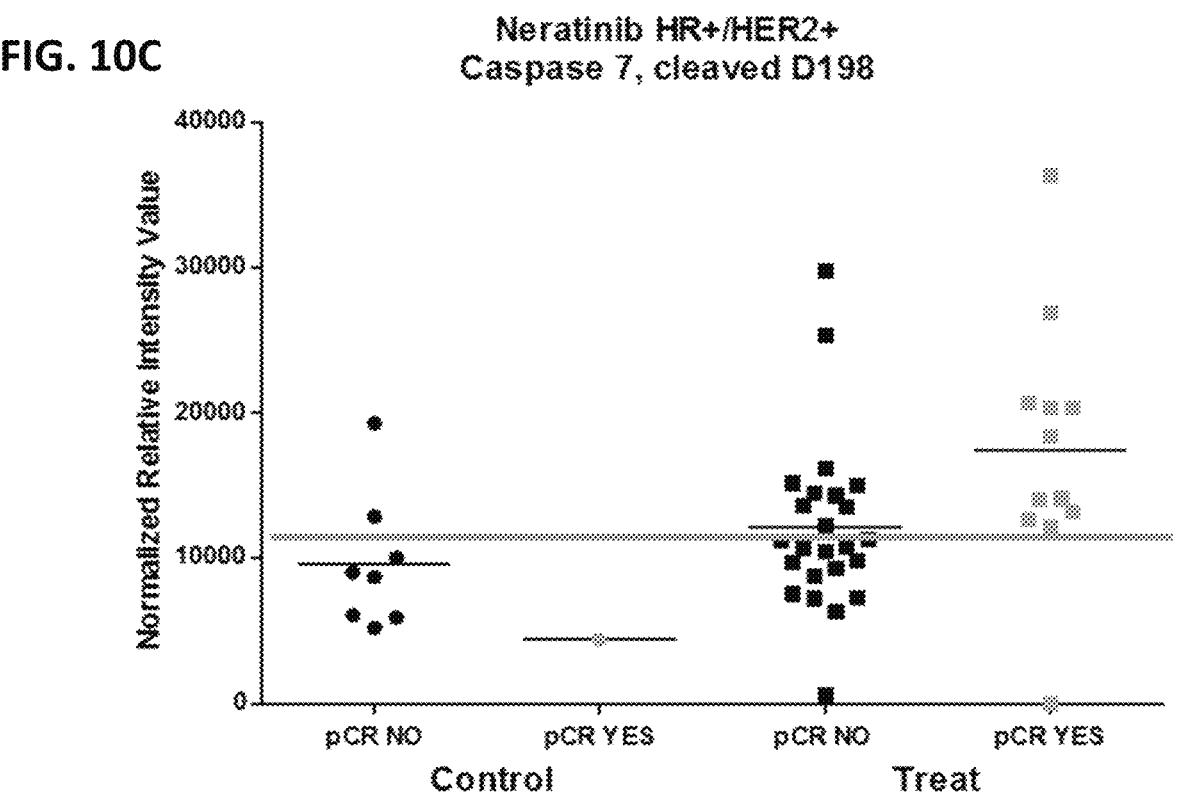
Figure 10D:
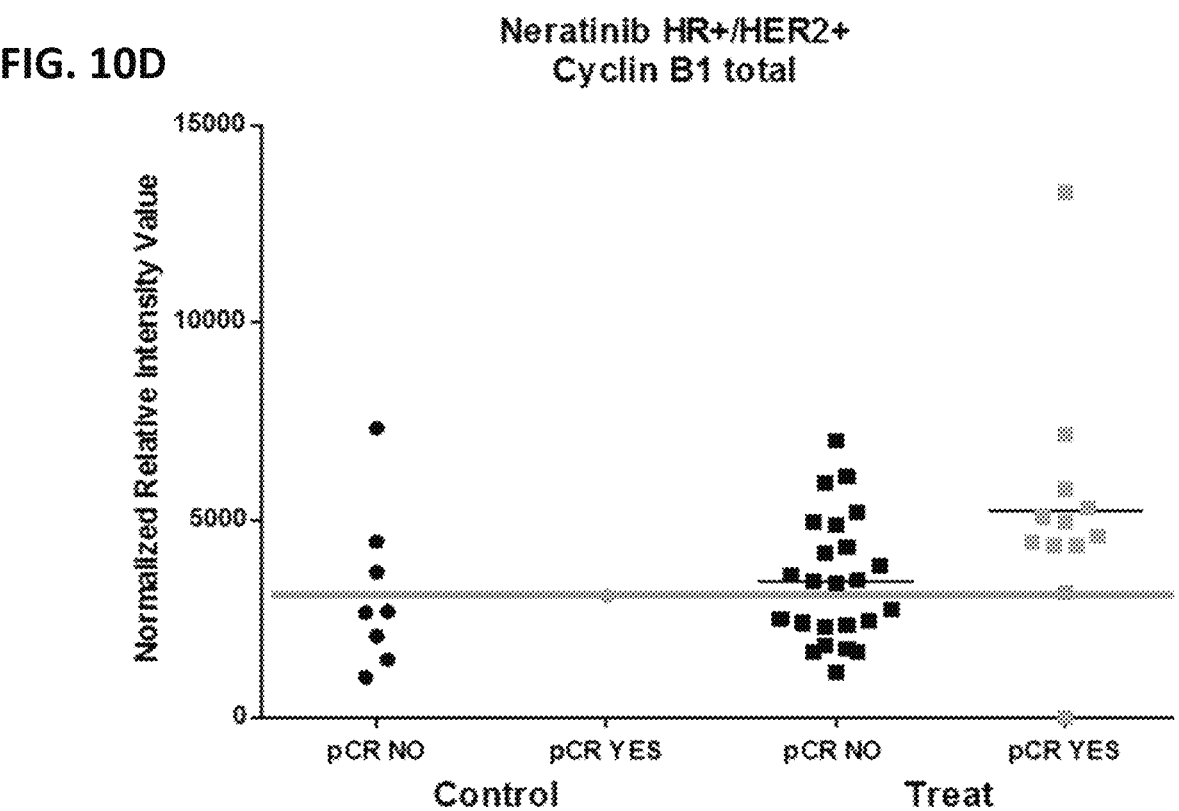
Figure 10E:
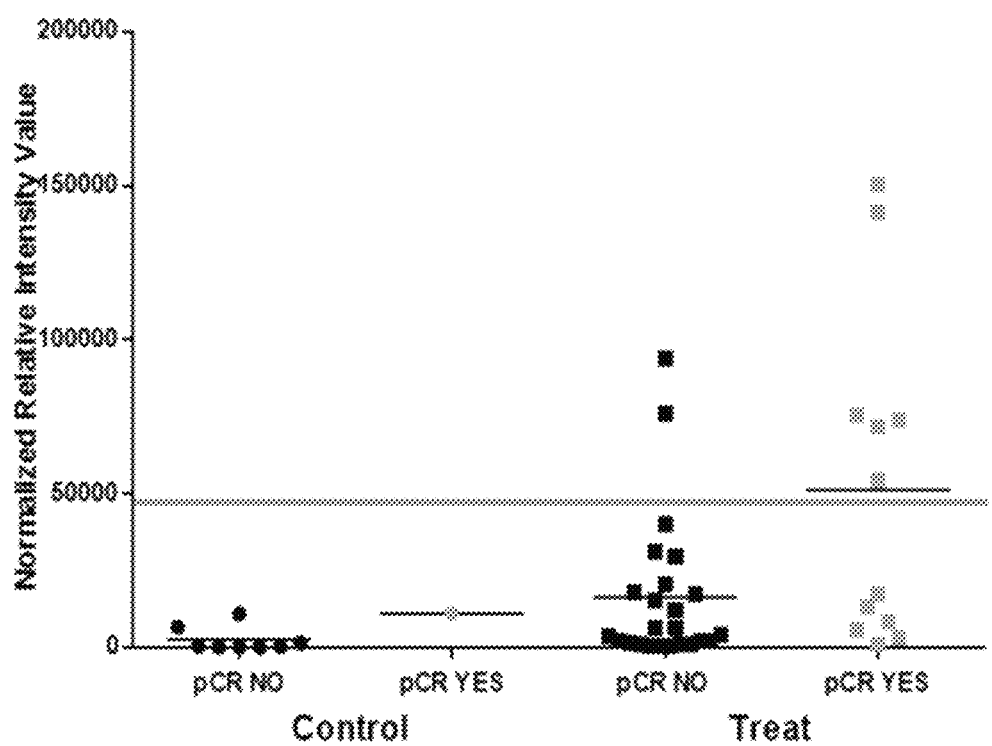
Figure 10F:
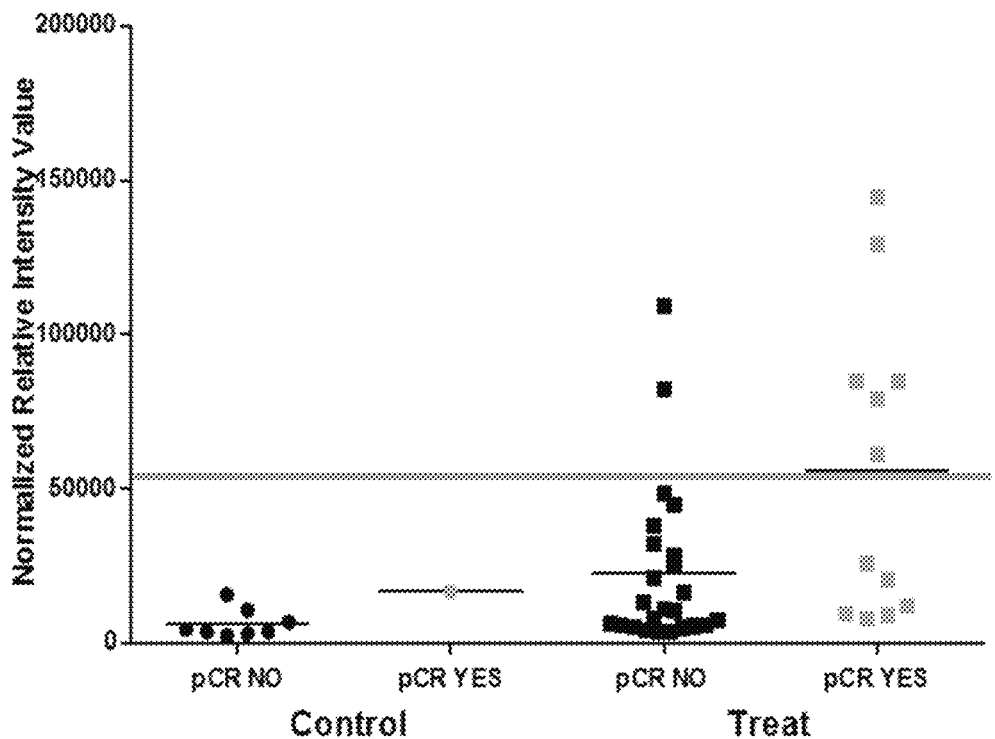
Figure 10G:
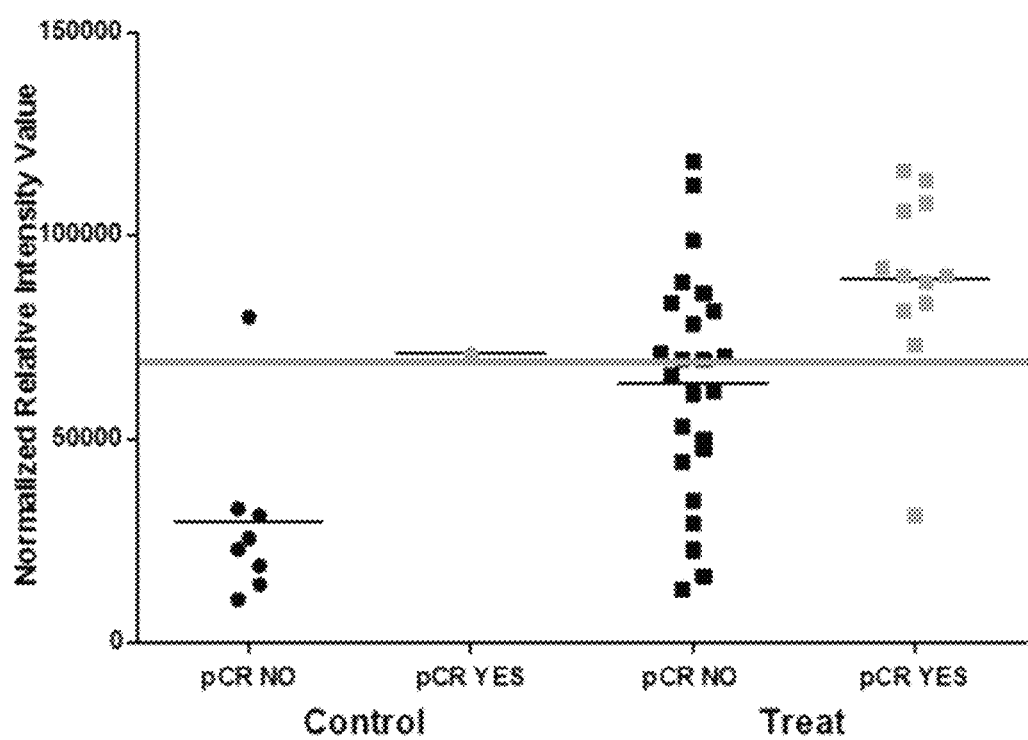
Figure 10H:
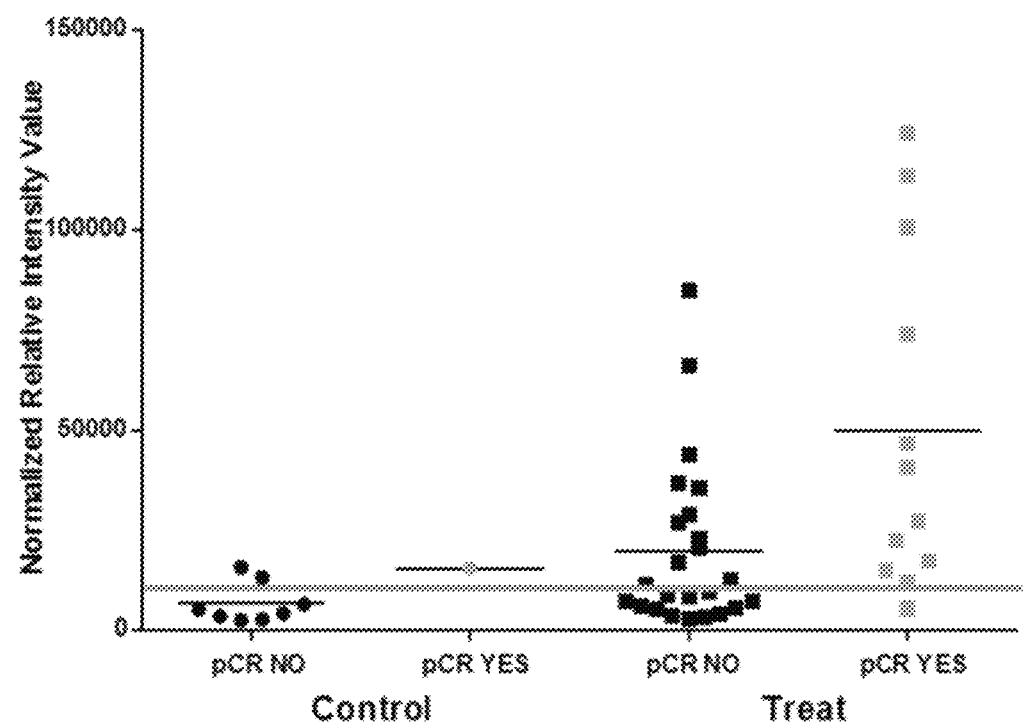
Figure 10I:
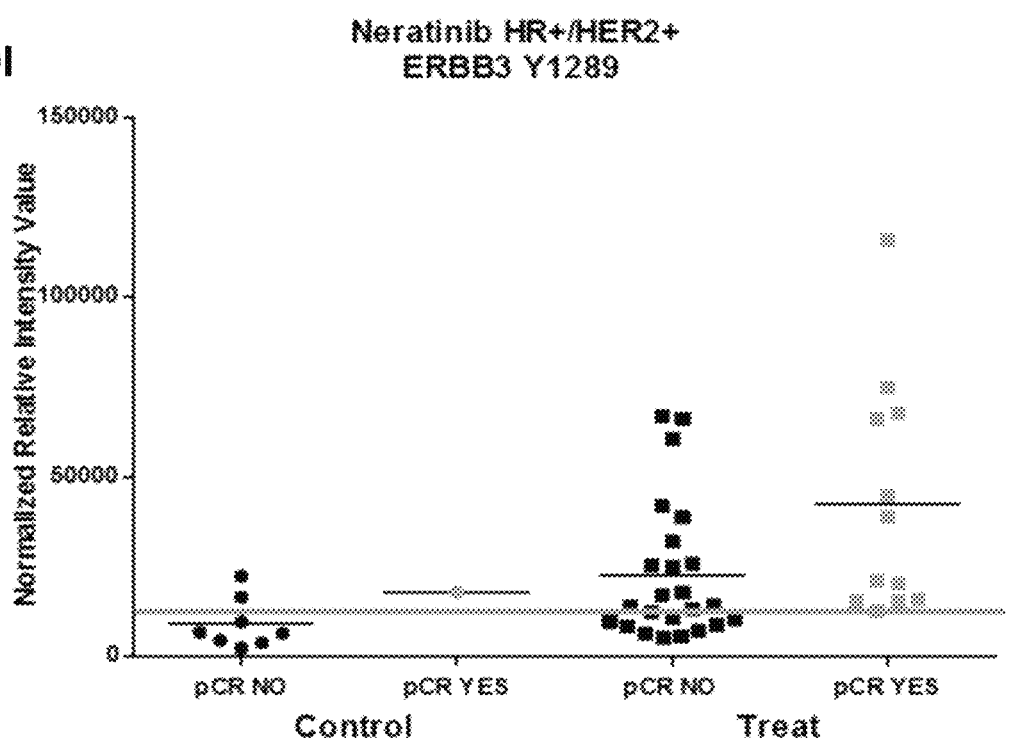
Figure 10J:
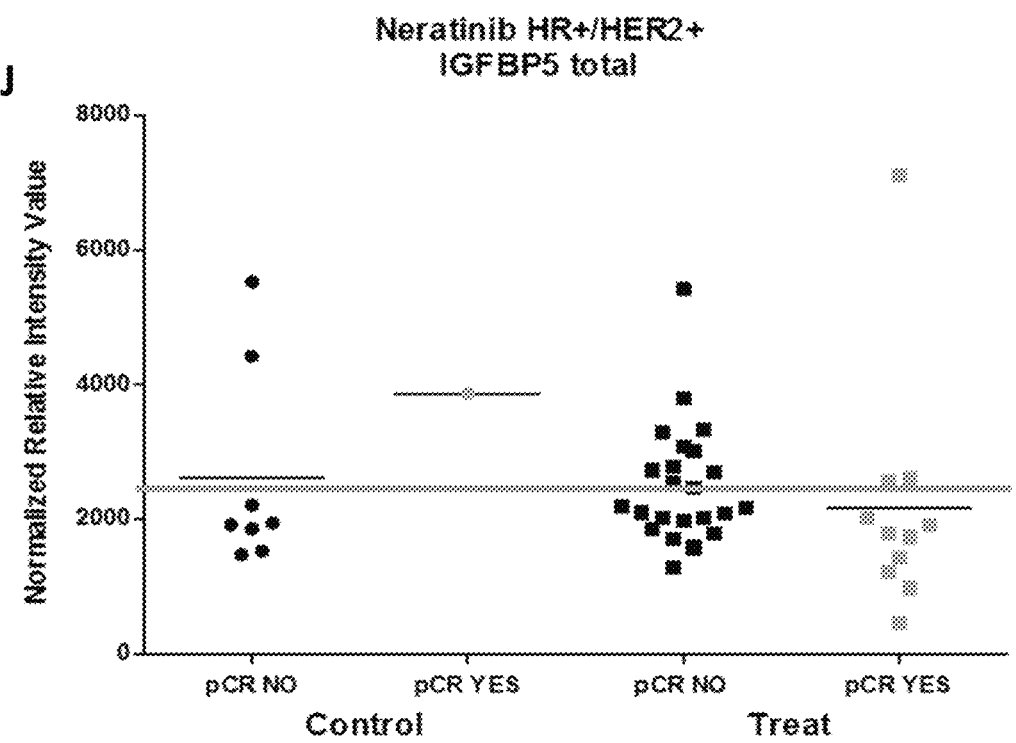

As shown in FIG. 3, each array contained a printed calibrator(s), a series of cell lystates derived from cells treated with a variety of mitogens such that broad pathway activation has been achieved. The calibrator(s) consisted of 6-10 dilutions of whole cell lysates from stimulated and unstimulated cells (eg. HeLa cells treated and untreated with pervandate for 30 minutes; jurkat cells treated and untreated with calyculin for 30 minutes; A431 cells treated and untreated with EGF for 30 minutes) pre-mixed in various ratios such that the total protein in any spot does not change, but the phospho-analyte changes in a predictable and defined concentration. Another type of calibrator can be prepared by spiking-in known amounts of recombinant protein or peptides that correspond to the target analyte and react specifically with antibodies directed to the target protein into a lystate that does not contain the target analyte. The exact same calibrator was printed on every single slide. The defining characteristic of this calibrator was that protein concentration does not vary but staining intensity did. Much like a clinical assay run in a diagnostic laboratory, each experimental value was extrapolated to a non-parametric curve fit of the calibrator within the region that spanned the dynamic range of the population such that results can be compared over time and across arrays. The calibrator was defined either in absolute amounts (if the analyte concentration is known), or in relative units (RUs) if the absolute amount of the analyte within the calibrator is not known. Most applications will use RU calibration units.

Data Normalization

Each protein analyte value was normalized to the total amount of protein printed on that spot by first incubated the slide with a florescent stain (Sypro Ruby Blot Stain, Molecular Probes, Eugene Oreg.) that binds to proteins without bias and did not interfere with subsequent antibody binding. The protein loading value is also obtained by a calibrated assay technique. A protein calibration curve of the exact same sample was printed on every slide. This total protein calibrator consisted of a protein lysate, which upon dilution, spanned the linear dynamic range of protein concentration. Each sample value was then extrapolated to the calibrator. Consequently, while the total amount of protein may vary in any given sample compared to each other—thus affecting phopsho-protein measurements for each sample, this variance was greatly minimized by such a normalization procedure.

Blocking Procedure

Once arrays were printed and stained for total protein, slides underwent a blocking procedure. Casein based solutions provided a uniform protein solution capable of binding to non-antigenic sites on nylon, PVDF and nitrocellulose membranes. Casein blocked these sites, inhibiting binding of antibody. This resulted in reduced background staining for reverse phase protein arrays.

Staining and Image Acquisition

Arrays were probed using an antibody specific for the phospho-protein, or any protein analyte. Over 350 phospho-proteins have been extensively pre-validated for specificity using Western blotting and peptide competition. A Dako Cytomation Autostainer (FDA approved for the HercepTest) was used to perform the staining procedure. This included the processes of incubation with primary antibody, specific for the analyte of interest as well as incubation with secondary antibody. A signal was generated using a near-IR fluorescent dye (LICOR Biosciences) that was coupled to the secondary antibody. The RPPA used a fluorometric image capture processing system (e.g. NovaRay, Alpha Innotech) for image acquisition. The system measured the sample's fluorescence intensity value, subtracted the background, normalized the result to the total protein, and extrapolated the value to the non-parametrically fit calibration curve to generate a final intensity value. The median of the triplicate values was reported.

Correlation of Calibrated Values with Clinical Outcomes

Calibrated values of patient samples were correlated with outcomes results (discontinuous variables (alive v dead, long v short survival), or continuous variables (overall survival, disease free survival, time to progression, etc). These values were usually reported in days, weeks or months. Statistical analysis was used for the correlative findings. Parametric (e.g., Student t-test) or non-parametric (e.g. Wilcoxon Rank Sum) of mean comparison was used, Kaplan Meir and ROC curves were used to uncover relationships between continuous clinical variables and continuous calibrated values. Optimally, any optimal cutpoint found by such analysis should be tested in independent study sets using ROC and or KM type analysis.

Those skilled in the art will recognize, or be able to ascertain using no more than routine experimentation, many equivalents to the specific embodiments of the method and compositions described herein. Such equivalents are intended to be encompassed by the following claims.

What is claimed is:

1. A method for treating breast cancer regardless of ER, PR and/or HER2 status, comprising, treating a subject identified as having breast cancer regardless of ER, PR and/or HER2 status with at least one tyrosine kinase inhibitor ("TKI") that targets EGFR and HER2, wherein the efficacy of the at least one TKI has been determined by a) measuring protein levels of one or more biomarkers in cellular samples from the subject prior to treatment with the TKI, and b) comparing the measured protein levels of the one or more biomarkers from the subject to a baseline value for the respective one or more biomarkers, wherein an elevated or decreased level of the proteins of the one or more biomarkers indicates that the subject is a responder to the TKI, wherein a biomarker is selected from one or more of the following: ALK.Y1586; Cyclin.B1 total; EGFR.Y1068; EGFR.Y1173; EGFR.Y992; eIF4G.S1108; ERBB2.total; ERBB2.Y1248; ERBB2.Y877; ERBB4.Y1284; RET Y905; SHC Y317; an mTOR pathway score (which is the sum of the measurements for 4EBP1 S65; eIF4E S209; eIF4G S1108; eIF4G S1108; eIF4G S1108; mTOR S2448; p70S6K S371; p70S6K T389; p70S6K T412; S6RP S240/S244); a HER Family pathway score (which is the sum of the measurements for EGFR Y1068; EGFR Y1173; EGFR Y992; ERBB2 Y1248; ERBB3 Y1289; FAK Y576/Y577; SHC Y317; STAT5 Y694; RET Y905); and a RTK pathway score (which is the sum of the measurements for ALK Y1604; EGFR Y1068; EGFR Y1173; EGFR Y992; ERBB2 Y1248; ERBB3 Y1289; FAK Y576/Y577; SHC Y317; STAT5 Y694; ERBB2 Y877; ERBB4 Y1284; MET Y1234-Y1235; ROS Y2274; RET Y905), or combinations thereof.

2. The method of claim 1, wherein measurements are made with reverse phase protein microarray, ELISA, immunohistochemistry, western blot, dot blot, mass spectrometry, mass cytometry, antibody array, or suspension bead array.

3. The method of claim 1, wherein the subject is identified as having Stage II/III breast cancer.

4. The method of claim 1, wherein the subject has been treated with chemotherapy.

5. The method of claim 1, wherein the one or more proteins is phosphorylated EGFR Y1173, and wherein the cellular sample comprises breast cancer cells of subtype HER2+/HR−.

6. The method of claim 1, wherein the TKI comprises neratinib, affatinib, lapatinib, pan-HER inhibitors or pan-EGFR inhibitors.

7. The method of claim 1, wherein the subject is a human patient.

8. The method of claim 5, wherein the subject is a human patient.

9. The method of claim 6, wherein the subject is a human patient.

* * * * *